United States Patent [19]

Roberts et al.

[11] Patent Number: 5,198,439
[45] Date of Patent: Mar. 30, 1993

[54] ANGIOTENSION II ANTAGONIZING PYRIDINE DERIVATIVES

[75] Inventors: David A. Roberts, Congleton; Arnold H. Ratcliffe, Poynton; Robert H. Bradbury, Wilmslow, all of England

[73] Assignee: Imperial Chemical Industries PLC, London, England

[21] Appl. No.: 874,785

[22] Filed: Apr. 27, 1992

Related U.S. Application Data

[62] Division of Ser. No. 687,270, Apr. 18, 1991, Pat. No. 5,130,318.

[30] Foreign Application Priority Data

Apr. 19, 1990 [GB] United Kingdom ............... 9008817
Dec. 7, 1990 [GB] United Kingdom ............... 9026617

[51] Int. Cl.$^5$ .................. C07D 401/10; A61K 31/44
[52] U.S. Cl. ........................... 514/236.2; 514/340; 514/341; 514/344; 514/346; 514/347; 514/348; 514/349; 514/350; 514/351; 544/124; 546/194; 546/256; 546/276; 546/278; 546/287; 546/288; 546/291; 546/293; 546/295; 546/297; 546/298; 546/299; 546/300; 546/301; 546/302
[58] Field of Search ............... 546/276, 278, 287, 288, 546/291, 194, 256, 293, 295, 297, 298, 299, 300, 301, 302; 544/124; 514/236.2, 340, 341, 344, 346, 347, 348, 349, 350, 351

[56] References Cited

U.S. PATENT DOCUMENTS 4,820,843  4/1989  Aldrich et al. .................... 548/252
4,880,804  11/1989  Carini et al. ..................... 514/234.5

FOREIGN PATENT DOCUMENTS 0253310  1/1988  European Pat. Off. .
0323841  7/1989  European Pat. Off. .
0412848  2/1991  European Pat. Off. .
0445811  9/1991  European Pat. Off. .
0475206  3/1992  European Pat. Off. .
0487745  6/1992  European Pat. Off. .
2428305  1/1975  Fed. Rep. of Germany .

OTHER PUBLICATIONS

G. R. Proctor, et al., *J. Chem. Soc., Perkin Trans. I* (1972) (14), 1803-8.

*Primary Examiner*—Bernard Dentz
*Attorney, Agent, or Firm*—Thomas E. Jackson

[57] ABSTRACT

The invention concerns pharmaceutically useful novel compounds of the formula I, in which $R^1$, $R^2$, $R^3$, $R^4$, $R^5$, $R^6$, $R^7$, X and Z have the various meanings defined herein, and their non-toxic salts, and pharmaceutical compositions containing them. The novel compounds are of value in treating conditions such as hypertension and congestive heart failure. The invention further concerns processes for the manufacture of the novel compounds and the use of the compounds in medical treatment.

11 Claims, No Drawings

ANGIOTENSION II ANTAGONIZING PYRIDINE DERIVATIVES

This is a divisional application of co-pending application Ser. No. 07/687,270 filed on Apr. 18, 1991, now U.S. Pat. No. 5,130,318.

This invention concerns novel pyridine derivatives and, more particularly, novel pyridine derivatives which possess pharmacologically useful properties in antagonising at least in part one or more of the actions of the substances known as angiotensins, and in particular of that known as angiotensin II (hereinafter referred to as "AII"). The invention also concerns pharmaceutical compositions of the novel compounds for use in treating diseases or medical conditions such as hypertension, congestive heart failure and/or hyperaldosteronism in warm-blooded animals (including man), as well as in other diseases or medical conditions in which the renin-angiotensin-aldosterone system plays a significant causative role. The invention also includes processes for the manufacture of the novel compounds and their use in treating one of the afore-mentioned diseases or medical conditions and for the production of novel pharmaceuticals for use in such medical treatments.

The angiotensins are key mediators of the renin-angiotensin-aldosterone system, which is involved in the control of homeostasis and fluid/electrolyte balance in many warm-blooded animals, including man. The angiotensin known as AII is produced by the action of angiotensin converting enzyme (ACE) from angiotensin I, itself produced by the action of the enzyme renin from the blood plasma protein angiotensinogen. AII is a potent spasmogen especially in the vasculature and is known to increase vascular resistance and blood pressure. In addition, the angiotensins are known to stimulate the release of aldosterone and hence result in vascular congestion and hypertension via sodium and fluid retention mechanisms. Hitherto there have been a number of different approaches to pharmacological intervention in the renin-angiotensin-aldosterone system for therapeutic control of blood pressure and/or fluid/electrolyte balance, including, for example, inhibiting the actions of renin or ACE. However, there remains a continuing need for an alternative approach because of the side-effects and/or idiosyncratic reactions associated with any particular therapeutic approach.

In our co-pending European Patent Application, Publication No. 412848 there are described certain quinoline derivatives having AII antagonist activity.

We have now discovered that the compounds of the invention (set out below) surprisingly antagonise one or more of the actions of the substances known as angiotensins (and in particular of AII) and thus minimise the physiological effects associated with their presence in warm-blooded animals (including man) and this is the basis of the invention.

According to the invention there is provided a pyridine derivative of the formula I (set out hereinafter, together with the other chemical formulae identified by Roman numerals) wherein $R^1$ is hydrogen, (1-8C)alkyl, (3-8C)cycloalkyl, phenyl or substituted (1-4C)alkyl, the latter containing one or more fluoro substituents or bearing a (3-8C)cycloalkyl, (1-4C)alkoxy or phenyl substituent; $R^2$ is hydrogen, (1-8C)alkyl, (3-8C)cycloalkyl, (3-8C)cycloalkyl-(1-4C)alkyl, carboxy, (1-4C)alkoxycarbonyl, (3-6C)alkenyloxycarbonyl, cyano, nitro, phenyl or phenyl(1-4C)alkyl; $R^3$ is selected from halogeno, (1-4C)alkoxy, amino, alkylamino and dialkylamino of up to 6 carbon atoms, and any of the values defined for $R^1$; $R^4$ is selected from hydrogen, (1-4C)alkyl optionally bearing an amino, (1-4C)alkanoylamino, phenylcarbonylamino, hydroxy or (1-4C)alkoxy substituent, carboxy, (1-4C)alkoxycarbonyl, (3-6C)alkenyloxycarbonyl, cyano, nitro, carbamoyl, (1-4C)alkanoyl, N-alkylcarbamoyl and di-(N-alkyl)carbamoyl of up to 7 carbon atoms, halogeno, amino, alkylamino and dialkylamino of up to 6 carbon atoms, 3-(1-4C)alkylureido and (1-4C)alkanoylamino; or $R^4$ is a group of the formula $-A^1.A^2.B$ wherein $A^1$ is carbonyloxy, $A^2$ is (1-6C)alkylene and B is selected from hydroxy, (1-4C)alkoxy, phenyloxy, phenyl(1-4C)alkoxy, pyridyl(1-4C)alkoxy, 4-morpholino(1-4C)alkoxy, phenylamino, amino, alkylamino and dialkylamino of up to 6 carbon atoms, (1-4C)alkanoylamino, (1-4C)alkylsulphonylamino, phenylsulphonylamino, sulphamoylamino ($-NH.SO_2.NH_2$), carboxamidomethylamino ($-NH.CH_2.CO.NH_2$), (1-4C)alkanoyloxy, phenylcarbonyloxy, aminocarbonyloxy ($-O.CO.NH_2$), (1-4C)alkylaminocarbonyloxy, carboxy, (1-4C)alkoxycarbonyl, carbamoyl, N-alkylcarbamoyl and di-(N-alkyl)carbamoyl of up to 7 carbon atoms, (1-4C)alkanoyl, 4-morpholino, 1-imidazolyl and succinimido group; or B is a group of the formula $-A^3.B^1$ wherein $A^3$ is oxy, oxycarbonyl or imino and $B^1$ is a 5 or 6-membered saturated or unsaturated heterocyclic ring containing 1 or 2 nitrogen atoms and linked to $A^3$ by a ring carbon atom; or $A^3$ is oxycarbonyl and $B^1$ is a 4-morpholino group or a 5 or 6-membered saturated heterocyclic ring containing 1 or 2 nitrogen atoms, optionally bearing a (1-4C)alkyl group and linked to $A^3$ by a ring nitrogen atom; and wherein $B^1$ the remainder of the ring atoms are carbon; or $R^3$ and $R^4$ together form (3-6C)alkylene, one of the methylene groups of which may optionally be replaced by a carbonyl group, or (3-6C)alkenylene; $R^5$ is hydrogen; $R^6$ hydrogen or (1-4C)alkyl; $R^7$ is selected from hydrogen, (1-4C)alkyl, (1-4C)alkoxy, halogeno, trifluoromethyl, cyano and nitro; X is phenylene optionally bearing a substituent selected from (1-4C)alkyl, (1-4C)alkoxy, halogeno, (1-4C)alkanoyl, trifluoromethyl, cyano and nitro, or X is a direct bond between the adjacent phenyl group and the carbon atom bearing $R^5$ and $R^6$; Z is 1H-tetrazol-5-yl, $-CO.NH.(1H\text{-tetrazol-5-yl})$ or a group of the formula $-CO.OR^8$ or $-CO.NH.SO_2.R^9$ in which $R^8$ is hydrogen or a non-toxic, biodegradable residue of a physiologically acceptable alcohol or phenol, and $R^9$ is (1-6C)alkyl, (3-8C)cycloalkyl or phenyl; and wherein any of said phenyl moieties may be unsubstituted or bear one or two substituents independently selected from (1-4C)alkyl, (1-4C)alkoxy, halogeno, cyano and trifluoromethyl; or an N-oxide thereof; or a non-toxic salt thereof.

It will appreciated that, depending on the nature of the substituents, certain of the formula I compounds may possess one or more chiral centres and may be isolated in one or more racemic or optically active forms. It is to be understood that this invention concerns any form of such a compound of formula I which possesses the afore-mentioned useful pharmacological properties, it being well known how to make optically active forms, for example by synthesis from suitable chiral intermediates, and how to determine their pharmacological properties, for example by use of the standard tests described hereinafter.

It is to be understood that generic terms such as "alkyl" include both straight and branched chain variants when the carbon numbers permit. However, when a particular radical such as "propyl" is given, it is specific to the straight chain variant, branched chain variants such as "isopropyl" being specifically named where intended. The same convention applies to other radicals.

A particular value for $R^1$, $R^2$ or $R^3$ when it is alkyl is, for example, methyl, ethyl, propyl, isopropyl, butyl, isobutyl, sec-butyl, pentyl or hexyl; and when it is cycloalkyl is, for example, cyclopropyl, cyclopentyl or cyclohexyl.

A particular value for $R^1$ or $R^3$ when it is alkyl bearing one or more fluoro substituents is, for example, fluoromethyl, trifluoromethyl, 2,2,2-trifluoroethyl or pentafluoroethyl; and when it is alkyl bearing a cycloalkyl, (1–4C)alkoxy or phenyl substituent is, for example, cyclopropylmethyl, cyclopentylmethyl, cyclohexylmethyl, 2-methoxyethyl, 2-ethoxyethyl, benzyl, 1-phenylethyl or 2-phenylethyl.

A particular value for $R^2$ when it is cycloalkyl-alkyl is, for example, cyclopropylmethyl, cyclopentylmethyl, cyclohexylmethyl or 2-cyclopentyl-ethyl; and when it is phenylalkyl is, for example, benzyl, 1-phenylethyl or 2-phenylethyl.

A particular value for $R^2$ or $R^4$ when it is alkoxycarbonyl is, for example, methoxycarbonyl, ethoxycarbonyl or propoxycarbonyl; and when it is alkenyloxycarbonyl is, for example, allyloxycarbonyl, 2-methyl-2-propenyloxycarbonyl or 3-methyl-3-butenyloxycarbonyl.

A particular value for $R^4$, $R^6$ or $R^7$, or for an optional substituent which may be present when X is phenylene, when it is alkyl is, for example, methyl or ethyl.

A particular value for $R^3$, $R^4$, $R^7$ or for an optional substituent which may be present when X is phenylene, when it is halogeno is, for example, fluoro, chloro, bromo or iodo.

A particular value for $R^3$, $R^7$ or for an optional substituent which may be present when X is phenylene, when it is alkoxy is, for example, methoxy or ethoxy.

A particular value for $R^3$ or $R^4$ when it is alkylamino is, for example, methylamino, ethylamino or butylamino; and when it is dialkylamino is, for example, dimethylamino, diethylamino or dipropylamino.

Particular values for $R^4$ are, by way of example, for alkanoylamino: formamido, acetamido or propanamido; for alkanoyl: formyl, acetyl or butyryl; for N-alkylcarbamoyl: N-methyl or N-ethylcarbamoyl; for di(N-alkyl)carbamoyl: N,N-dimethylcarbamoyl or N,N-diethylcarbamoyl; for 3-alkylureido: 3-methylureido, 3-ethylureido or 3-propylureido; and for alkyl bearing an amino, alkanoylamino, phenylcarbonylamino, hydroxy or alkoxy substituent: aminomethyl, 2-aminoethyl, acetylaminomethyl, acetylaminoethyl, propionylaminomethyl, propionylaminoethyl, phenylcarbonylaminomethyl, phenylcarbonylaminoethyl, hydroxymethyl, 1-hydroxyethyl, 2-hydroxyethyl, methoxymethyl, 2-methoxyethyl or 2-ethoxyethyl.

A particular value for $R^3$ and $R^4$ when together they form (3–6C)alkylene is, for example, trimethylene, tetramethylene or pentamethylene; when together they form (3–6C)alkenylene is, for example, 1-propylene, 2-propenylene, 1-butenylene, 2-butenylene or 3-butenylene; and when together they form (3–6C)alkylene wherein one of the methylene groups is replaced by a carbonyl group is, for example, 1-oxopropylidene, 3-oxopropylidene, 1-oxobutylidene or 4-oxobutylidene.

A particular value for an optional substituent on X when it is phenylene, when it is alkanoyl, is, for example, formyl, acetyl or propionyl.

A particular value for $A^2$ is, for example, methylene, ethylene, trimethylene or tetramethylene, in any of which one methylene may bear 1 or 2 methyl substituents.

A particular value for B includes, for example, for alkoxy: methoxy, ethoxy and isopropoxy; for phenylalkoxy: benzyloxy and phenethyloxy; for pyridylalkoxy: 2-pyridylmethoxy, 3-pyridylmethoxy, 4-pyridylmethoxy and 3-pyridylethoxy; for 4-morpholinoalkoxy: 4-morpholinomethoxy and 4-morpholinoethoxy; for alkylamino: methylamino, ethylamino and butylamino; for dialkylamino: dimethylamino, diethylamino and dipropylamino; for alkanoylamino: formamido, acetamido and propanamido; for alkylsulphonylamino: methylsulphonylamino and ethylsulphonylamino; for alkanoyloxy: acetyloxy and propionyloxy; for alkylaminocarbonyloxy: methylaminocarbonyloxy and ethylaminocarbonyloxy; for alkoxycarbonyl: methoxycarbonyl, ethoxycarbonyl and propoxycarbonyl; for N-alkylcarbamoyl: N-methyl and N-ethylcarbamoyl; for di(N-alkyl)carbamoyl: N,N-dimethylcarbamoyl and N,N-diethylcarbamoyl; and for alkanoyl: formyl, acetyl and propionyl.

A particular value for $B^1$ when it is a 5 or 6-membered unsaturated heterocyclic ring containing 1 or 2 nitrogen atoms is, for example, pyrrolyl, imidazolyl, pyrazolyl, pyridyl, pyrazinyl, pyrimidinyl or pyridazinyl; and when it is a 5 or 6-membered saturated heterocyclic ring containing 1 or 2 nitrogen atoms is, for example, pyrrolidinyl, imidazolidinyl, pyrazolinyl, piperidinyl or piperazinyl.

A particular value for an alkyl group which may be present on $B^1$ when it is a 5 or 6-membered saturated heterocyclic ring is, for example, methyl or ethyl.

A particular value for $R^8$ when it is a non-toxic, biodegradable residue of a physiologically acceptable alcohol or phenol is, for example, a residue derived from a (1–6C)alkanol such as methanol or ethanol, or phenol, glycerol or the like.

A particular value for $R^9$ when it is alkyl is, for example, methyl, ethyl, propyl, isopropyl, butyl or pentyl; and when it is cycloalkyl is, for example, cyclobutyl, cyclopentyl or cyclohexyl.

Particular values for optional substituents which may be present on phenyl moieties include, by way of example, for halogeno: fluoro, chloro and bromo; for alkyl: methyl and ethyl; and for alkoxy: methoxy and ethoxy.

A specific value for X which is of particular interest is, for example, p-phenylene.

A preferred value for $R^1$ or $R^3$ is, for example, methyl or ethyl.

A preferred value for $R^2$ is, for example, hydrogen, unsubstituted phenyl or phenyl bearing one or two substituents independently selected from methyl, ethyl, methoxy, ethoxy, fluoro, chloro, bromo, iodo, cyano and trifluoromethyl.

A preferred value for $R^4$ is, for example, hydrogen, alkoxycarbonyl (especially methoxycarbonyl or ethoxycarbonyl) or alkenyloxycarbonyl (especially allyloxycarbonyl).

A preferred value for $R^3$ and $R^4$ when together they form alkylene is, for example, trimethylene or tetramethylene, the latter being especially preferred.

A preferred value for $R^6$, $R^7$ or $R^8$ is, for example, hydrogen.

A preferred value for Z is, for example, 1H-tetrazol-5-yl and which is especially preferred when attached ortho to the group X.

A particularly preferred combination of values is, for example, when $R^1$ and $R^3$ are both alkyl (such as when $R^1$ is methyl or ethyl and $R^3$ is methyl or ethyl), or $R^1$ is alkyl (such as methyl or ethyl) and $R^3$ together with $R^4$ form alkylene (such as trimethylene, tetramethylene or pentamethylene).

A further particularly preferred combination of values is, for example, when $R^4$ is hydrogen and $R^2$ is unsubstituted phenyl or phenyl bearing one or two substituents independently selected from (1–4C)alkyl (such as methyl, ethyl or propyl), (1–4C)alkoxy (such as methoxy or ethoxy), halogeno (such as fluoro, chloro, bromo or iodo), cyano and trifluoromethyl.

A still further particularly preferred combination of values is, for example, when $R^2$ is hydrogen and $R^4$ is alkoxycarbonyl (such as methoxycarbonyl or ethoxycarbonyl) or alkenyloxycarbonyl (such as allyloxycarbonyl).

A group of compounds of the invention which is of particular interest comprises those compounds of the formula I wherein $R^1$, $R^2$, $R^3$, $R^5$, $R^6$, $R^7$, X and Z have any of the meanings defined above and $R^4$ is a group of the formula $A^1.A^2.B$ wherein $A^1$, $A^2$ and B have any of the meanings defined above; and the non-toxic salts thereof.

A preferred group of compounds of the formula I comprises those compounds of the formula I wherein X is p-phenylene and Z is 1H-tetrazol-5-yl, and wherein $R^1$, $R^2$, $R^3$, $R^4$, $R^5$, $R^6$ and $R^7$ have any of the values defined above; and the non-toxic salts thereof. Especially preferred within this group are those compounds wherein Z is at the ortho position relative to X.

A particularly preferred group of compounds of the formula I comprises those compounds of the formula I wherein $R^1$, $R^2$, $R^3$, $R^5$ and $R^7$ have any of the values defined above, $R^4$ is (1–4C)alkoxycarbonyl or (3–6C)alkenyloxycarbonyl, $R^6$ is hydrogen and Z is carboxy or 1H-tetrazol-5-yl; and the non-toxic salts thereof. Especially preferred within this group are those compounds wherein Z is at the ortho position relative to X, and particularly wherein Z is 1H-tetrazol-5-yl.

A further particularly preferred group of compounds of the invention comprises compounds of the formula Ia wherein n is the integer 1, 2 or 3; Rz is hydrogen or a substituent selected from (1–4C)alkyl, (1–4C)alkoxy, halogeno, (1–4C)alkanoyl, trifluoromethyl, cyano and nitro; Za is 1H-tetrazol-5-yl or carboxy; and $R^1$, $R^2$ and $R^7$ have any of the meanings defined above; and the non-toxic salts thereof. Especially of interest within this group are those compounds wherein Za is 1H-tetrazol-5-yl.

A still further particularly preferred group of compounds of the invention comprises compounds of the formula Ib wherein $R^1$, $R^3$, $R^4$, and $R^7$ have any of the values defined above; Rz is hydrogen or a substituent selected from (1–4C)alkyl, (1–4C)alkoxy, halogeno, (1–4C)alkanoyl, trifluoromethyl, cyano and nitro; Rx and Ry are independently selected from hydrogen, (1–4C)alkyl, (1–4C)alkoxy, halogeno, cyano and trifluoromethyl; and Zb is 1H-tetrazol-5-yl or carboxy; and the non-toxic salts thereof. Especially prefered within this group are those compounds wherein Z is 1H-tetrazol-5-yl.

Compounds of the invention which are of particular interest include, for example, the specific embodiments set out hereinafter in the accompanying Examples. Of these, the compounds of formula I described in Examples 2, 5, 6, 9, 10, 11, 12, 13, 14 and 41 are of special interest and these compounds, or a non-toxic salt thereof, are provided as a further feature of the invention.

Although all of the formula I compounds can form salts with suitable acids, it will be appreciated that those compounds of formula I wherein Z is other than an ester group or in which $R^2$ or $R^4$ bear a carboxy group can form salts with bases as well as with acids. Particularly suitable non-toxic salts for such compounds therefore also include, for example, salts with bases affording physiologically acceptable cations, for example, alkali metal (such as sodium and potassium), alkaline earth metal (such as magnesium and calcium), aluminium and ammonium salts, as well as salts with suitable organic bases, such as with ethanolamine, methylamine, diethylamine or triethylamine, as well as salts with acids forming physiologically acceptable anions, such as salts with mineral acids, for example with hydrogen halides (such as hydrogen chloride and hydrogen bromide), sulphuric and phosphoric acid, and with strong organic acids, for example with p-toluenesulphonic and methanesulphonic acids.

The compounds of formula I may be obtained by standard procedures of organic chemistry well known in the art for the production of structurally analogous compounds. Such procedures are provided as a further feature of the invention and include, by way of example, the following procedures in which the generic radicals have any of the values given above, unless stated otherwise:

a) For those compounds in which Z is carboxy (that is in which Z is a group of the formula $-CO.OR^8$ in which $R^8$ is hydrogen), a carboxylic acid derivative of the formula II, in which Q is a protected carboxy group selected from (1–6C)alkoxycarbonyl (especially methoxy-, ethoxy-, propoxy- or t-butoxy-carbonyl), phenoxycarbonyl, benzyloxycarbonyl and carbamoyl, is converted to carboxy.

The conversion may be carried out, for example by hydrolysis, conveniently in the presence of a suitable base such as an alkali metal hydroxide, for example, lithium, sodium or potassium hydroxide. The hydrolysis is generally carried out in the presence of a suitable aqueous solvent or diluent, for example in an aqueous (1–4C)alkanol, such as aqueous methanol or ethanol. However, it may also be performed in a mixture of an aqueous and non-aqueous solvent such as water and toluene using a conventional quaternary ammonium phase transfer catalyst. The hydrolysis is generally performed at a temperature in the range, for example, 0°–120° C., depending on the reactivity of the group Q. In general, when Q is carbamoyl, temperatures in the range, for example, 40°–120° C. are required to effect the hydrolysis.

Alternatively, when Q is benzyloxycarbonyl the conversion may also be performed by hydrogenolysis, for example using hydrogen at 1–3 bar in the presence of a suitable catalyst, such as palladium on charcoal or on calcium sulphate, in a suitable solvent or diluent such as a (1–4C)alkanol (typically ethanol or 2-propanol) and at a temperature in the range, for example, 0°–40° C.

Further, when Q is t-butoxycarbonyl, the conversion may also be carried out by hydrolysis at a temperature in the range, for example, 0°–100° C., in the presence of a strong acid catalyst, such as trifluoroacetic acid. The hydrolysis may either be performed in an excess of the acid or in the presence of a suitable diluent such as tetrahydrofuran, t-butyl methyl ether or 1,2-dimethoxyethane.

b) For those compounds of formula I wherein Z is tetrazolyl, a compound of the formula III in which L is a suitable protecting group, such as trityl, benzhydryl, trialkyltin (for example trimethyltin or tributyltin) or triphenyltin, affixed to a nitrogen of the tetrazolyl moiety, is deprotected.

The reaction conditions used to carry out the deprotection necessarily depend on the nature of the group L. As an illustration, when it is trityl, benzhydryl, trialkyltin or triphenyltin, the decomposition conditions include, for example, acid catalysed hydrolysis in a mineral acid (such as aqueous hydrochloric acid), conveniently in an aqueous solvent (such as aqueous dioxan or 2-propanol). Alternatively, a trityl or benzhydryl group may be removed by hydrogenolysis, for example as described in (a) above for conversion of a benzyloxycarbonyl to a carboxy.

Compounds of the formula III wherein L is trialkyltin or triphenyltin may be obtained, for example, by reaction of a nitrile of the formula IX with a trialkyltin azide, such as tributyltin azide, or triphenyltin azide respectively. The reaction is conveniently carried out in a suitable solvent or diluent, such as toluene or xylene, and at a temperature in the range, for example, 50°–150° C. In a modified procedure, a formula I compound wherein Z is tetrazolyl may be obtained directly by in situ removal of the trialkyltin or triphenyltin group without prior isolation of the formula III compound, for example by the addition of aqueous mineral acid or gaseous hydrogen chloride to the reaction mixture. The nitriles of the formula IX may be obtained, for example, by alkylation of a pyridone of the formula IV wherein $R^1$ and $R^3$ are other than hydrogen with a nitrile of the formula X wherein Hal. stands for a suitable leaving group such as chloro, bromo, iodo, methanesulphonyloxy or p-toluenesulphonyloxy, using similar conditions to those used in process (c) described hereinafter. The necessary compounds of formula X may be made by standard procedures such as that illustrated in Scheme 1 for compounds in which X is phenylene, or from a compound of the formula XI using methods of organic chemistry well known in the art. Alternatively, the nitriles of the formula IX may be obtained from stepwise conversion of a compound of formula I wherein Z is a group of the formula —CO.OR$^8$ under standard conditions. The nitriles of the formula IX may also be obtained, for example, by reaction of a pyridine of the formula VII wherein $Y^1$ is a suitable leaving group (such as chloro, bromo, iodo, methanesulphonyl, methanesulphonyloxy, p-toluenesulphonyloxy or trifluoromethanesulphonyloxy) with an alcohol of the formula XI, using similar conditions to those used in process (d) described hereinafter. The alcohol of the formula XI may be obtained, for example, by standard procedures such as that illustrated in Scheme 1 for compounds in which X is phenylene, or by analogy with Scheme 2. As a still further alternative, nitriles of the formula IX may be obtained as shown in Scheme 4 for compounds wherein X is phenylene. Trialkyltin azides and triphenyltin azides are either commercially available or may be prepared by standard procedures well known in the art, such as by reaction of a trialkyltin halide with an alkali metal azide.

Alternatively, compounds of the formula III may be obtained, for example, by reaction of a pyridine of the formula VII wherein $Y^1$ is as defined above with an alcohol of the formula XII under similar conditions to those described in process (d) hereinafter. The alcohols of formula XII may be obtained, for example, from the appropriate bromomethyl compound by standard procedures such as those shown in Scheme 2.

It will be appreciated that a compound of the formula III may also be obtained from another previously prepared compound of the formula III by using standard functional group interconversions of a functional group or groups already present in the latter compound. Such interconversions are well known in the art. For example, a compound of the formula III wherein $R^4$ is an alkoxycarbonyl group may be converted to a formula III compound wherein $R^4$ is a carboxylic acid group by base hydrolysis or to a formula III compound wherein $R^4$ is a hydroxymethyl group by reduction with, for example, an alkali metal cyanoborohydride. The hydroxymethyl group may then, for example, be converted into its sodium salt with an alkali metal hydride and alkylated with, for example, an alkyl halide (such as iodomethane) to give an alkoxymethyl group. Alternatively the hydroxymethyl group may, for example, be converted into a halomethyl group (for example into a chloromethyl group with methanesulphonyl chloride and triethylamine), which may then be converted into an aminomethyl group by reaction with ammonia at high temperature in an autoclave. Subsequently, if a compound of the formula III is required in which $R^4$ is an alkanoylamino, phenylcarbonylamino or 3-alkylureido group, the aminomethyl group may, for example, be acylated under standard conditions with an appropriate acylating or benzoylating agent, or reacted with an alkyl isocyanate.

c) A pyridone of the formula IV wherein $R^1$ and $R^3$ are other than hydrogen is alkylated with a compound of the formula V wherein Hal. stands for a suitable leaving group such as chloro, bromo, iodo, methanesulphonyloxy or p-toluenesulphonyloxy.

The reaction is generally carried out in the presence of a suitable base, for example, an alkali metal alkoxide such as sodium methoxide or sodium ethoxide or an alkali metal hydride such as sodium hydride or an alkali metal carbonate such as sodium or potassium carbonate, or an organic base such as diisopropylethylamine and in a suitable solvent or diluent, for example, a (1–4C)alkanol such as methanol or ethanol when an alkali metal alkoxide is used, or in a polar solvent such as N,N-dimethylformamide or N-methylpyrrolidone and at a temperature in the range, for example, 10°–100° C. Alternatively, a quaternary ammonium hydroxide may be used in a mixture of an aqueous and non-aqueous solvent such as water and dichloromethane. In carrying out process (c), when in the starting material Z is an acidic group, about two molecular equivalents of a suitable base is generally required, whereas when Z is a non-acidic group the presence of one molecular equivalent of a suitable base is generally sufficient.

Procedure (c) is particularly suitable for the production of those compounds of the formula I in which Z is a group of the formula —CO.OR$^8$ in which $R^8$ is other than hydrogen, for example wherein $R^8$ is (1–6C)alkyl, benzyl or phenyl, which compounds are also starting materials of formula II for the reaction described in (a)

above. Similarly, using an analogous procedure, but starting with the appropriate halomethyl tetrazolyl derivative of the formula VI, the starting materials of the formula III may be obtained for procedure (b).

Many of the pyridones of formula IV are already known and the remainder can be made by analogy therewith using standard procedures of organic chemistry well known in the art, for example as described in standard works of heterocyclic chemistry such as that edited by Elderfield or using the procedures described in *Monatshefte fur Chemie*, 1969, 100, 132; *J. Chem. Soc.*(B),1968, 866; *Liebigs. Ann. Chem.*, 1982, 1656 or 1979, 371; *Heterocycles*, 1982, 13, 239; or European Patent Application, Publication No. 177965; or by analogy therewith. Alternatively, pyridones of the formula IV wherein $R^2$ is substituted or unsubstituted phenyl or phenylalkyl may be obtained as shown in Scheme 3 (or by analogy therewith) for compounds in which $R^1$ and $R^3$ are both methyl or ethyl and $R^4$ is hydrogen. The necessary compounds of the formula V (and also of formula VI) may be made by standard procedures such as those which are illustrated in Scheme 1 for compounds in which X is phenylene. Alternatively, a compound of the formula V or formula VI may be obtained from a formula VIII compound (in which Z is the group $CO.OR^8$) or formula XII compound respectively, using procedures of organic chemistry well known in the art.

Compounds of the formula VI wherein X is phenylene and $R^5$ and $R^6$ are both hydrogen may also be conveniently obtained by reaction of a Grignard reagent, formed from a suitably substituted 4-bromotoluene, with a trialkyltin halide, such as tributyltin chloride, followed by reaction of the resulting (substituted)- phenyltrialkyltin compound with a bromobenzonitrile in the presence of a palladium(O) catalyst, such as tetrakis(triphenylphosphine)palladium, and azo(bisisobutyronitrile). The resultant substituted 4'-methylbiphenylcarbonitrile may then be converted to a compound of the formula VI by carrying out steps (b), (c) and (d) in a similar manner to that shown in Scheme 1. Alternatively, suitably substituted 4'-methylbiphenylcarbonitriles may be obtained by reaction of 4-methylphenylboronic acid with an appropriately substituted bromobenzonitrile in the presence of a suitable palladium catalyst, such as palladium (II)chloride or tetrakis(triphenylphosphine)palladium, and azo(bisisobutyronitrile).

(d) A pyridine derivative of the formula VII wherein $Y^1$ is a suitable leaving group (such as chloro, bromo, iodo, methanesulphonyl, methanesulphonyloxy, p-toluenesulphonyloxy or trifluoromethanesulphonyloxy) is reacted with an alcohol of the formula VIII.

The reaction is generally carried out in the presence of a suitabl base, for example an alkali metal alkoxide such as sodium methoxide or ethoxide or an alkali metal hydride such as sodium hydride and in a suitable solvent or diluent, for example a (1–4C)alkanol such as methanol or ethanol when an alkali metal alkoxide is used, or a polar solvent such as N,N-dimethylformamide. Alternatively, an alcohol of the formula VIII may be used in the form of its preformed alkali metal salt (when Z is a non-acidic group) or di-alkali metal salt (when Z is an acidic group). The reaction is usually performed at a temperature in the range of 40° to 120° C. The reaction may in preference be carried out with a formula VIII compound in the presence of an acid catalyst such as p-toluenesulphonic acid, instead of under basic conditions, and in the presence of an inert solvent or diluent such as toluene. Yet a further alternative is to heat together a compound of the formula VII with a formula VIII compound at an elevated temperature, for example, at a temperature in the range 120°–180° C. and in the absence of solvent or in the presence of a high boiling solvent or diluent such as diphenyl ether.

Pyridine derivatives of the formula VII wherein $Y^1$ is halogeno may be obtained, for example, by halogenation of the corresponding pyridones of formula IV, for example, by reaction with phosphorus oxychloride in the absence of a solvent, or in the presence of an inert solvent or diluent such as toluene or dioxane, and at a temperature in the range 60°–110° C. Compounds of the formula VII wherein $Y^1$ is methanesulphonyloxy, p-toluenesulphonyloxy or trifluoromethanesulphonyloxy and $R^1$ and $R^3$ are other than hydrogen may be obtained, for example, by acylation of the corresponding pyridones of formula IV with the corresponding sulphonyl chloride under standard conditions. Compounds of the formula VII wherein $Y^1$ is methanesulphonyl may be obtained from alkylation of the corresponding mercaptopyridines followed by oxidation under standard conditions. The alcohols of the formula VIII are known or can be prepared by standard procedures well known in the art, for example, by analogy with Scheme 2 or deprotection of a compound obtained thereby.

Compounds of the formula I wherein Z is tetrazolyl and X is optionally substituted phenylene may also be obtained as shown in Scheme 5.

Whereafter, those compounds of formula I wherein Z is 1H-tetrazol-5-yl may be obtained by stepwise conversion of a compound of the formula I wherein Z is a group of the formula $-CO.OR^8$ into the corresponding nitrile under standard conditions, followed by reaction of the nitrile with an azide such as an alkali metal azide, preferably in the presence of an ammonium halide, and preferably in the presence of a suitable polar solvent such as N,N-dimethylformamide and at a temperature in the range, for example, 50° to 160° C.

Whereafter, those compounds of the formula I wherein Z is $-CO.NH.(1H\text{-tetrazol-5-yl})$, a group of the formula $-CO.NH.SO_2R^9$ or a group of the formula $-CO.OR^8$ in which $R^8$ is other than hydrogen, may be obtained, for example, by reacting a carboxylic acid of the formula I in which Z is carboxy (or a reactive derivative of said acid) with 5-aminotetrazole, a sulphonamide of the formula $NH_2.SO_2R^9$ or a salt thereof (for example, an alkali metal salt), or a hydroxy compound of the formula $HO.R^8$ or with a salt thereof (for example, an alkali metal thereof). Suitable reactive derivatives include, for example the chloride, bromide, azide, anhydride and mixed anhydride with formic or acetic acid of the carboxylic acid of formula I as defined above. When the free acid form is used, the reaction is generally carried out in the presence of a suitable dehydrating agent such as dicyclohexycarbodiimide or 3-(3-dimethylaminopropyl)-1-ethylcarbodiimide in the presence of a base such as triethylamine, pyridine or 4-dimethylaminopyridine. When a reactive derivative is used, either the reaction is carried out in the presence of a base such as mentioned above, or, for the preparation of a compound of the formula I wherein Z is a group of the formula $-CO.NH.SO_2R^9$ or a group of the formula $-CO.OR^8$, the sulphonamide or hydroxy compound is used in the form of a salt, such as its alkali metal salt (in particular the lithium, sodium or potassium salt thereof). The reaction is generally performed in the presence of a suitable diluent or solvent such as dioxan, t-butyl methyl ether or tetrahydrofuran and at a temperature in the range, for example, 0°–60° C.

Whereafter, when an N-oxide derivative of a compound of the formula I is required, a compound of the formula I is oxidised. Suitable oxidising agents include those well known in the art for the conversion of nitrogen heterocycles to their corresponding N-oxide derivatives, for example, hydrogen peroxide or an organic peracid such as m-chloroperbenzoic acid or peracetic acid. The oxidation is preferably carried out in a suitable conventional solvent or diluent for such oxidations, for example dichloromethane, chloroform or acetic acid, and at a temperature in the general range, for example 0° to 80° C.

Whereafter, when a non-toxic salt of a compound of formula I is required, it may be obtained, for example, by reaction with the appropriate base affording a physiologically acceptable cation, or with the appropriate acid affording a physiologically acceptable anion, or by any other conventional salt formation procedure.

Further, when an optically active form of a compound of formula I is required, one of the aforesaid processes may be carried out using an optically active starting material. Alternatively, the racemic form of a compound of formula I in which Z is an acidic group may be resolved, for example by reaction with an optically active form of a suitable organic base, for example, ephedrine, N,N,N-trimethyl-(1-phenylethyl)ammonium hydroxide or 1-phenylethylamine, followed by conventional separation of the diastereoisomeric mixture of salts thus obtained, for example by fractional crystallisation from a suitable solvent, for example a (1–4C)alkanol, whereafter the optically active form of said compound of formula I may be liberated by treatment with acid using a conventional procedure, for example using an aqueous mineral acid such as dilute hydrochloric acid.

Certain of the intermediates defined herein are novel, for example the compounds of the formula II, III, IV and IX, and are provided as a further feature of the invention.

As stated above, the compounds of formula I will have beneficial pharmacological effects in warm-blooded animals (including man) in diseases and medical conditions where amelioration of the vasoconstrictor and fluid retaining properties of the reninangiotensin-aldosterone system is desirable, at least in part by antagonism of one or more of the physiological actions of AII. The compounds of the invention will thus be useful in the treatment of diseases or medical conditions such as hypertension, congestive heart failure and/or hyperaldosteronism in warm-blooded animals (including man), as well as in other diseases or medical conditions in which the renin-angiotensin-aldosterone system plays a significant causative role.

The antagonism of one or more of the physiological actions of AII and, in particular, the antagonism of the interaction of AII with the receptors which mediate its effects on a target tissue, may be assessed using one or more of the following, routine laboratory procedures:

Test A: This in vitro procedure involves the incubation of the test compound initially at a concentration of 100 micromolar (or less) in a buffered mixture containing fixed concentrations of radiolabelled AII and a cell surface membrane fraction prepared from a suitable angiotensin target tissue. In this test, the source of cell surface membranes is the guinea pig adrenal gland which is well known to respond to AII. Interaction of the radiolabelled AII with its receptors (assessed as radiolabel bound to the particulate membrane fraction following removal of unbound radiolabel by a rapid filtration procedure such as is standard in such studies) is antagonized by compounds which also bind to the membrane receptor sites and the degree of antagonism (observed in the test as displacement of membrane-bound radioactivity) is determined readily by comparing the receptor-bound radioactivity in the presence of the test compound at the specified test concentration with a control value determined in the absence of the test compound. Using this procedure compounds showing at least 50% displacement of radiolabelled AII binding at a concentration of $10^{-4}$M are retested at lower concentrations to determine their potency. For determination of the $IC_{50}$ (concentration for 50% displacement of radiolabelled AII binding), concentrations of the test compound are ordinarily chosen to allow testing over at least four orders of magnitude centred about the predicted approximate $IC_{50}$, which latter is subsequently determined from a plot of percentage displacement against concentration of the test compound.

In general, acidic compounds of formula I as defined above show significant inhibition in Test A at a concentration of 50 micromolar or much less.

Test B: This in vitro test involves the measurement of the antagonistic effects of the test compound against AII-induced contractions of isolated rabbit aorta, maintained in a physiological salt solution at 37° C. In order to ensure that the effect of the compound is specific to antagonism of AII, the effect of the test compound on noradrenaline-induced contractions may also be determined in the same preparation.

In general, acidic compounds of formula I as defined above show significant inhibition in Test B at a final concentration of 50 micromolar or much less. [Note: Compounds of formula I wherein Z is a group of the formula —CO.OR$^8$ in which R$^8$ is other than hydrogen in general show only weak activity in the in vitro Tests A or B.]

Test C: This in vivo test involves using terminally-anaesthetised or conscious rats in which an arterial catheter has been implanted under anaesthesia for the measurement of changes in blood pressure. The AII antagonistic effects of the test compound following oral or parenteral administration, are assessed against angiotensin II-induced pressor responses. To ensure that the effect is specific, the effect of the test compound on vasopressin-induced pressor responses may also be determined in the same preparation.

The compounds of formula I generally show specific AII-antagonist properties in Test C at a dose of 50 mg/kg body weight or much less, without any overt toxicological or other untoward pharmacological effect.

Test D: This in vivo involves the stimulation of endogenous AII biosynthesis in a variety of species including rat, marmoset and dog by introducing a diet of low sodium content and giving appropriate daily doses of a saluretic known as frusemide. The test compound is then administered orally or parenterally to the animal in which an arterial catheter has been implanted under anaesthesia for the measurement of changes in blood pressure.

In general compounds of formula I will show AII-antagonist properties in Test D as demonstrated by a significant reduction in blood pressure at a dose of 50 mg/kg body weight or much less, without any overt toxicological or other untoward pharmacological effect.

By way of illustration of the angiotensin II inhibitory properties of compounds of formula I, the compound of Example 2 gave the following results in tests A and C described above:

In test A: an $IC_{50}$ of $5 \times 10^{-8}M$;

In test C: $ED_{50}$ of 0.1 mg/kg (i.v. administration).

The compounds of formula I will generally be administered for therapeutic or prophylactic purposes to warm-blooded animals (including man) requiring such treatment in the form of a pharmaceutical composition, as is well known in the pharmaceutical art. According to a further feature of the invention there is provided a pharmaceutical composition comprising a compound of formula I, or a salt or N-oxide thereof as defined above, together with a pharmaceutically acceptable diluent or carrier. Such compositions will conveniently be in a form suitable for oral administration (e.g. as a tablet, capsule, solution, suspension or emulsion) or parenteral administration (e.g. as an injectable aqueous or oily solution, or injectable emulsion).

The compounds of formula I may also be advantageously administered for therapeutic or prophylactic purposes together with another pharmacological agent known in the general art to be of value in treating one or more of the diseases or medical conditions referred to hereinabove.

In general a compound of formula I (or a pharmaceutically acceptable salt thereof as appropriate) will generally be administered to man so that, for example, a daily oral dose of up to 50 mg/kg body weight (and preferably of up to 10 mg/kg) or a daily parenteral dose of up to 5 mg/kg body weight (and preferably of up to 1 mg/kg) is received, given in divided doses as necessary, the precise amount of compound (or salt) administered and the route and form of administration depending on size, age and sex of the person being treated and on the particular disease or medical condition being treated according to principles well known in the medical arts.

In addition to their aforesaid use in therapeutic medicine in humans, the compounds of formula I are also useful in the veterinary treatment of similar conditions affecting commercially valuable warm-blooded animals, such as dogs, cats, horses and cattle. In general for such treatment, the compounds of the formula I will generally be administered in an analogous amount and manner to those described above for administration to humans. The compounds of formula I are also of value as pharmacological tools in the development and standardisation of test systems for the evaluation of the effects of AII in laboratory animals such as cats, dogs, rabbits, monkeys, rats and mice, as part of the continuing search for new and improved therapeutic agents.

The invention will now be illustrated by the following non-limiting Examples in which, unless otherwise stated:

(i) concentrations and evaporations were carried out by rotary evaporation in vacuo;

(ii) operations were carried out at room temperature, that is in the range 18°-26° C.;

(iii) flash column chromatography was performed on Merck Kieselgel 60 (Art. no. 9385) obtained from E Merck, Darmstadt, Germany;

(iv) yields, where given, are intended for the assistance of the reader only and are not necessarily the maximum attainable by diligent process development;

(v) $^1H$ NMR spectra were normally determined at 200 MHz in $CDCl_3$ using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d,doublet;

(vi) $^{13}C$ NMR spectra were normally determined at 100 MHz in $CDCl_3$ or $d_6$-dimethylsulphoxide ($d_6$-DMSO) using the solvent signal as internal standard, and are expressed as chemical shifts (delta values) in parts per million relative to TMS;

(vii) all end-products had satisfactory microanalyses; and (viii) the term "1H-tetrazol-5-yl" stands for "1H-1,2,3,4-tetrazol-5-yl".

EXAMPLE 1

6M Hydrochloric acid (10 ml) was added to a solution of ethyl 2,6-dimethyl-4-[(2'-(2-triphenylmethyl-2H-tetrazol-5-yl)biphenyl-4-yl)methoxy]pyridine-3-carboxylate (A) (600 mg) in dioxane (15 ml) and the mixture was stirred for 3 hours. Volatile material was removed by evaporation and the residue stirred for 30 minutes in a mixture of ethanol and ether (1:3 v/v, 20 ml). The insoluble solid was collected by filtration and recrystallised from a mixture of ethanol and methanol (1:1 v/v) to give ethyl 2,6-dimethyl-4-[(2'-(1H-tetrazol-5-yl)biphenyl-4-yl)methoxy]pyridine-3-carboxylate hydrochloride (270 mg), as a white powder, m.p. 205° C; NMR ($d_6$-DMSO, $d_4$-acetic acid): 1.2(t,3H), 2.6(s,3H), 2.7(s,3H), 4.4(q,2H), 5.5(s,2H), 7.2(d,2H), 7.4(d,2H), 7.55-7.65(m,3H), 7.67-7.75(m,2H); mass spectrum [negative fast atom bombardment (−ve FAB), DMSO/glycerol (GLY)]: 428 $(M-H)^-$, 234, 194; microanalysis, found: C,61.7; H,5.0; N,14.9%; $C_{23}H_{24}N_5O_3 \cdot HCl$ requires: C,61.9; H,5.2; N,15.0%.

The starting material (A) was obtained as follows:

Sodium hydride (60% dispersion in mineral oil; 206 mg) was added to a stirred solution of ethyl 1,4-dihydro-2,6-dimethyl-4-oxopyridine-3-carboxylate (1.0 g) (obtained as described in *Monatshefte fur Chemie.*, 1969, 100, 132) in N,N-dimethylformamide (DMF) (25 ml). The mixture was stirred at 50° C. until evolution of hydrogen ceased and then 5-[2-(4'-bromomethylbiphenylyl)]-2-triphenylmethyl-2H-tetrazole (2.86 g) (obtained as described in European patent 0291969) was added. The solution was stirred at 50° C. for 30 minutes and then at ambient temperature for 72 hours. The solvent was removed by evaporation and the residue partitioned between ethyl acetate (30 ml) and water (30 ml). The organic layer was separated, washed with saturated sodium chloride solution (30 ml) and dried ($MgSO_4$). The solvent was removed by evaporation and the residue purified by flash chromatography, eluting with ethyl acetate/hexane (1:1 v/v gradually changing to 9:1 v/v) to give ethyl 2,6-dimethyl-4-[(2'-(2-triphenymethyl-2H-tetrazol-5-yl)biphenyl-4-yl)methoxy]-pyridine-3-carboxylate (A) (2.38 g), as a foam; NMR ($d_6$-DMSO, $d_4$-acetic acid): 1.2(t,3H), 2.4(s,3H), 2.45(s,3H), 4.3(q,2H), 5.2(s,2H), 6.85-6.95(m,6H), 7.0(s,1H), 7.15(d,2H), 7.25-7.4 (complex m,11H), 7.45-7.75 (complex m,3H), 7.85(dd,1H); $^{13}C$ NMR ($d_6$-DMSO): 69.0 (benzylic $CH_2$).

EXAMPLES 2-6

Using an analogous procedure to that described in Example 1, but starting from the appropriate compound of formula III wherein L is triphenylmethyl, the following compounds of formula I were obtained in yields of 50–80%:

(Example 2): methyl 2,6-dimethyl-4-[(2'-(1H-tetrazol-5-yl)biphenyl-4-yl)methoxy]pyridine-3-carboxylate hydrochloride, m.p. 137°–140° C.; NMR (d$_6$-DMSO, d$_4$-acetic acid): 2.6(s,3H), 2.7(s,3H), 3.9(s,3H), 5.4(s,2H), 7.2(d,2H), 7.4(d,2H), 7.45–7.75 (complex m,5H); mass spectrum (−ve FAB, DMSO/GLY): 414 (M−H)⁻, 234; microanalysis, found: C,58.9; H,4.8; N,14.8%; C$_{23}$H$_{21}$N$_5$O$_3$.HCl.H$_2$O requires: C58.8; H,5.1; N,14.9%;

(Example 3): 2,6-dimethyl-4-[(2'-(1H-tetrazol-5-yl)biphenyl-4-yl)methoxy]pyridine hydrochloride, m.p. 225° C.; NMR (d$_6$-DMSO, d$_4$-acetic acid): 2.6(s,6H), 5.4(s,2H), 7.2(d,2H), 7.3(s,2H), 7.45(d,2H), 7.55–7.8 (complex m,4H); mass spectrum (−ve FAB, DMSO/GLY): 356 (M−H)⁻, 234, 122; microanalysis, found: C,63.7; N,5.2; N,18.0%; C$_{21}$H$_{19}$N$_5$O.HCl requires: C,64.2; H,4.8; N,17.8%;

(Example 4): 2-methyl-5,6,7,8-tetrahydro-4-[(2'-(1H-tetrazol-5-yl)biphenyl-4-yl)methoxy]quinoline hydrochloride, m.p. 222°–223° C.; NMR (d$_6$-DMSO): 1.7–1.9(m,4H), 2.55–2.7(m,2H), 2.7(s,3H), 2.95–3.05(m,2H), 5.4(s,2H), 7.2(d,2H), 7.4(d,2H), 7.45(s,1H), 7.5–7.8 (complex m,4H), 12.9(br,1H); mass spectrum (−ve FAB, DMSO/GLY): 396 (M−H)⁻, 234, 162; microanalysis, found: C,65.9; H,5.7; N,16.0%; H$_2$O, 0.3%; C$_{24}$H$_{23}$N$_5$O.HCl.0.13H$_2$O requires: C,66.0; H,5.6; N,16.1; H$_2$O, 0.6%;

(Example 5): 2-ethyl-5,6,7,8-tetrahydro-4-[(2'-(1H-tetrazol-5-yl)biphenyl-4-yl)methoxy]quinoline hydrochloride, m.p. 232°–233° C.; NMR (d$_6$-DMSO): 1.3(t,3H), 1.7–1.9(m,4H), 2.6–2.7(m,2H), 2.9–3.0(m,4H), 5.5(s,2H), 7.2(d,2H), 7.4(s,1H), 7.45(d,2H), 7.55–7.8 (complex m,4H); mass spectrum (−ve FAB, DMSO/GLY): 410 (M−H)⁻, 234, 176; microanalysis, found: C,66.9; H,6.0; N,15.8%; Cl,8.2%; C$_{25}$H$_{25}$N$_5$O.HCl requires: C,67.0; H,5.9; N,15.6%; Cl,7.9%; and (Example 6): 6,7-dihydro-2-methyl-4-[(2'-(1H-tetrazol-5-yl)biphenyl-4-yl)methoxy]-5H-cyclopenta[b]pyridine hydrochloride, m.p. 210°–212° C.; NMR (d$_6$-DMSO): 2.1–2.3(m,2H), 2.65(s,3H), 2.9(t,2H), 3.2(m,2H), 5.4(s,2H), 7.2(d,2H), 7.4(d,2H), 7.45(s,1H), 7.55–7.75 (complex m,4H); mass spectrum (−ve FAB, DMSO/GLY): 382 (M−H)⁻, 234, 148; microanalysis, found: C,65.7; H,5.4; N,16.8%; C$_{23}$H$_{21}$N$_5$O.HCl requires C,65.8; H,5.3; N,16.8%.

The necessary starting materials of formula III used in Examples 2–6, corresponding to starting material A in Example 1, were obtained in yields of 50–70% using an analogous procedure to that described in Example 1 as follows:

(Example 2A): methyl 2,6-dimethyl-4-[(2'-(2-triphenylmethyl-2H-tetrazol-5-yl)biphenyl-4-yl)methoxy]pyridine-3-carboxylate, isolated as a foam: NMR (d$_6$-DMSO, d$_4$-acetic acid): 2.4(s,3H), 2.45(s,3H), 3.7(s,3H), 5.1(s,2H), 6.9(dd,6H), 7.0(s,1H), 7.05(d,2H), 7.15–7.3 (complex m,11H), 7.6–7.8 (complex m,3H), 7.8(dd,1H); starting from methyl 1,4-dihydro-2,6-dimethyl-4-oxopyridine-3-carboxylate, itself obtained as a solid, m.p. 218°–219° C., from methyl 3-aminocrotonate and diketene using an analogous procedure to that described in Monatshefte fur Chemie, 1969, 100, 132 for the preparation of ethyl 1,4-dihydro-2,6-dimethyl-4-oxopyridine-3-carboxylate.

(Example 3A): 2,6-dimethyl-4-[(2'-(2-triphenylmethyl-2H-tetrazol-5-yl)biphenyl-4-yl)methoxy]pyridine, isolated as a foam: NMR (d$_6$-DMSO, d$_4$-acetic acid): 2.5(s,6H), 5.2(s,2H), 6.85–6.95(m,6H), 7.0(s,2H), 7.15(d,2H), 7.25–7.4 (complex m,11H), 7.45–7.7 (complex m,3H), 7.85(dd,1H); starting from 2,6-dimethyl-4(1H)-pyridone, itself obtained as described in J. Chem. Soc. (B), 1968, 866.

(Example 4A): 2-methyl-5,6,7,8-tetrahydro-4-[(2'-(2-triphenylmethyl-2H-tetrazol-5-yl)biphenyl-4-yl)methoxy]quinoline, m.p. 156°–156.5° C.; NMR (d$_6$-DMSO): 1.6–1.85 (complex m,4H), 2.4(s,3H), 2.55–2.65(m,2H), 2.65–2.75(m,3H), 5.1(s,3H), 6.7(s,1H), 6.9(dd,6H), 7.1(d,2H), 7.2–7.4 (complex m,11H), 7.4–7.65 (complex m,3H), 7.8(dd,1H); starting from 2-methyl-5,6,7,8-tetrahydro-4(1H)-quinolone, itself obtained as described in Liebigs. Ann. Chem., 1982, 1656.

(Example 5A): 2-ethyl-5,6,7,8-tetrahydro-4-[(2'-(2-triphenylmethyl-2H-tetrazol-5-yl)biphenyl-4-yl)methoxy]quinoline, m.p. 111°–115° C.; NMR (d$_6$-DMSO): 1.2(t,3H), 1.6–1.8(m,4H), 2.5–2.8 (complex m,6H), 5.1(s,2H), 6.75(s,1H), 6.8–6.9(m,6H), 7.1(d,2H), 7.25–7.4 (complex m,11H), 7.45–7.7 (complex m,3H), 7.8(dd,1H); starting from a 9:1 w/w mixture of 2-ethyl-5,6,7,8-tetrahydro-4(1H)-quinolene and 2-ethyl-4(1H)-quinolone [obtained using an analogous procedure to that described for the preparation of 2-methyl-5,6,7,8-tetrahydro-4(1H)-quinolone in Liebigs Ann. Chem., 1982, 1656 but starting from 2-ethyl-4(1H)-quinolone] and purifying by flash chromatography eluting with ethyl acetate/hexane (1:1 v/v).

(Example 6A): 6,7-dihydro-2-methyl-4-[(2'-(2-triphenylmethyl-2H-tetrazol-5-yl)biphenyl-4-yl)methoxy]-5H-cyclopenta[b]pyridine, isolated as a foam; NMR (d$_6$-DMSO): 1.9–2.1(m,2H), 2.4(s,3H), 2.7(t,2H), 2.8(t,2H), 5.1(s,2H), 6.75(s,1H), 6.8–6.9(m,6H), 7.1(d,2H), 7.25–7.4 (complex m,11H), 7.45–7.7 (complex m,3H), 7.8(dd,1H); starting from an 85:15 w/w mixture of 2-methyl-1,5,6,7-tetrahydro-4(1H)-cyclopenta[b]pyridone and 3-methoxycarbonyl-2-methyl-1,5,6,7-tetrahydro-4(1H)-cyclopenta[b]pyridone [obtained using an analogous procedure to that described in Heterocycles, 1982, 13, 239] and purifying by flash chromatography using ethyl acetate as eluant.

EXAMPLE 7

A solution of ethyl 2,6-dimethyl-4-[(2'-(1H-tetrazol-5-yl)biphenyl-4-yl)methoxy]pyridine-3-carboxylate hydrochloride (240 mg) in 2M aqueous sodium hydroxide (5 ml) was heated under reflux for 2 hours. The solution was cooled and acidified to pH 3 with 6M hydrochloric acid. The precipitated solid was collected by filtration and triturated with hot methanol to give 2,6-dimethyl-4-[(2'-(1H-tetrazol-5-yl)biphenyl-4-yl)methoxy]pyridine-3-carboxylic acid (67 mg), as a white powder, m.p. 237° C.; NMR (d$_6$-DMSO, d$_4$-acetic acid): 2.45(s,3H), 2.55(s,3H), 5.3(s,2H), 7.1(s,1H), 7.2(d,2H), 7.4(d,2H), 7.4–7.75 (complex m,4H); mass specturm (DMSO/GLY): 400 (M−H)⁻, 166; microanalysis, found: C,64.5; H,4.5; N,17.0%; C$_{22}$H$_{19}$N$_5$O$_3$.0.5H$_2$O requires: C,64.5; H,4.9; N,17.1%.

EXAMPLE 8

Using an analogous procedure to that described in Example 1, but starting from 2,6-dimethyl-3-hydroxymethyl-4-[(2'-(2-triphenylmethyl-2H-tetrazol-5-yl)biphenyl-4-yl)methoxy]pyridine (A) there was thus obtained 2,6-dimethyl-3-hydroxymethyl-4-[(2'-(1H-tetrazol-5-yl)biphenyl-4-yl)methoxy]pyridine hydrochloride, as a solid, m.p. 224° C.; NMR (d$_6$-DMSO, d$_4$- acetic acid): 2.55(s,3H), 2.6(s,3H), 4.6(s,2H), 5.4(s,2H), 7.2(d,2H), 7.45(s+d, 3H), 7.55-7.65(m,2H), 7.6-7.65(m,2H); mass specturm (DMSO/GLY): 386 (M−H)⁻; microanalysis, found: C,60.9; H,4.9; N,15.8%; $C_{22}H_{21}N_5O_2.HCl.0.5H_2O.0.1C_2H_5OH$ requires: C,60.5; H,5.3; N,16.0%.

The starting material (A) was obtained as follows:

Lithium borohydride (66 mg) was added over a period of 10 minutes to a solution of ethyl 2,6-dimethyl-4-[(2'-(2-triphenylmethyl-2H-tetrazol-5-yl)biphenyl-4-yl)methoxy]pyridine-3-carboxylate (800 mg) in tetrahydrofuran (THF) (25 ml) stirred at 0° C. under an atmosphere of argon. The solution was then stirred at ambient temperature for 16 hours, cooled to 0° C. and water (100 ml) was added. The mixture was extracted with dichloromethane (2×50 ml) and the extracts were washed with saturated sodium chloride solution (50 ml) and dried (MgSO₄). The solvent was removed by evaporation and the residue purified by flash chromatography, eluting with methanol/dichloromethane (1:19 v/v), to give 2,6-dimethyl-3-hydroxymethyl-4-[(2'-(2-triphenylmethyl-2H-tetrazol-5-yl)biphenyl-4-yl)methoxy]pyridine (A) (246 mg), as a foam; NMR (d₆-DMSO, d₄-acetic acid): 2.55(s,3H), 2.65(s,3H), 4.7(s,2H), 5.4(s,2H), 6.9-7.0(m,6H), 7.2(d,2H), 7.25-7.45 (complex m,12H), 7.45-7.8 (complex m,3H), 7.9(dd,1H).

EXAMPLES 9-14

Using an analogous procedure to that described in Example 1, but starting from the appropriate compound of formula III wherein L is triphenylmethyl, the following compounds of formula I were obtained in yields of 76-91%

(Example 9): methyl 2-ethyl-6-methyl-4-[(2'-(1H-tetrazol-5-yl)biphenyl-4-yl)methoxy]pyridine-3-carboxylate hydrochloride, m.p. 189°-190° C.; NMR (d₆-DMSO/d₄-acetic acid): 1.3(t,3H), 2.7(s,3H), 2.9(q,2H), 3.9(s,3H), 5.5(s,2H), 7.2(d,2H), 7.4(d,2H), 7.55-7.8 (complex m,5H); mass spectrum (positive fast atom bombardment (+ve FAB), DMSO/nitrobenzyl alcohol): 859(2M+H)⁺, 430(M+H)⁺; microanalysis, found: C,61.8; H,4.9; N,14.9%; $C_{24}H_{23}N_5O_3.HCl$ requires: C,61.9; H,5.2; N,15.0%.

(Example 10): methyl 6-ethyl-2-methyl-4-[(2'-(1H-tetrazol-5-yl)biphenyl-4-yl)methoxy]pyridine-3-carboxylate hydrochloride, m.p. 152°-154° C.; NMR (d₆-DMSO/d₄-acetic acid): 1.35(t,3H), 2.6(s,3H), 3.0(q,2H), 3.9(s,3H), 5.5(s,2H), 7.2(d,2H), 7.4(d,2H), 7.5-7.8 (complex m, 5H); mass spectrum (+ve FAB, DMSO/m-nitrobenzyl alcohol): 430(M+H)⁺; microanalysis, found: C,61.6; H,5.4; N,14.6%; $C_{24}H_{23}N_5O_3.HCl$ requires: C,61.9; H,5.2; N,15.0%;

(Example 11): methyl 2,6-diethyl-4-[(2'-(1H-tetrazol-5-yl)biphenyl-4-yl)methoxy]pyridine-3-carboxylate hydrochloride, m.p. 174°-175° C.: NMR (d₆-DMSO)/d₄-acetic acid): 1.2-1.4(m,6H), 2.85-3.1(m,4H), 3.9(s,3H), 5.5(s,2H), 7.2(d,2H), 7.4(d,2H), 7.55-7.8 (complex m,5H); mass spectrum (+ve FAB, DMSO/m-nitrobenzyl alcohol): 444(M+H)⁺; microanalysis, found: C,62.0; H,5.4; N,14.4%; $C_{25}H_{25}N_5O_3.HCl$ requires: C,62.3; H,5.4; 14.5%;

(Example 12): 6,7-dihydro-2-ethyl-4-[(2'-(1H-tetrazol-5-yl)biphenyl-4-yl)methoxy]-5H-cyclopenta[b]pyridine hydrochloride, m.p. 212°-214° C. (decomposition); NMR (d₆-DMSO): 1.3(t,3H), 2.1-2.3(m,2H), 2.8-3.0(m,4H), 3.2(t,2H), 5.45(s,2H), 7.2(d,2H), 7.4-7.5(m,3H), 7.5-7.75(m,4H); mass spectrum (+ve FAB, DMSO/m-nitrobenzyl alcohol); 398(M+H)⁺; microanalysis, found: C,66.0; H,5.9; N,16.0%; $C_{24}H_{23}N_5O.HCl$ requires: C,66.4; H,5.5; N,16.2%;

(Example 13): 2,6-dimethyl-3-phenyl-4-[(2'-(1H-tetrazol-5-yl)biphenyl-4-yl)methoxy]pyridine hydrochloride, m.p. 144° C. (decomposition); NMR (d₆-DMSO/d₄-acetic acid): 2.4(s,3H), 2.7(s,3H), 5.4(s,2H), 7.1(d,2H), 7.2(d,2H), 7.3-7.4(m,2H), 7.4-7.8(complex m,8H); mass spectrum (+ve FAB, DMSO/m-nitrobenzyl alcohol): 868(2M+H)⁺, 434(M+H)⁺; microanalysis, found: C,66.9; H,6.0; N,13.3; H₂O,2.0%; $C_{27}H_{23}N_5O.HCl.0.5Et_2O.0.53H_2O$ requires: C,67.3; H,5.8; N,13.5%; H₂O,1.9%.

(Example 14): allyl 2,6-dimethyl-4-[(2'-(1H-tetrazol-5-yl)biphenyl-4-yl)methoxy]pyridine-3-carboxylate hydrochloride, m.p. 177°-179° C.; NMR (d₆-DMSO): 2.6(s,3H), 2.7(s,3H), 4.8-4.85(d,2H), 5.2-5.4(m,2H), 5.45(s,2H), 5.8-6.0(m,1H), 7.1-7.2(d,2H), 7.3-7.9(d,2H), 7.5-7.8(complex m,5H); mass spectrum (+ve FAB, DMSO/nitrobenzyl alcohol): 442 (M+H)⁺.

The necessary starting materials of formula III used in Examples 9-14, corresponding to starting material A in Example 1, were obtained in yields of 63-81% using an analogous procedure to that described in Example 1 as follows:

(Example 9A): methyl 2-ethyl-6-methyl-4-[(2'-(2-triphenylmethyl-2H-tetrazol-5-yl)biphenyl-4-yl)methoxy]pyridine-3-carboxylate, m.p. 157°-158° C. (decomposition); NMR (CDCl₃): 1.3(t,3H), 2.5(s,3H), 2.8(q,2H), 3.85(s,3H), 5.0(s,2H), 6.6(s,1H), 6.85-7.0 (complex m,6H), 7.15(s,4H), 7.2-7.5 (complex m,12H), 7.9-8.0(m,1H); mass spectrum (+ve FAB, DMSO/m-nitrobenzyl alcohol): 672(M+H)⁺; starting from methyl 1,4-dihydro-2-ethyl-6-methyl-4-oxopyridine-3-carboxylate, itself obtained as a solid m.p. 148°-150° C.; NMR (CDCl₃): 1.25(t,3H), 2.3(s,3H), 2.7(q,2H), 3.8(s,3H), 6.7(s,1H); mass spectrum (chemical ionisation, ammonia): 196(M+H)⁺, from methyl 3-amino-2-pentenoate and diketene using an analogous procedure to that described in Example 2A.

(Example 10A): methyl 6-ethyl-2-methyl-4-[(2'-(2-triphenylmethyl-2H-tetrazol-5-yl)biphenyl-4-yl)methoxy]pyridine-3-carboxylate, m.p. 67°-70° C.; NMR (CDCl₃): 1.25(t,3H), 2.5(s,3H), 2.75(q,2H), 3.85(s,3H), 5.05(s,2H), 6.1(s,1H), 6.9-7.0(complex m,6H), 7.1-7.5-(complex m,22H), 7.9-8.0(m,1H); mass spectrum (+ve FAB, DMSO/m-nitrobenzyl alcohol): 672(M+H)⁺; starting from methyl 1,4-dihydro-6-ethyl-2-methyl-4-oxopyridine-3-carboxylate itself obtained as follows:

A mixture of methyl 3-aminocrotonate (5 g) and 5-(1-hydroxypropylidene)-2,2-dimethyl-1,3-dioxane-4,6-dione (10 g) (obtained as described in J. Org. Chem., 1978, 43, 2087) was heated at 120° C. for 1 hour. The residue was cooled to ambient temperature and treated with a mixture of ether and hexane (1:6 v/v; 35 ml) and allowed to stand for 18 hours. The solvent was removed by decanting and the insoluble residue purified by flash chromatography, eluting with methanol/dichloromethane (1:9 v/v) to give methyl 1,4-dihydro-6-ethyl-2-methyl-4-oxopyridine-3-carboxylate (1 g), as a yellow solid, m.p. 176°-180° C.; NMR (CDCl₃): 1.2(t,3H); 2.45(s,3H), 2.45(q,2H), 3.8(s,3H), 6.3(s,1H); mass spectrum (chemical ionisation, ammonia): 196(M+H)⁺.

(Example 11A): methyl 2,6-diethyl-4-[2'-(2-triphenylmethyl-2H-tetrazol-5-yl)biphenyl-4-yl)methoxy[pyridine-3-carboxylate, m.p. 59°-64° C.; NMR (CDCl₃): 1.2-1.4(m,6H), 2.5-2.9(m,4H), 3.85(s,3H), 5.05(s,2H), 6.6(s,1H), 6.9-7.0(complex m,6H), 7.1-7.55(complex m,16H), 7.9–8.0(m,1H); mass spectrum (+ve FAB, DMSO/m-nitrobenzyl alcohol): 686(M+H)+; starting from methyl 2,6-diethyl-1,4-dihydro-4-oxopyridine-3-carboxylate, itself obtained as a solid m.p. 127°–130° C.; NMR (CDCl₃): 1.2–1.35(m,6H), 2.4–2.9(m,4H), 3.8(s,3H), 6.3(s,1H); mass spectrum (chemical ionisation, ammonia): 210(M+H)+; starting from methyl 3-amino-2-pentenoate and 5-(1-hydroxypropylidine)-2,2-dimethyl-1,3-dioxane-4,6-dione using an analogous procedure to that described in Example 10A.

(Example 12A): 6,7-dihydro-2-ethyl-4-[(2'-(2-triphenylmethyl-2H-tetrazol-5-yl)biphenyl-4-yl)methoxy]-5H-cyclopenta[b]pyridine, as an amorphous solid; NMR (d₆-DMSO): 1.19(t,3H), 1.92–2.08(m,2H), 2.57–2.77(m,4H), 2.84(t,2H), 5.13(s,2H), 6.77(s,1H), 6.83–6.92(complex m,6H), 7.11(d,2H), 7.25–7.40(complex m,11H), 7.43–7.68(m,3H), 7.82(dd,1H); microanalysis, found: C,79.7; H,5.6; N,10.8%; C₄₃H₃₇N₅O.0.33DMF requires: C,79.6; H,5.9; N,11.3%; starting from 2-ethyl-1,5,6,7-tetrahydro-4-(1H)-cyclpenta[b]pyridone itself obtained as follows:

A mixture of 4-(1-cyclopenten-1-yl)morpholine (7.7 g) and 5-(1-hydroxypropylidine-2,2-dimethyl-1,3-dioxane-4,6-dione (20 g) [obtained as described in *J. Org. Chem.*, 1978, 43, 2087] was heated at 120° C. for 1 hour. The residue was cooled to ambient temperature and purified by flash chromatography, eluting with methanol/dichloromethane (1:19 v/v), to give a mixture of 6,7-dihydro-2-ethylcyclopenta[b]pyran-4(5H)-one and 4-(1,3-dioxobutyl)morpholine. The mixture was treated with concentrated ammonia solution (150 ml) at 120° C. for 15 hours and then cooled to ambient temperature. Volatile material was removed by evaporation and the residue was partitioned between ether/ethyl acetate (1:1 v/v, 300 ml) and 2M sodium hydroxide solution (200 ml). The aqueous layer was separated, acidified to pH6 with concentrated hydrochloric acid and extracted with ethyl acetate (3×100 ml) and then chloroform (3×100 ml). The organic extracts were washed with satured sodium chloride solution (1×50 ml) and dried (MgSO₄). Solvent was removed by evaporation and the combined residues purified by flash chromatography, eluting with ethyl acetate/methanol (1:9 v/v) to give 2-ethyl-1,5,6,7-tetrahydro-4(1H)-cyclopenta[b]pyridone (2.2 g), as a pale yellow solid, m.p. 212°–214° C. (decomposition); NMR (d₆-DMSO): 1.5(t,3H), 1.88–2.04(m,2H), 2.35–2.60(m,4H), 2.78(t,2H), 11.33(bs,1H); mass spectrum (chemical ionisation, ammonia): 164(M+H)+.

(Example 13A): 2,6-dimethyl-3-phenyl-4-[(2'-triphenylmethyl-2H-tetrazol-5-yl)biphenyl-4-yl)methoxy]pyridine, m.p. 82°–84° C.; NMR (CDCl₃): 2.3(s,3H), 2.5(s,3H), 4.95(s,2H), 6.6(s,1H), 6.9(complex m,8H), 7.05(d,2H), 7.1–7.5(complex m,17H), 7.9(m,1H); mass spectrum (+ve FAB, DMSO/m-nitrobenzyl alcohol): 676(M+H)+; starting from 2,6-dimethyl-3-phenyl-4(1H)-pyridone itself obtained as a solid m.p. 231°–235° C. (decomposition); NMR (CDCl₃/d₆-DMSO): 2.1(s,3H), 2.3(s,3H), 6.2(s,1H), 7.1–7.5(complex m,5H); mass spectrum (electron impact ionisation): 199(M)+, 170, 128, 115; from 2,6-dimethyl-3-phenyl-4H-pyran-4-one and ammonia using an analogous procedure to that described in *J. Am. Chem. Soc.*, 1974, 96 (4), 1152.

(Example 14A): allyl 2,6-dimethyl-4-[(2'-(2-triphenylmethyl-2H-tetrazol-5-yl)biphenyl-4-yl)methoxy]pyridine-3-carboxylate, m.p. 65°–70° C. (decomposition); NMR (d₆-DMSO): 2.3–2.4(2 x s,6H), 4.7–4.8(m,2H), 5.1–5.4(m,4H), 5.8–6.0(m,1H), 6.8–7.85(complex m,24H); mass spectrum (+ve FAB, DMSO/m-nitrobenzyl alcohol): 684(M+H)+; starting from allyl 1,4-dihydro-2,6-dimethyl-4-oxopyridine-3-carboxylate, itself obtained as a solid m.p. 139°–141° C.; NMR (d6-DMSO); 2.1–2.25(s,6H), 4.65–4.75(s,2H), 5.2–5.5(m,2H), 5.8–6.1(m,2H), 11.2–11.4(br s,1H); starting from allyl 3-aminocrotonate and diketene using an analogous procedure to that described in Example 2A.

EXAMPLE 15

Using an analogous procedure to that described in Example 1, but starting from methyl 2-chloro-6-methyl-4-[2'-(2-triphenylmethyl-2H-tetrazol-5-yl)biphenyl-4-yl)methoxy]pyridine-3-carboxylate (A), there was obtained in 50% yield methyl 2-chloro-6-methyl-4-[(2'-(1H-tetrazol-5-yl)biphenyl-4-yl)methoxy]pyridine-3-carboxylate, as a white powder, m.p. 204°–207° C.; NMR (d₆-DMSO, d₄-acetic acid): 2.45(s,3H), 3.85(s,3H), 5.3(s,2H), 7.2–7.8 (complex m,9H); mass spectrum (+ve FAB, DMSO/m-nitrobenzyl alcohol): 436 (M+H)+;

The starting material (A) was obtained as follows:

(i) Powdered potassium acetate (17.5 g) was added to a solution of 5-[2-(4'-bromomethylbiphenylyl)]-2-triphenylmethyl-2H-tetrazole (50 g) (obtained as described in European Patent Application, Publication No. 0291969) and 1,4,7,10,13,16-hexaoxacyclooctadecane (100 mg) in 1,2-dimethoxyethane (DME) (600 ml), and the mixture was heated under reflux for 20 hours. Insoluble material was removed by filtration, and the residue was triturated with a mixture of ethyl acetate and hexane (1:4 v/v) to give 5-[2-(4'-acetoxymethylbiphenylyl)]-2-triphenylmethyl-2H-tetrazole (B) (41.8 g), as a cream powder, m.p. 119°–121° C.; NMR (CDCl₃): 2.1(s,3H), 5.0(s,2H), 6.8–6.95 (complex m,8H), 7.2–7.55 (complex m,14H), 7.9–8.0(m,1H).

(ii) A solution of compound (B) (41.8 g) in THF (200 ml) was added over a period of 40 minutes to a suspension of lithium borohydride (4.1 g) in THF (400 ml) stirred at 0° C. under an atmosphere of argon. The mixture was stirred at ambient temperature for 20 hours and then cooled to 0° C. 20% Aqueous citric acid solution (40 ml) was added and the mixture was diluted with saturated sodium chloride solution (600 ml). The mixture was extracted with ethyl acetate (2×500 ml) and the extracts were washed with water (500 ml) and saturated sodium chloride solution (500 ml). The combined extracts were dried (MgSO₄) and volatile material removed by evaporation. The residue was purified by flash chromatography, eluting with ethyl acetate/hexane (2:3 v/v), to give 5-[2-(4'-hydroxymethylbiphenylyl)]-2-triphenylmethyl-2H-tetrazole (C) (17.4 g), as a white solid, m.p. 168°–169° C. (after recrystallisation from a mixture of ethyl acetate and hexane (1:9 v/v)); NMR (CDCl₃): 4.6(s,2H), 6.85–7.0(m,6H), 7.2–7.5 (complex m,16H), 7.9–8.0(m,1H).

(iii) A mixture of compound (C) (1.58 g), methyl 2,4-dichloro-6-methylpyridine-3-carboxylate (700 mg) (obtained as described in *Synthesis*, 1988, 479), potassium tert-butoxide (400 mg), potassium fluoride (10 mg) and 1,4,7,10,13,16-hexaoxacyclooctadecane (10 mg) in acetonitrile (5 ml) was heated at 60° C. for 24 hours. Volatile material was removed by evaporation and the residue was partitioned between water (20 ml) and dichloromethane (20 ml). The organic phase was separated, washed with saturated sodium chloride solution (20 ml) and then dried (MgSO₄). Volatile material was removed by evaporation and the residue was purified by flash chromatography, eluting with ethyl acetate, to give methyl 2-chloro-6-methyl-4-[(2'-(2-triphenylmethyl-2H-tetrazol-5-yl)biphenyl-4-yl)methoxy]pyridine-3-carboxylate (A) (1.26 g), as a foam; NMR (CDCl$_3$): 2.45(s,3H), 3.9(s,3H), 5.05(s,2H), 6.6–7.95 (complex m,24H).

EXAMPLES 16–22

Using an analogous procedure to that described in Example 1, but starting from the appropriate compound of formula III wherein L is triphenylmethyl, the following compounds of formula I were obtained in yields of 75–91%

(Example 16): methyl 2-methoxymethyl-6-methyl-4-[(2'-(1H-tetrazol-5-yl)biphenyl-4-yl)methoxy]pyridine-3-carboxylate hydrochloride, m.p. 168°–169° C.; NMR (d$_6$-DMSO/d$_4$-acetic acid): 2.7(s,3H), 3.4(s,3H), 3.85(s,3H), 4.7(s,2H), 5.5(s,2H), 7.2(d,2H), 7.4(d,2H), 7.5–7.8 (complex m,5H); mass spectrum (+ve FAB, DMSO/m-nitrobenzyl alcohol): 446 (M+H)$^+$; microanalysis, found: C,60.0; H,4.9; N,14.5%; C$_{24}$H$_{23}$N$_5$O$_4$.HCl requires: C,59.8; H,4.8; N,14.5%;

(Example 17): methyl 2-(2-methoxyethyl)-6-methyl-4-[(2'-(1H-tetrazol-5-yl)biphenyl-4-yl)methoxy]pyridine-3-carboxylate hydrochloride, m.p. 134°–135° C.; NMR (d$_6$-DMSO): 2.7(s,3H), 3.1–3.25(m,5H), 3.65(t,2H), 3.9(s,3H), 5.45(s,2H), 7.15(d,2H), 7.35(d,2H), 7.5–7.7(m,5H); mass spectrum (+ve FAB, DMSO/m-nitrobenzyl alcohol): 460 (M+H)$^+$; microanalysis, found: C,60.8; H,5.5; N,14.1%; C$_{25}$H$_{25}$N$_5$O$_4$.HCl requires: C,60.5; H,5.2; N,14.1%;

(Example 18): ethyl 6-methyl-2-phenyl-4-[(2'-(1H-tetrazol-5-yl)biphenyl-4-yl)methoxy]pyridine-3-carboxylate hydrochloride, m.p. 149°–151° C.; NMR (d$_6$-DMSO): 1.0(t,3H), 2.7(s,3H), 4.1(q,2H), 5.5(s,2H), 7.2(d,2H), 7.4(d,2H), 7.5–7.8 (complex m,10H); mass spectrum (+ve FAB, DMSO/GLY): 492 (M+H)$^+$; microanalysis, found: C,63.5; H,5.0; N,12.4%; H$_2$O, 3.9%; C$_{29}$H$_{25}$N$_5$O$_3$.HCl.H$_2$O requires: C,63.7; H,5.1; N,12.8; H$_2$O, 3.3%;

(Example 19): ethyl 2-isopropyl-6-methyl-4-[(2'-(1H-tetrazol-5-yl)biphenyl-4-yl)methoxy]pyridine-3-carboxylate hydrochloride, m.p. 158°–160° C.; NMR (d$_6$-DMSO): 1.2(t,3H), 1.4(d,6H), 2.8(s,3H), 3.1–3.3(m,1H), 4.3(q,2H), 5.4(s,2H), 7.2(d,2H), 7.4(d,2H), 7.5–7.8 (complex m,5H); mass spectrum (+ve FAB, DMSO/m-nitrobenzyl alcohol): 458 (M+H)$^+$; microanalysis, found: C,61.1; H,6.2; N,13.3; H$_2$O, 3.7%; C$_{26}$H$_{27}$N$_5$O$_3$.HCl.H$_2$O requires: C,60.9; H,5.9; N,13.7; H$_2$O, 3.5%;

(Example 20): methyl 6-methyl-2-(2-phenylethyl)-4-[(2'-(1H-tetrazol-5-yl)biphenyl-4-yl)methoxy]pyridine-3-carboxylate hydrochloride, m.p. 180°–181° C.; NMR (d$_6$-DMSO/d$_4$-acetic acid): 2.7(s,3H), 3.0(dd,2H), 3.2(dd,2H), 3.9(s,3H), 5.5(s,2H), 6.9–7.4 (complex m,9H), 7.5–7.75 (complex m,5H); mass spectrum (+ve FAB, DMSO/m-nitrobenzyl alcohol): 506 (M+H)$^+$; microanalysis, found: C,66.5; H,5.3; N,12.9%; C$_{30}$H$_{27}$N$_5$O$_3$.HCl requires: C,66.5; H,5.0; N,12.9%;

(Example 21): ethyl 6-methyl-2-propyl-4-[(2'-(1H-tetrazol-5-yl)biphenyl-4-yl)methoxy]pyridine-3-carboxylate hydrochloride, m.p. 137°–139° C.; NMR (d$_6$-DMSO): 0.9(t,3H), 1.2(t,3H), 1.6–1.8(m,2H), 2.7(s,3H), 2.8–2.95(m,2H), 4.3(q,2H), 5.4(s,2H), 7.15(d,2H), 7.4(d,2H), 7.5–7.8 (complex m,5H); mass spectrum (+ve FAB, DMSO/m-nitrobenzyl alcohol): 458(M+H)$^+$; microanalysis, found: C,62.2; H,6.0; N,13.8; H$_2$O 1.2%; C$_{26}$H$_{27}$N$_5$O.HCl.0.33H$_2$O requires: C,62.5; H,5.7; N,14.0; H$_2$O 1.2%;

(Example 22): methyl 6-methyl-2-propyl-4-[(2'-(1H-tetrazol-5-yl)biphenyl-4-yl)methoxy]pyridine-3-carboxylate hydrochloride, m.p. 162°–163° C.; NMR (d$_6$-DMSO, d$_4$-acetic acid): 0.95(t,3H), 1.6–1.8(m,2H), 2.7(s,3H), 2.85(t,2H), 3.7(s,3H), 5.5(s,2H), 7.2(d,2H), 7.4(d,2H), 7.5–7.8(m,5H); mass spectrum (+ve FAB, DMSO/m-nitrobenzyl alcohol): 444(M+H)$^+$; microanalysis, found: C,62.5; H,5.6; N,14.2%; C$_{25}$H$_{26}$N$_5$O$_3$.HCl requires: C,62.5; H,5.4; N,14.6.

The necessary starting materials of formula III used in Examples 16–22, corresponding to starting material A in Example 1, were obtained in yields of 57–87% using an analogous procedure to that described in Example 1 as follows:

(Example 16A): methyl 2-methoxymethyl-6-methyl-4-[(2'-(2-triphenylmethyl-2H-tetrazol-5-yl)biphenyl-4-yl)methoxy]pyridine-3-carboxylate, m.p. 69°–70° C.; NMR (CDCl$_3$): 2.5(s,3H), 3.4(s,3H), 3.85(s,3H), 4.6(s,2H), 5.05(s,2H), 6.65(s,1H), 6.85–7.0(m,6H), 7.15(s,4H), 7.2–7.5 (complex m,12H), 7.9–8.0(m,1H); starting from methyl 1,4-dihydro-2-methoxymethyl-6-methyl-4-oxopyridine-3-carboxylate, itself obtained in 25% yield as a gum; NMR (CDCl$_3$): 2.4(s,3H), 3.9(s,3H), 4.6(s,2H), 6.4(s,1H), from methyl 3-amino-4-methoxy-2-butenoate (obtained as described in European Patent Application 177965) and diketene using an analogous procedure to that described in Example 2A.

(Example 17A): methyl 2-(2-methoxyethyl)-6-methyl-4-[(2'-triphenylmethyl-2H-tetrazol-5-yl)biphenyl-4-yl)methoxy]pyridine-3-carboxylate, m.p. 65°–67° C; NMR (CDCl$_3$): 2.5(s,3H), 3.1(t,2H), 3.5(s,3H), 3.75(t,2H), 3.85(s,3H), 5.0(s,2H), 6.6(s,1H), 6.85–7.0(m,6H), 7.1–7.5 (complex m,16H), 7.9–8.0(m,1H); starting from methyl 1,4-dihydro-2-(2-methoxyethyl)-6-methyl-4-oxopyridine-3-carboxylate, itself obtained in 17% yield as a solid, m.p. 158°–161° C.; NMR (CDCl$_3$): 2.3(s,3H), 3.1(t,2H), 3.4(s,3H), 3.7(t,2H), 3.9(s,3H), 6.4(s,1H), from methyl 3-amino-4-(2-methoxyethyl)-2-butenoate and diketene using an analogous procedure to that described in Example 2A.

(Example 18A): ethyl 6-methyl-2-phenyl-4-(2'-triphenylmethyl-2H-tetrazol-5-yl)biphenyl-4-yl)methoxy]pyridine-3-carboxylate, m.p. 106° C.; NMR (CDCl$_3$): 1.0(t,3H), 2.55(s,3H), 4.1(q,2H), 5.1(s,2H), 6.7(s,1H), 6.9–7.0(m,6H), 7.15–7.5 (complex m,20H), 7.6–7.7(m,1H), 7.9–8.0(m,1H), starting from ethyl 1,4-dihydro-6-methyl-4-oxo-2-phenylpyridine-3-carboxylate, itself obtained in 52% yield as a solid, m.p. 192°–195° C.; NMR (CDCl$_3$/d$_4$-acetic acid): 0.9(t,3H), 2.4(s,3H), 4.0(q,2H), 6.45(s,1H), 7.4(s,5H), from ethyl 3-amino-3-phenylpropenoate and diketene using an analogous procedure to that described in Example 2A.

(Example 19A): ethyl 2-isopropyl-6-methyl-4-[(2'-(2-(2-triphenylmethyl-2H-tetrazol-5-yl)biphenyl-4-yl)methoxy]pyridine-3-carboxylate, m.p. 71°–72° C.; NMR (CDCl$_3$): 1.2–1.35(m,9H), 2.5(s,3H), 2.9–3.1(m,1H), 4.35(q,2H), 5.0(s,2H), 6.5(s,1H), 6.85–7.0(m,6H), 7.1–7.5 (complex m,16H), 7.9–8.0(m,1H); starting from ethyl 1,4-dihydro-2-isopropyl-6-methyl-4-oxopyridine-3-carboxylate, itself obtained in 40% yield as a solid, m.p. 163°–165° C.; NMR (CDCl$_3$): 1.2–1.4(m,9H), 2.3(s,3H), 2.9–3.1(m,1H), 4.3(q,2H), 6.2(br s, 1H), 11.8(s,1H), from ethyl 3-amino-4-methyl-2-pentenoate and diketene using an analogous procedure to that described in Example 2A.

(Example 20A): methyl 6-methyl-2-(2-phenylethyl)-4-[(2'-(2-triphenylmethyl-2H-tetrazol-5-yl)biphenyl-4-yl)methoxy]pyridine-3-carboxylate, m.p. 69°–72° C.; NMR (CDCl₃): 2.5(s,3H), 3.0(s,4H), 3.8(s,3H), 5.1(s,2H), 6.6(s,1H), 6.9–7.0(m,6H), 7.1–7.6 (complex m,21H), 7.9–8.0(m,1H); starting from methyl 1,4-dihydro-6-methyl-4-oxo-2-(2-phenylethyl)pyridine-3-carboxylate, itself obtained in 8% yield as a solid, m.p. 201°–210° C.; NMR (d₆-DMSO): 2.35(s,3H), 3.0(s,4H), 3.9(s,3H), 6.5(s,1H), 7.15–7.4(m,5H), 7.5(s,1H), from methyl 3-amino-5-phenyl-2-pentenoate and diketene using an analogous procedure to that described in Example 2A.

(Example 21A): ethyl 6-methyl-2-propyl-4-[(2'-(2-triphenylmethyl-2H-tetrazol-5-yl)biphenyl-4-yl)methoxy]pyridine-3-carboxylate, m.p. 135°–136° C.; NMR (CDCl₃): 1.0(t,3H), 1.3(t,3H), 1.6–1.8(m,2H), 2.5(s,3H), 2.7–2.8(m,2H), 4.3(q,2H), 5.0(s,2H), 6.55(s,1H), 6.9–7.0(m,6H), 7.1–7.5 (complex m,16H), 7.9–8.0(m,1H); starting from ethyl 1,4-dihydro-6-methyl-4-oxo-2-propylpyridine-3-carboxylate, itself obtained in 28% yield as a solid, m.p. 108°–112° C.; NMR (CDCl₃): 0.9(t,3H), 1.3(t,3H), 1.6–1.8(m,2H), 2.5(s,3H), 2.6–2.7(m,2H), 4.3(q,2H), 6.2(s,1H), from ethyl 3-amino-2-hexenoate and diketene using an analogous procedure to that described in Example 2A.

(Example 22A): methyl 6-methyl-2-propyl-4-[(2'-(2-triphenylmethyl-2H-tetrazol-5-yl)biphenyl-4yl)methoxy]pyridine-3-carboxylate, m.p. 66°–71° C.; NMR (CDCl₃): 1.0(t,3H), 1.7–1.9(m,2H), 2.5(s,3H), 2,65–2.8(m,2H), 3.9(s,3H), 5.2(s,2H), 6.6(s,1H), 6.8–6.95(m,6H), 7.1–7.6 (complex m,16H), 7.9–8.0(m,1H); starting from methyl 1,4-dihydro-6-methyl-4-oxo-2-propylpyridine-3-carboxylate, itself obtained in 46% yield as a solid, m.p. 142°–144° C.; NMR (CDCl₃): 0.9(t,3H), 1.6–1.8(m,2H), 2.3(s,3H), 2.65(t,2H), 3.8(s,3H), 6.2(s,1H), 12.0(br, 1H), from methyl 3-amino-2-hexenoate and diketene using an analogous procedure to that described in Example 2A.

EXAMPLE 23

Using an analogous procedure to that described in Example 1, but starting from 2,6-dimethyl-3-methoxymethyl-4-[(2'-2-triphenylmethyl-2H-tetrazol-5-yl)biphenyl-4-yl)methoxy]pyridine (A), there was obtained in 81% yield 2,6-dimethyl-3-methoxymethyl-4-[(2'-(1H-tetrazol-5-yl)biphenyl-4-yl)methoxy]pyridine hydrochloride, as a white powder, m.p. 193° C.; NMR (d₆-DMSO/d₄-acetic acid): 2.7(s,6H), 3.3(s,3H), 4.5(s,2H), 5.45(s,2H), 7.2–7.8 (complex m,9H); mass spectrum (+ve FAB, DMSO/m-nitrobenzyl alcohol): 402 (M+H)⁺.

The starting material (A) was obtained as follows:

Sodium hydride (115 mg) was added to a solution of 2,6-dimethyl-3-hydroxymethyl-4-[(2'-(2-triphenylmethyl-2H-tetrazol-5-yl)biphenyl-4-yl)methoxy]pyridine (1.0 g) in DMF (30 ml) and the mixture was stirred for 10 minutes. Iodomethane (0.3 ml) was added and the mixture was stirred for 18 hours. Water (100 ml) was added and the mixture was extracted with ethyl acetate (2×50 ml). The combined extracts were washed with saturated sodium chloride solution (50 ml) and then dried (MgSO₄). The solvent was removed by evaporation and the residue was purified by flash chromatography, eluting with a mixture of methanol and dichloromethane on a gradient from 1:50 v/v to 1:20 v/v, to give 2,6-dimethyl-3-methoxymethyl-4-[(2'-(2-triphenylmethyl-2H-tetrazol-5-yl)biphenyl-4-yl)methoxy]pyridine (A) (0.74 g), m.p. 132°–135° C.; NMR (d₆-DMSO/d₄-acetic acid): 2.55(s,6H), 3.2(s,3H), 4.45(s,2H), 5.25(s,2H), 6.8–7.9 (complex m,24H).

EXAMPLE 24

Using an analogous procedure to that described in Example 1, but starting from 2,3,6-trimethyl-4-[(2'-(2-triphenylmethyl-2H-tetrazol-5-yl)biphenyl-4-yl)methoxy]pyridine (A) there was obtained in 50% yield 2,3,6-trimethyl-4-[(2'-(1H-tetrazol-5-yl)biphenyl-4-yl)methoxy]pyridine hydrochloride, as a white powder, m.p. 212° C.; NMR (d₆-DMSO/d₄-acetic acid): 2.2(s,3H), 2.6(s,3H), 2.7(s,3H), 5.45(s,2H), 7.2–7.8 (complex m,9H); mass spectrum (+ve FAB, DMSO/m-nitrobenzyl alcohol): 372 (M+H)⁺; microanalysis, found: C,64.2; H,6.1; N,17.0; Cl,8.4%; C₂₂H₂₁N₅O.HCl requires: C,64.8; H,5.4; N,17.2; Cl,8.7%.

The starting material (A) was obtained as follows:

(i) Triethylamine (2.2 ml) and methanesulphonyl chloride (1.24 ml) were added to a solution of 2,6-dimethyl-3-hydroxymethyl-4-[(2'-(2-triphenylmethyl-2H-tetrazol-5-yl)biphenyl-4-yl)methoxy]pyridine (10.0 g) in dichloromethane (150 ml). The solution was left to stand for 20 hours and then diluted with water (150 ml). The organic phase was separated, washed with saturated sodium chloride solution (150 ml), and dried (MgSO₄). Volatile material was removed by evaporation and the residue was purified by flash chromatography, eluting with methanol/dichloromethane (1:19 v/v) to give 3-chloromethyl-2,6-dimethyl-4-[(2'-(2-triphenylmethyl-2H-tetrazol-5-yl)biphenyl-4-yl-methoxy]pyridine (B) (8.5 g), as a white solid, m.p. 110°–112° C.; NMR (d₆-DMSO/d₄-acetic acid): 2.5(s,3H), 2.65(s,3H), 4.75(s,2H), 5.45(s,2H), 6.9–7.9 (complex m,24H).

(ii) A solution of compound B (1.0 g) and sodium iodide (232 mg) in acetone (20 ml) was heated under reflux for 6 hours. Volatile material was removed by evaporation and the residue was partitioned between dichloromethane (20 ml) and water (20 ml). The organic phase was separated, washed with saturated sodium chloride solution (20 ml) and dried (MgSO₄). The solvent was removed by evaporation and the residue was dissolved in DMF (25 ml). Sodium cyanoborohydride (221 mg) was added and the mixture was stirred for 3 hours. Volatile material was removed by evaporation and the residue was partitioned between dichloromethane (20 ml) and water (20 ml). The organic phase was separated, washed with saturated sodium chloride solution (20 ml) and dried (MgSO₄). The solvent was removed by evaporation and the residue was purified by flash chromatography, eluting with methanol/dichloromethane (1:19 v/v), to give 2,3,6-trimethyl-4-[(2'-(2-triphenylmethyl-2H-tetrazol-5-yl)biphenyl-4-yl)methoxy]pyridine (A) (0.65 g), m.p. 136°–138° C.; NMR (d₆-DMSO/d₄-acetic acid): 2.1(s,3H), 2.5(s,3H), 2.6(s,3H), 5.3(s,2H), 6.8–7.0(m,6H), 7.2–7.85 (complex m,18H).

EXAMPLE 25

Using an analogous procedure to that described in Example 1, but starting from 3-aminomethyl-2,6-dimethyl-4-[(2'-(2-triphenylmethyl-2H-tetrazol-5-yl)biphenyl-4-yl)methoxy] pyridine (A), there was obtained in 60% yield 3-aminomethyl-2,6-dimethyl-4-[(2'-(1H-tetrazol-5-yl)biphenyl-4-yl)methoxy]pyridine dihydrochloride, m.p. 147°–150° C.; NMR (d₆-DMSO/d₄-acetic acid): 2.7(s,3H), 2.85(s,3H), 4.15(s,2H), 5.5(s,2H), 7.2-7.8 (complex m,9H); mass spectrum (+ve FAB, DMSO/m-nitrobenzyl alcohol): 387 (M+H)+.

The starting material (A) was obtained as follows:

A solution of 3-chloromethyl-2,6-dimethyl-4-[(2'-(2-triphenylmethyl-2H-tetrazol-5-yl)biphenyl-4-ylmethoxy]pyridine (1.0 g) in dioxan (10 ml) was saturated with ammonia gas and then heated at 85° C. in an autoclave for 3 hours. Volatile material was removed by evaporation and the residue was purified by flash chromatography, eluting with methanol/dichloromethane (1:9 v/v), to give 3-aminomethyl-2,6-dimethyl-4-[(2'(2-triphenylmethyl-2H-tetrazol-5-yl)biphenyl-4-yl)methoxy]pyridine (320 mg), as a foam; NMR (d6-DMSO/d4-acetic acid): 2.4(s,6H), 4.05(s,2H), 5.2(s,2H), 6.9-7.8 (complex m,24H).

EXAMPLE 26

Using an analogous procedure to that described in Example 1, but starting from 2,6-dimethyl-3-formyl-4-[(2'-(2-triphenylmethyl-2H-tetrazol-5-yl)biphenyl-4-yl)methoxy]pyridine (A), there was obtained in 95% yield 2,6-dimethyl-3-formyl-4-[(2'-(1H-tetrazol-5-yl)biphenyl-4-yl)methoxy]pyridine hydrochloride, m.p. 124°-130° C.; NMR (d6-DMSO): 2.7(s,3H), 2.9(s,3H), 5.5(s,2H), 7.2(d,2H), 7.5-7.8 (complex m,7H), 10.4(s,1H); mass spectrum (−ve FAB, DMSO/GLY): 384 (M−H)−; microanalysis, found: C,60.8; H,5.1; N,15.9; $C_{22}H_{19}N_5O_2 \cdot HCl \cdot 0.75H_2O$ requires: C,60.7; H,4.9; N,16.0;

The starting material (A) was obtained as follows:

(i) Chloroform (12 ml) was added in 1 ml portions over a period of 2 hours to a refluxing solution of 2,6-dimethyl-4-(1H)-pyridone (6.2 g) in 4M aqueous sodium hydroxide (112 ml). The solution was heated under reflux for 6 hours, cooled and acidified to pH 6 with acetic acid. Volatile material was removed by evaporation and the residue was extracted with methanol (3×100 ml). The extracts were concentrated and the residue was purified by flash chromatography, eluting with methanol/dichloromethane (1:9 v/v), to give 2,6-dimethyl-3-formyl-4(1H)-pyridone (B) (2.1 g) as a solid, m.p. >100° C. (decomposition); NMR (d6-DMSO): 2.2(s,3H), 2.5(s,3H), 6.1(s,1H), 10.25(s,1H).

(ii) Using an analogous procedure to that described in Example 1, but starting from compound (B) there was obtained in 67% yield 2,6-dimethyl-3-formyl-4-[(2'-(2-triphenylmethyl-2H-tetrazol-5-yl)-biphenyl-4-yl)methoxy]pyridine (A), m.p. 160°-162° C.; NMR (CDCl3): 2.5(s,3H), 2.8(s,3H), 5.1(s,2H), 6.7(s,1H), 6.85-6.95(m,6H), 7.1-7.5 (complex m,16H), 7.95-8.0(m,1H), 10.6(s,1H).

EXAMPLES 27-28

Using an analogous procedure to that described in Example 1, but starting from the appropriate compound of formula III wherein L is triphenylmethyl, the following compounds of formula I were obtained in yields of 53-98%:

(Example 27): 3-acetyl-2,6-dimethyl-4-[(2'-(1H-tetrazol-5-yl)-biphenyl-4-yl)methoxy]pyridine hydrochloride, m.p. 138°-141° C.; NMR (d6-DMSO): 2.4-2.6(m,6H), 2.7(s,3H), 5.4(s,2H), 7.2(d,2H), 7.4(d,2H), 7.5-7.8(m,5H); mass spectrum (−ve FAB, DMSO/GLY): 398 (M−H)−; microanalysis, found: C,62.5; H,5.0; N,15.6; H2O 0.7%; $C_{23}H_{21}N_5O_2 \cdot HCl \cdot 0.17H_2O$ requires: C,62.9; H,5.1; N,15.9%; H2O,0.7%.

(Example 28): 6-ethyl-2-methyl-3-propanoyl-4-[(2'-(1H-tetrazol-5-yl)biphenyl-4-yl)methoxy]pyridine hydrochloride, m.p. 160°-162° C.; NMR (d6-DMSO/d4-acetic acid): 1.0(t,3H), 1.25(t,3H), 2.7(m,4H), 5.4(s,2H), 7.2(d,2H), 7.4(d,2H), 7.5-7.8 (complex m,5H); mass spectrum (−ve FAB, DMSO/m-nitrobenzyl alcohol): 428 (M+H)+; microanalysis, found: C,64.4; H,5.7; N,15.0% $C_{25}H_{25}N_5O_2 \cdot HCl$ requires: C,64.7; H,5.6; N,15.1%.

The necessary starting materials of formula III used in Examples 27-28, corresponding to starting material A in Example 1, were obtained in yields of 33-77% using an analogous procedure to that described in Example 1 as follows:

(Example 27A): 3-acetyl-2,6-dimethyl-4-[(2'-(2-triphenylmethyl-2H-tetrazol-5-yl)biphenyl-4-yl)methoxy]pyridine m.p. 79°-82° C.; NMR (CDCl3): 2.4-2.5(m,9H), 5.0(s,2H), 6.6(s,1H), 6.9-7.0(m,6H), 7.1-7.55 (complex m,16H), 7.9-8.0 (M,1H); starting from 3-acetyl-2,6-dimethyl-4-(1H)-pyridone, itself obtained as described in *Liebigs Ann. Chem.*, 1979, 371.

(Example 28A): 6-ethyl-2-methyl-3-propanoyl-4-[2'-(2-triphenylmethyl-2H-tetrazol-5-yl)biphenyl)methoxy]pyridine, m.p. 123°-124° C.; NMR (CDCl3): 1.1(t,3H), 1.3(t,3H), 2.5(s,3H), 2.65(q,2H), 2.8(q,2H) 5.0(s,2H), 6.6(s,1H), 6.9-7.0(m,6H), 7.05-7.5 (complex m,16H), 7.9-8.0(m,1H); starting from 6-ethyl-2-methyl-3-propanoyl-4-(1H)-pyridone, itself obtained as described in *Liebigs Ann. Chem.*, 1979, 371.

EXAMPLE 29

Using an analogous procedure to that described in Example 1, but starting from 3-cyano-2,6-dimethyl-4-[(2'-(2-triphenymethyl-2H-tetrazol-5-yl)biphenyl-4-yl)methoxy]pyridine (A), there was obtained in 41% yield 3-cyano-2,6-dimethyl-4-[2'-(1H-tetrazol-5-yl)biphenyl-4-yl)methoxy]pyridine hydrochloride, as a white solid, m.p. 147°-149° C.; NMR (d6-DMSO/d4-acetic acid): 2.7(s,3H), 2.8(s,3H), 5.5(s,2H), 7.2-7.7 (complex m,9H); mass spectrum (+ve FAB, DMSO/m-nitrobenzyl alcohol): 383 (M+H)+; microanalysis, found: C,61.7; H,4.6; N,18.9%; $C_{22}H_{19}N_6O \cdot HCL \cdot 0.5H_2O$ requires: C,61.8; H,4.7; N,19.6%.

The starting material (A) was obtained as follows:

Using an analogous procedure to that described in Example 15, part (iii), but starting from 4-chloro-3-cyano-2,6-dimethylpyridine (obtained as described in European Patent Application, Publication No. 104876) there was obtained in 25% yield 3-cyano-2,6-dimethyl-4-[(2'-(2-triphenylmethyl-2H-tetrazol-5-yl)biphenyl-4-yl)methoxy]pyridine (A), as a foam; NMR (CDCl3): 2.5(s,3H), 2.7(s,3H), 5.1(s,2H), 6.6-8.0 (complex m,24H).

EXAMPLES 30-31

Using an analogous procedure to that described in Example 1, but starting from the appropriate compound of formula III wherein L is triphenylmethyl, the following compounds of formula I were obtained in yields of 40-46%:

(Example 30): 2,6-diethyl-4-[(2'-1H-tetrazol-5-yl)biphenyl-4-yl)methoxy]pyridine-3-carboxamide, m.p. 235°-255° C. (decomposition); NMR (d6-DMSO): 1.3-1.4(m,6H), 2.95-3.05(m,4H), 5.5(s,2H), 7.2(d,2H), 7.4(d,2H), 7.5-7.8(m,5H), 7.9(s,1,H), 8.1(s,1H); mass spectrum (+ve FAB, DMSO/m-nitrobenzyl alcohol): 429 (M+H)+; microanalysis, found: C,61.9; H,5.1;

N,17.7%; $C_{29}H_{24}N_6O_2 \cdot HCl$ requires: C,62.0; H,5.4; N,18.1%.

(Example 31): 2,6-dimethyl-4-[(2'-1H-tetrazol-5-yl)biphenyl-4-yl)methoxy]pyridine-3-carboxamide, m.p. 179°-183° C.; NMR ($d_6$-DMSO/$d_4$-acetic acid): 2.65(s,3H), 2.7(s,3H), 5.45(s,2H), 7.15-7.75 (complex m,9H); mass spectrum (−ve FAB, DMSO/m-nitrobenzyl alcohol): 401 $(M+H)^+$.

The necessary starting materials of formula III used in Examples 30-31, corresponding to starting material A in Example 1, were obtained in yields of 35-41% using an analogous procedure to that described in Example 1 as follows:

(Example 30A): 2,6-diethyl-4-[(2'-(2-triphenylmethyl-2H-tetrazol-5-yl)biphenyl-4-yl)methoxy]pyridine-3-carboxamide as a foam; NMR ($d_6$-DMSO): 1.2-1.3(m,6H), 2.6-2.7(m,4H), 5.1(s,2H), 6.8-7.0(m,6H), 7.1(d,2H), 7.3-7.9 (complex m,16H) starting from 2,6-diethyl-1,4-dihydro-4-oxopyridine-3-carboxamide, itself obtained as follows:

A 1.3M solution of aminodimethyl aluminium in dichloromethane (obtained as described in *Tetrahedron Letters*, 1979, 4907) (7.8 ml) was added to a solution of methyl 2,6-diethyl-1,4-dihydro-4-oxopyridine-3-carboxylate (1.05 g in dichloromethane (50 ml) and the solution was left to stand for 20 hours. Methanol (5 ml) was added and the mixture was stirred for 1 hour. The precipitated solid was removed by filtration through a bed of diatomaceous earth. The filtrate was concentrated and the residue purified by flash chromatography, eluting with methanol/dichloromethane (1:9 v/v), to give 2,6-diethyl-1,4-dihydro-4-oxopyridine-3-carboxamide (0.5 g), m.p. 254° C.; NMR ($d_6$-DMSO): 1.15-1.25(m,6H), 2.5(q,2H), 3.0(q,2H), 6.1(s,1H), 7.0(br s, 1H), 9.6(br s, 1H), 11.3(br s, 1H).

(Example 31A): 2,6-dimethyl-4-[(2'-(2-triphenylmethyl-2H-tetrazol-5-yl)biphenyl-4-yl)methoxy]pyridine-3-carboxamide as a foam; NMR ($d_6$-DMSO/$d_4$-acetic acid): 2.4(s,6H), 5.15(s,2H), 6.8-7.85 (complex m,24H); starting from 1,4-dihydro-2,6-dimethyl-4-oxopyridine-3-carboxamide, itself obtained as a foam; NMR ($d_6$-DMSO/$d_4$-acetic acid): 2.3(s,3H), 2.6(s,3H), 6.2(s,1H), from methyl 1,4-dihydro-2,6-dimethyl-4-oxopyridine-3-carboxylate using an analogous procedure to that described in Example 30A.

EXAMPLE 32

Using an analogous procedure to that described in Example 1, but starting from 2,6-dimethyl-3-(4-fluorophenyl)-4-[(2'-(2-triphenylmethyl-2H-tetrazol-5-yl)biphenyl-4-yl)methoxy]pyridine (A), there was obtained in 88% yield 2,6-dimethyl-3-(4-fluorophenyl)-4-[(2'-(1H-tetrazol-5-yl)biphenyl-4-yl)methoxy]pyridine hydrochloride; NMR ($d_6$-DMSO/$d_4$-acetic acid): 2.4(s,3H), 2.75(s,3H), 5.4(s,2H), 7.1(d,2H), 7.2-7.5(m,7H), 7.5-7.8(m,4H); mass spectrum (+ve FAB, DMSO/GLY): 452 $(M+H)^+$; microanalysis, found: C,65.8; H,5.4; N,12.8%; $C_{27}H_{22}FN_5O \cdot HCl \cdot 0.25 H_2O \cdot 0.5(C_2H_5)_2O$ requires: C,65.7; H,5.4; N,13.2%.

The starting material (A) was obtained as follows:

(i) A mixture of (4-fluorophenyl)propanone (4 g), acetic acid (20 ml) and polyphosphoric acid (30 g) was heated at 160° C. for 2.5 hours. The mixture was cooled to 80° C., poured onto crushed ice (300 g) and neutralised by the addition of solid sodium carbonate. The mixture was then extracted with ethyl acetate (2×150 ml) and the combined extracts were washed with saturated sodium chloride solution (100 ml) and dried ($MgSO_4$). The solvent was removed by evaporation and the residue was purified by flash chromatography, eluting with ethyl acetate/hexane (1:1 v/v) to give 2,6-dimethyl-3-(4-fluorophenyl)-4H-pyran-4-one (B) (2.85 g), m.p. 114°-115° C.; NMR ($d_6$-DMSO): 2.15(s,3H), 2.3(s,3H). 6.2(s,1H), 7.15-7.3(m,4H).

(ii) Using an analogous procedure to that described in Example 13A, but starting from compound B, there was obtained in 74% yield 2,6-dimethyl-3-(4-fluorophenyl)-4-(1H)-pyridone (C), m.p.>250° C.; NMR ($d_6$-DMSO): 2.1(s,3H). 2.2(s,3H), 5.9(s,1H), 7.1-7.3(m,4H).

(iii) Using an analogous procedure to that described in Example 1, but starting from compound C, there was obtained in 94% yield 2,6-dimethyl-3-(4-(fluorophenyl)-4-[(2'-(2-triphenylmethyl-2H-tetrazol-5-yl)biphenyl-4-yl)methoxy]pyridine as a foam; NMR ($CDCl_3$): 2.3(s,3H), 2.7(s,3H), 5.0(s,2H), 6.6(s,1H), 6.85-7.0(m,10H), 7.05-7.6 (complex m,16H), 7.9-8.0(m,1H).

EXAMPLE 33

Using an analogous procedure to that described in Example 1, but starting from methyl 2-methyl-6-propyl-4-[(2'-(2-triphenylmethyl-2H-tetrazol-5-yl)biphenyl-4-yl)methoxy]pyridine-3-carboxylate (A), there was obtained in 95% yield methyl 2-methyl-6-propyl-4-[(2'-1H-tetrazol-5-yl)biphenyl-4-yl)methoxy]pyridine-3-carboxylate hydrochloride, m.p. 105°-110°C.; NMR ($d_6$-DMSO/$d_4$-acetic acid): 0.95(t,3H), 1.7-1.9(m,2H), 2.95(t,2H), 3.9(s,3H), 5.5(s,2H), 7.2(d,2H), 7.4(d,2H), 7.55-7.8(m,5H); mass spectrum (+ve FAB, DMSO/m-nitrobenzyl alcohol): 444 $(M+H)^+$; microanalysis, found: C,61.0, H,5.6; N,13.6; $H_2O$, 2.1%; $C_{25}H_{25}N_5O_3 \cdot HCl \cdot 0.6H_2O$ requires C,61.3; H,5.6; N,13.9; $H_2O$, 2.1%.

The starting material (A) was obtained as follows:

(i) Using an analogous procedure to that described in Example 10A, but starting from 5-(1-hydroxybutylidene)-2,2-dimethyl-1,3-dioxane-4,6-dione (obtained as described in *J. Org. Chem.*, 1978, 43, 2087), there was obtained in 42% yield methyl 1,4-dihydro-2-methyl-6-propyl-4-oxopyridine-3-carboxylate (B), m.p. 132°-136° C.; NMR ($d_6$-DMSO): 0.9(t,3H), 1.5-1.7(m,2H), 2.2(s,3H), 2.4(t,2H), 3.7(s,3H), 5.9(s,1H), 11.2(br s, 1H).

(ii) Using an analogous procedure to that described in Example 1, but starting from compound A, there was obtained in 90% yield methyl 2-methyl-6-propyl-4-[(2'-(2-triphenylmethyl-2H-tetrazol-5-yl)biphenyl-4-yl)methoxy]pyridine-3-carboxylate (A), m.p. 61°-64° C.; NMR ($CDCl_3$): 0.95(t,3H), 1.6-1.8(m,2H), 2.5(s,3H), 2.7(t,2H), 3.9(s,3H), 5.05(s,2H), 6.6(s,1H), 6.9-7.0(m,6H), 7.1-7.5 (complex m,16H), 7.9-8.0(m,1H).

EXAMPLE 34

Using an analogous procedure to that described in Example 1, but starting from 5,6,7,8-tetrahydro-2-trifluoromethyl-4-[(2'-(2-triphenylmethyl-2H-tetrazol-5-yl)biphenyl-4-yl)methoxy]quinoline (A), there was obtained in 45% yield 5,6,7,8-tetrahydro-4-[(2'-(1H-tetrazol-5-yl)biphenyl-4-yl)methoxy]-2-trifluoromethylquinoline, m.p. 218°-219° C.; NMR ($d_6$DMSO): 1.7-1.9(m,4H), 2.6-2.7(m,2H), 2.8-2.9(m,2H), 5.3(s,2H), 7.15(d,2H), 7.3-7.5(m,3H), 7.55-7.75(m,4H); mass spectrum (+ve FAB, DMSO/m-nitrobenzyl alcohol): 452 $(M+H)^+$; microanalysis, found: C,61.3; H,4.9; N,14.5;

$C_{24}H_{20}F_3N_5O \cdot CH_3OH \cdot 0.5H_2O$ requires: C,61.5; H,5.0; N,14.5%.

The starting material (A) was obtained as follows:

(i) A solution of 2-trifluoromethyl-4(1H)-quinolone (obtained as described in *J. Het. Chem.*, 1965, 2, 113) (440 mg) in acetic acid (5 ml) was catalytically hydrogenated over platinum oxide (50 mg) at 1 atmosphere pressure. When uptake of hydrogen ceased, the catalyst was removed by filtration through diatomaceous earth. The filtrate was concentrated, toluene (10 ml) was added to the residue and the solution was evaporated. The residue was triturated with ether/hexane (1:5 v/v, 10 ml) to give 5,6,7,8-tetrahydro-2-trifluoromethyl-4(1H)-quinolone (B) (312 mg), m.p. 171°–172° C.; NMR ($d_6$-DMSO): 1.7–1.95(m,4H), 2.7(m,2H), 2.9(m,2H), 7.0(s,1H).

(ii) Using an analogous procedure to that described in Example 1, but starting from compound B, there was obtained in 53% yield 5,6,7,8-tetrahydro-2-trifluoromethyl-4-[(2′-(2-triphenylmethyl-2H-tetrazol-5-yl)biphenyl-4-yl)methoxy]quinoline (A), m.p. 141°–143° C.; NMR (CDCl$_3$): 1.7–1.95(m,4H), 2.65–2.75(m,2H), 2.9–3.0(m,2H), 5.0(s,2H), 6.85–6.95(m,6H), 7.0(s,1H), 7.15–7.55 (complex m,16H), 8.0(dd,1H).

EXAMPLE 35

Sodium hydroxide (0.5 g) was added to a solution of methyl 4′-[(2-ethyl-5,6,7,8-tetrahydroquinolin-4-yloxy)methyl]biphenyl-2-carboxylate (A) (0.5 g) in methanol (20 ml) and water (2 ml). The solution was heated under reflux for 6 hours and then volatile material was removed by evaporation. The residue was dissolved in water and the solution was acidified with acetic acid to precipitate 4′-[(2-ethyl-5,6,7,8-tetrahydroquinolin-4-yloxy)methyl]biphenyl-2-carboxylic acid (200 mg), m.p. 222° C. (from a mixture of DMSO and water); NMR ($d_6$-DMSO): 1.2(t,3H), 1.65–1.85(m,4H), 2.55–2.8(m,6H), 5.7(s,2H), 6.8(s,1H), 7.3–7.6 (complex m,7H), 7.7(dd,1H); mass spectrum (+ve FAB, DMSO/m-nitrobenzyl alcohol): 388 (M+H)$^+$; microanalysis, found: C,76.0; H,6.4; N,3.8%; $C_{26}H_{27}NO_3 \cdot 0.5H_2O$ requires: C,75.7; H,6.6; N,3.5%.

The starting material (A) was obtained as follows: (i) A 1.6M solution of butyllithium in hexane (24.0 ml) was added dropwise to a stirred solution of 4-bromotoluene (6.0 g) in dry THF (50 ml) at −78° C. under an atmosphere of argon. The temperature was maintained at −78° C. for 20 minutes and then a 1M solution of anhydrous zinc chloride in ether (38.6 ml) was added. The solution was kept at −78° C. for 15 minutes, and then tetrakis(triphenylphosphine)palladium (60 mg) in THF (5 ml) was added, followed by methyl 2-iodobenzoate (6.1 g) in THF (10 ml). The solution was allowed to reach ambient temperature over 1 hour, then heated under reflux for 5 hours. The solvent was removed by evaporation and the residue was dissolved in chloroform (150 ml). The solution was washed with a solution of ethylenediaminetetracetic acid (10 g) in water (100 ml) and the aqueous layer was re-extracted with chloroform (100 ml). The combined organic extracts were dried (MgSO$_4$) and the solvent removed by evaporation. The residue was purified by flash chromatography, eluting with ethyl acetate/hexane (1:9 v/v), to give methyl 4′-methylbiphenyl-2-carboxylate (B) as a colourless oil (4.4 g); NMR: 2.4(s,3H), 3.65(s,3H), 7.2(s,4H), 7.35(m,3H), 7.5(m,1H), 7.8(d,1H).

(ii) N-Bromosuccinimide (8.1 g) and azo(bisisobutyronitrile) (130 mg) were added to a solution of compound B (9.3 g) in carbon tetrachloride (300 ml). The mixture was heated under reflux for 4 hours and then cooled to ambient temperature. Insoluble material was removed by filtration and the filtrate concentrated. The residue was purified by flash chromatography, eluting with ethyl acetate/hexane (1:9 v/v), to give methyl 4′-(bromomethyl)biphenyl-2-carboxylate (C) as a solid (10.9 g), m.p. 48°–50° C.; NMR (CDCl$_3$): 3.65(s,3H), 4.55(s,2H), 7.25–7.60 (complex m,7H), 7.85(d,1H).

(iii) Using an analogous procedure to that described in Example 1, but starting from compound C and 2-ethyl-5,6,7,8-tetrahydro-4(1H)-quinolone (itself obtained as a solid [m.p. 226°–227° C.; NMR ($d_6$-DMSO): 1.15(t,3H), 1.55–1.75(m,4H), 2.25(t,2H), 2.4(q,2H), 2.45–2.55(m,2H), 5.8(s,1H)] using a similar procedure to that described in Liebigs Ann. Chem. 1982, 1656–1658 for the preparation of 2-methyl-5,6,7,8-tetrahydro-4(1H)-quinolone but reducing the intermediate 2-ethyl-4(1H)-quinoline (m.p. 178°–181° C.) by catalytic hydrogenation over platinum oxide in acetic acid at one atmosphere pressure), there was obtained in 62% yield methyl 4′-[(2-ethyl-5,6,7,8-tetrahydroquinolin-4-yloxy)methyl]biphenyl-2-carboxylate (A), m.p. 86°–88° C.; NMR (CDCl$_3$): 1.3(t,3H), 1.7–1.95(m,4H), 2.65–2.9(m,6H), 3.65(s,3H), 5.15(s,2H), 6.55(s,1H), 7.2–7.6 (complex m,7H), 7.75(dd,1H).

EXAMPLE 36

Hydrogen chloride was bubbled for 30 minutes through a solution of 4-[(4′-chloro-2′-(2-tributylstannyl-2H-tetrazol-5-yl)biphenyl-4-yl)methoxy]-2-ethyl-5,6,7,8-tetrahydroquinoline in xylene [prepared by heating a mixture of 4-[(4′-chloro-2′-cyanobiphenyl-4-yl)methoxy]-2-ethyl-5,6,7,8-tetrahydroquinoline (A) (306 mg) and tributyl tin azide (800 mg) in xylene (1.5 ml) at 130° C. for 60 hours under an atmosphere of argon]. Volatile material was then removed by evaporation and the residue was purified by flash chromatography, eluting with methanol/ethyl acetate (1:9 v/v), to give 4-[(4′-chloro-2′-(1H-tetrazol-5-yl)biphenyl-4-yl)methoxy]-2-ethyl-5,6,7,8-tetrahydroquinoline hydrochloride (176 mg), m.p. 217°–218° C. (from ethanol/ethyl acetate); NMR ($d_6$-DMSO): 1.3(t,3H), 1.7–1.9(m,4H), 2.55–2.65(m,2H), 2.85–3.0(m,4H), 5.45(s,2H), 7.2(d,2H), 7.4(s,1H), 7.45(d,2H), 7.6(d,1H), 7.8(dd,1H), 7.8(d,1H); mass spectrum (+ve FAB, DMSO/m-nitrobenzyl alcohol): 446 (M+H)$^+$; microanalysis, found: C,61.0; H,5.3; N,14.0%; $C_{25}H_{24}ClN_5O \cdot HCl \cdot 0.5H_2O$ requires: C,61.2; H,5.3; N,14.3%.

The starting material (A) was obtained as follows:

(i) Sodium hydride (60% dispersion in oil; 180 mg) was added to a mixture of 2-ethyl-5,6,7,8-tetrahydro-4(1H)-quinolone (660 mg) and 4-bromomethylphenylboronic acid (800 mg) (obtained as described in *J. Amer. Chem. Soc.* 1958, 80, 835) in DMF (12 ml) under an atmosphere of argon. The mixture was stirred for 40 hours and then water (0.2 ml) was added. Volatile material was removed by evaporation and the residue was dissolved in warm 0.5M sodium hydroxide solution (10 ml). Insoluble material was removed by filtration and the filtrate was acidified to pH 4 with 20% citric acid solution. The precipitate solid was collected by filtration, washed with water (20 ml) and dried under high vacuum to give 4-[(2-ethyl-5,6,7,8-tetrahydroquinolin-4-yl)oxymethyl]phenylboronic acid (C) (1.15 g), m.p. 229°–231° C.; NMR ($d_6$-DMSO): 1.3(t,3H), 1.6–1.9(m,4H), 2.5–2.7(m,2H), 2.75–2.95(m,4H), 5.4(s,2H), 7.3(d,2H), 7.4(s,1H), 7.5(d,2H).

(ii) Methanesulphonyl chloride (0.85 ml) was added to a solution of 2-bromo-5-chlorobenzoic acid (2.55 g) and pyridine (1.3 ml) in dichloromethane (5 ml) under an atmosphere of argon. The mixture was stirred for 1.5 hours and then gaseous ammonia was bubbled through for 5 minutes. Volatile material was removed by evaporation and the residue was suspended in chloroform (5 ml). Thionyl chloride (3 ml) was added and the mixture was heated under reflux for 20 hours. Volatile material was removed by evaporation and the residue was partitioned between dichloromethane (50 ml) and water (30 ml). The organic layer was separated, washed with water (30 ml) and dried (MgSO$_4$). The solvent was removed by evaporation and the residue recrystallised from ethyl acetate/hexane (1:1 v/v) to give 2-bromo-5-chlorobenzonitrile (B) (1.64 g), m.p. 135°–137° C.; NMR (CDCl$_3$): 7.4(dd,1H), 7.6(d,1H), 7.65(d,1H).

(iii) Compound B (317 mg) and compound C (500 mg) were suspended in a mixture of toluene (5 ml), ethanol (1 ml) and 2M sodium carbonate solution (1.5 ml). Tetrakis(triphenylphosphine)palladium (85 mg) was added and the mixture was degassed by purging with argon. The mixture was heated at 120° C. for 18 hours under an atmosphere of argon. Dichloromethane (30 ml) and water (10 ml) were added and the organic layer was separated and dried (MgSO$_4$). Volatile material was removed by evaporation and the residue was purified by flash chromatography, eluting with ethyl acetate/hexane (3:1 v/v), to give 4-[(4'-chloro-2'-cyanobiphenyl-4-yl)methoxy]-2-ethyl-5,6,7,8-tetrahydroquinoline (A) (316 mg), m.p. 145°–147° C. (after trituration with a mixture of ether and hexane); NMR (CDCl$_3$): 1.3(t,3H), 1.7–1.95(m,4H), 2.65–2.75(m,2H), 2.8(q,2H), 2.9–3.0(m,2H), 5.2(s, 2H), 6.6(s,1H), 7.5(d,1H), 7.6(s,4H), 7.65(dd,1H), 7.75(d,1H).

EXAMPLE 37

Using an analogous procedure to that described in Example 36, but starting from 2-ethyl-4-[(4'-methoxy-2'-(2-tributylstannyl-2H-tetrazol-5-yl)biphenyl-4-yl)methoxy]-5,6,7,8-tetrahydroquinoline [prepared as a solution in xylene using a similar procedure to that described in Example 36 but starting from 4-[(2'-cyano-4'-methoxybiphenyl-4-yl)methoxy]-2-ethyl-5,6,7,8-tetrahydroquinoline (A)], there was obtained in 45% yield 2-ethyl-4-[(4'-methoxy-2'-(1H-tetrazol-5-yl)biphenyl-4-yl)methoxy]-5,6,7,8-tetrahydroquinoline hydrochloride, m.p. 207°–208° C.; NMR (d$_6$-DMSO): 1.3(t,3H), 1.7–1.9(m,4H), 2.55–2.7(m,2H), 2.85–3.05(m,4H), 3.9(s,3H), 5.4(s,2H), 7.1(d,2H), 7.2–7.3(m,2H), 7.35–7.55(m,4H); mass spectrum (+ve FAB, DMSO/m-nitrobenzyl alcohol): 442 (M+H)$^+$; microanalysis, found: C,63.8; H,6.0; N,14.1%; C$_{26}$H$_{27}$N$_5$O$_2$.HCl.0.5H$_2$O requires: C,64.1; H,6.0; N,14.4%.

Compound A was obtained in a yield of 37% using an analogous procedure to that described in Example 36, part (iii), as follows:

(Example 37A): 4-[(2'-Cyano-4'-methoxybiphenyl-4-yl)methoxy]-2-ethyl-5,6,7,8-tetrahydroquinoline, as a foam: NMR (CDCl$_3$): 1.3(t,3H), 1.7–1.9(m,4H), 2.65–2.75(m,2H), 2.8(q,2H), 2.85–2.95(m,2H), 3.9(s,3H), 5.2(s,2H), 6.6(s,1H), 7.2(dd,1H), 7.25(d,1H), 7.4(d,1H), 7.45–7.55(m,4H); starting from 2-bromo-5-methoxybenzonitrile, itself obtained in 55% yield as a solid, m.p. 135°–137° C.; NMR (CDCl$_3$): 3.8(s,3H), 7.0(dd,1H), 7.15(d,1H), 7.5(d,1H); using an analogous procedure to that described in Example 36, part (ii), starting from 2-bromo-5-methoxybenzoic acid.

EXAMPLE 38

Using an analogous procedure to that described in Example 36, but starting from 4-[(5'-methoxy-2'-(2-tributylstannyl-2H-tetrazol-5-yl)biphenyl-4-yl)methoxy]-2-ethyl-5,6,7,8-tetrahydroquinoline [prepared as a solution in xylene using a similar procedure to that described in Example 36 but starting from 4-[(2'-cyano-5'-methoxybiphenyl-4-yl)methoxy]-2-ethyl-5,6,7,8-tetrahydroquinoline (A)] there was obtained in 42% yield 2-ethyl-4-[(5'-methoxy-2'-(1H-tetrazol-5-yl)biphenyl-4-yl)methoxy]-5,6,7,8-tetrahydroquinoline hydrochloride, m.p. 237°–238° C.; NMR (d$_6$-DMSO): 1.3(t,3H), 1.7–1.9(m,4H), 2.55–2.65(m,2H), 2.85–3.0(m,4H), 3.9(s,3H), 5.45(s,2H), 7.05(d,1H), 7.1–7.25(m,3H), 7.4–7.5(m,3H), 7.6(d,1H); mass spectrum (+ve FAB, m-nitrobenzyl alcohol): 442 (M+H)$^+$; microanalysis, found: C,63.8; H,6.0; N,14.1%; C$_{26}$H$_{27}$N$_5$O$_2$.HCl.0.5-H$_2$O requires: C,64.0; H,6.0; N,14.4%.

Compound A was obtained as follows:

(i) Trifluoromethanesulphonic anhydride (2.06 g) was added dropwise to a solution of 2-cyano-5-methoxyphenol (1.0 g) in dry pyridine (20 ml) at 0° C. under an atmosphere of argon. Volatile material was removed by evaporation and the residue was dissolved in ethyl acetate (30 ml). The solution was washed with water (60 ml) and saturated sodium chloride solution (30 ml) and dried (MgSO$_4$). The solvent was removed by evaporation and the residue purified by flash chromatography, eluting with ethyl acetate/hexane (1:3 v/v), to give (2-cyano-5-methoxyphenyl)trifluoromethanesulphonate (1.53 g) as an oil; NMR (CDCl$_3$): 3.9(s,3H), 6.95(d,1H), 7.0(d,1H), 7.7(d,1H).

(ii) Using an analogous procedure to that described in Example 36, part (iii), but starting from (2-cyano-5-methoxyphenyl)trifluoromethanesulphonate in place of compound B therein, there was obtained in 49% yield 4-[(2'-cyano-5'-methoxybiphenyl-4-yl)methoxy]-2-ethyl-5,6,7,8-tetrahydroquinoline (A), m.p. 136°–137° C.; NMR (CDCl$_3$): 1.3(t,3H), 1.7–1.95(m,4H), 2.65–2.75(m,2H), 2.8(q,2H), 2.85–2.95(m,2H), 3.7(s,3H), 5.2(s,2H), 6.6(s,1H), 6.9–7.05(m,2H), 7.5–7.6(m,4H), 7.7(d,1H).

EXAMPLES 39–40

Using an analogous procedure to that described in Example 36, but starting from the appropriate compound of formula III wherein L is tributylstannyl, the following compounds of formula I were obtained in yields of (16–69%):

(Example 39): 2-Ethyl-4-[(4'-methyl-2'-(1H-tetrazol-5-yl)biphenyl-4-yl)methoxy]-5,6,7,8-tetrahydroquinoline hydrochloride, m.p. 219°–221° C.; NMR (d$_6$-DMSO): 1.3(t,3H), 1.7–1.9(m,4H), 2.4(s,3H), 2.55–2.65(m,2H), 2.85–3.05(m,4H), 5.4(s,2H), 7.1(d,2H), 7.4–7.6(m,6H); mass spectrum (+ve FAB, DMSO/m-nitrobenzyl alcohol): 426 (M+H)$^+$.

(Example 40): 2-Ethyl-4-[(6'-methyl-2'-(1H-tetrazol-5-yl)biphenyl-4-yl)methoxy]-5,6,7,8-tetrahydroquinoline hydrochloride, m.p. 218°–220° C.; NMR (d$_6$-DMSO): 1.3(t,3H), 1.7–1.9(m,4H), 2.1(s,3H), 2.6–2.7(m,2H), 2.95(q,2H), 3.0–3.1m,2H), 5.5(s,2H), 7.1(d,2H), 7.3–7.6 (complex m,6H); mass spectrum (+ve FAB, DMSO/m-nitrobenzyl alcohol): 426

(M+H)+; microanalysis, found: C,65.9; H,6.1; N,14.8%; $C_{26}H_{27}N_5O\cdot HCl\cdot 0.5H_2O$ requires: C,66.2; H,6.2; N,14.9%.

The necessary starting materials of formula III (L is tributylstannyl) used in Examples 39–40 were obtained as a solution in xylene using a similar procedure to that described in Example 36, starting from the appropriate nitriles corresponding to compound A in Example 36. The nitriles were obtained in yields of 43–57% using an analogous procedure to that described in Example 38, part (ii) as follows:

(Example 39A): 4-[(2'-Cyano-4'-methylbiphenyl-4-yl)methoxy]-2-ethyl-5,6,7,8-tetrahydroquinoline, m.p. 161°–162° C.; NMR (CDCl$_3$): 1.3(t,3H), 1.7–1.95(m,4H), 2.4(s,3H), 2.7(t,2H), 2.8(q,2H), 2.9(t,2H), 5.2(s,2H), 6.6(s,1H), 7.35–7.6 (complex m,7H); starting from (2-cyano-4-methylphenyl)trifluoromethanesulphonate, itself obtained as an oil in 52% yield [NMR (CDCl$_3$): 2.4(s,3H), 7.4(d,1H), 7.45–7.6(m,2H)], using an analogous procedure to that described in Example 38, part (i), starting from 2-cyano-4-methylphenol.

(Example 40A): 4-[2'-Cyano-6'-methylbiphenyl-4-yl)methoxy]-2-ethyl-5,6,7,8-tetrahydroquinoline, m.p. 146°–148° C.; NMR (CDCl$_3$): 1.3(t,3H), 1.75–1.95(m,4H), 2.2(s,3H), 2.65–2.85(m,4H), 2.8–2.9(m,2H), 5.2(s,2H), 6.6(s,1H), 7.2–7.65 (complex m,7H); starting from (2-cyano-6-methylphenyl)trifluoromethanesulphonate, itself obtained as an oil in 80% yield [NMR (CDCl$_3$): 2.5(s,3H), 7.4(t,1H), 7.55–7.65(m,2H)], using an analogous procedure to that described in Example 38, part (i), starting from 2-cyano-6-methylphenol.

EXAMPLE 41

Using an analogous procedure to that described in Example 36, but starting from 4-[(2-fluoro-2'-(2-tributylstannyl-2H-tetrazol-5-yl)biphenyl-4-yl)methoxy]-2-ethyl-5,6,7,8-tetrahydroquinoline [prepared as a solution in xylene using a similar procedure to that described in Example 36 but starting from 4-[(2'-cyano-2-fluorobiphenyl-4-yl)methoxy]-2-ethyl-5,6,7,8-tetrahydroquinoline (A)], there was obtained in 41% yield 2-ethyl-4-[(2-fluoro-2'-(1H-tetrazol-5-yl)biphenyl-4-yl)methoxy]-5,6,7,8-tetrahydroquinoline hydrochloride, m.p. 206°–208° C.; NMR (d$_6$-DMSO): 1.3(t,3H), 1.65–1.9(m,4H), 2.6(q,2H), 2.9–3.05(m,4H), 5.5(s,2H), 6.95(1H,dd), 7.1(1H,dd), 7.5–7.8 (complex m,6H); mass spectrum (DMSO/m-nitrobenzyl alcohol): 430(M+H)+.

Compound A was obtained as follows:

(i) A suspension of 2-ethyl-5,6,7,8-tetrahydro-4(1H)-quinolone (1.06 g) in DMF (10 ml) was added to sodium hydride (60% dispersion in oil, 364 mg) in DMF (10 ml) under an atmosphere of argon. The mixture was stirred for 30 minutes and then a solution of 4-bromo-2-fluorobenzyl bromide (1.6 g) in DMF (5 ml) was added. Stirring was continued for 18 hours and volatile material was removed by evaporation. The residue was partitioned between ethyl acetate (30 ml) and water (30 ml) and the organic layer was separated, washed with saturated sodium chloride solution (30 ml) and dried (MgSO$_4$). The solvent was removed by evaporation and the residue was purified by flash chromatography, eluting with ethyl acetate/hexane (1:1 v/v), to give [4-(4-bromo-2fluorophenyl)methoxy]-2-ethyl-5,6,7,8-tetrahydroquinoline (B) (1.7 g) as an oil; NMR (CDCl$_3$): 1.3(t,3H), 1.7–1.9(m,4H), 2.6–2.9(m,6H), 5.1(s,2H), 6.5(s,1H), 7.25–7.4(m,3H).

(ii) A mixture of compound B (1.46 g), 2-cyanophenylboronic acid [prepared from 2-bromobenzonitrile using an analogous procedure to that described in Example 55, part (ii); m.p. >220° C.; NMR (d$_6$-DMSO): 7.4–7.9(complex m)](0.62 g), tetrakis(triphenylphosphine)palladium and triethylamine (10 ml) in DMF (20 ml) was stirred at 90° C. for 20 hours. Volatile material was removed by evaporation and the residue was partitioned between ethyl acetate (30 ml) and water (30 ml). The organic phase was separated, washed with saturated sodium chloride solution (30 ml) and dried (MgSO$_4$). The solvent was removed by evaporation and the residue was purified by flash chromatography, eluting with ethyl acetate/hexane (3:2 v/v) to give 4-[(2'-cyano-2-fluorobiphenyl-4-yl)methoxy]-2-ethyl-5,6,7,8-tetrahydroquinoline (A) (325 mg) as an oil; NMR 1.3(t,3H), 1.8–1.9(m,4H), 2.7–2.9(m,6H), 5.2(s,2H), 6.6(s,1H), 7.2–7.9(complex m,7H).

EXAMPLE 42

Using an analogous procedure to that described in Example 36, but starting from 4-[(3-chloro-2'-(2-tributylstannyl-2H-tetrazol-5-yl)biphenyl-4-yl)methoxy]-2-ethyl-5,6,7,8-tetrahydroquinoline [prepared as a solution in xylene using a similar procedure to that described in Example 36 but starting from 4-[(3-chloro-2'-cyanobiphenyl-4-yl)methoxy]-2-ethyl-5,6,7,8-tetrahydroquinoline (A)], there was obtained in 60% yield 2-ethyl-4-(3-chloro-2'-(1H-tetrazol-5-yl)biphenyl-4-yl)methoxy]-5,6,7,8-tetrahydroquinoline hydrochloride, m.p. 194°–197° C.; NMR (d$_6$-DMSO): 1.3(t,3H), 1.75–1.85(m,4H), 2.6–2.7(m,2H), 2.9–3.05(m,4H), 5.5(s,2H), 7.35–7.75 (complex m,7H), 7.85–7.95(m,1H); mass spectrum (+ve FAB, DMSO/m-nitrobenzyl alcohol): 416 (M+H)+; microanalysis, found: C,61.7; H,5.5; N,14.1%; $C_{25}H_{24}ClN_5O\cdot HCl$ requires: C,62.2; H,5.2; N,14.5%.

Compound A was obtained as follows:

(i) Using an analogous procedure to that described in Example 38, part (i), but starting from 2-chloro-4-methylphenol, there was obtained in 87% yield (2-chloro-4-methylphenyl)trifluoromethanesulphonate (D) as an oil; NMR (CDCl$_3$): 2.4(s,3H), 7.1–7.35(m,3H).

(ii) Using an analogous procedure to that described in Example 41, part (ii), but starting from compound (D), there was obtained in 55% yield (2'-chloro-4'-methyl)biphenyl-2-carbonitrile (C) as an oil; 2.4(s,3H), 7.15–7.8 (complex m,6H).

(iii) Using an analogous procedure to that described in Example 35, part (ii), but starting from compound (C), there was obtained in 67% yield (4'-bromomethyl-2'-chloro)biphenyl-2-carbonitrile (B), as an oil; NMR (CDCl$_3$): 4.5(s,2H), 7.3–7.8 (complex m,7H).

(iv) Using an analogous procedure to that described in Example 1, but starting from compound (B) and 2-ethyl-5,6,7,8-tetrahydro-4(1H)-quinolone, there was obtained in 56% yield 4-[(3-chloro-2'-cyanobiphenyl-4-yl)methoxy]-2-ethyl-5,6,7,8-tetrahydroquinoline (A), as a foam; NMR (CDCl$_3$): 1.3(t,3H), 1.7–1.95(m,4H), 2.7–2.9(m,6H), 5.1(s,2H), 6.5(s,1H), 7.35–7.8 (complex m,7H).

EXAMPLE 43

Using an analogous procedure to that described in Example 1, but starting from 2-ethyl-6,7,8,9-tetrahydro-4-[2'-(2-triphenylmethyl-2H-tetrazol-5-yl)biphenyl-4- yl)methoxy]-5H-cyclohepta[b]pyridine (A) there was obtained in 69% yield 2-ethyl-6,7,8,9-tetrahydro-4-[(2'-(1H-tetrazol-5-yl)biphenyl-4-yl)methoxy]-5-cyclohepta[b]pyridine hydrochloride, m.p. 208-°211° C.; NMR (d$_6$-DMSO): 1.3(t,3H), 1.45-1.75(m,4H), 1.8-1.9(m,2H), 2.8-2.9(m,2H), 3.0(q,2H), 3.2-3.35(m,2H), 5.4(s,2H), 7.3(d,2H), 7.4-7.8(complex m,7H); mass spectrum (+ve FAB, DMSO/m-nitrobenzyl alcohol): 426 (M+H)$^+$; microanalysis, found C,67.8; H,6.2; N,15.1%; C$_{26}$H$_{27}$N$_5$O.HCl requires: C,67.6; H,6.2; N,15.2%.

The starting material A was obtained as follows:

(i) Using an analogous procedure to that described in Example 12A, but starting from 4-(1-cyclohepten-1-yl)morpholine, there was obtained in 9% yield 2-ethyl-1,5,6,7,8,9-hexahydro-4(1H)-cyclohepta[b]pyridone (B), m.p. 196-°198° C.; NMR (d$_6$-DMSO): 1.1(t,3H), 1.3-1.5(m,2H), 1.5-1.65(m,2H), 1.7-1,85(m,2H), 2.4(q,2H), 2.55-2.6(m,2H), 2.65-2.85(m,2H), 5.8(s,1H), 10.8(br s, 1H).

(ii) Using an analogous procedure to that described in Example 1, but starting from compound B, there was obtained in 76% yield 2-ethyl-6,7,8,9-tetrahydro-4-[(2'-(2-triphenylmethyl-2H-tetrazol-5-yl) biphenyl-4-yl)methoxy]-5H-cyclohepta[b]pyridine (A) as a foam; NMR (CDCl$_3$): 1.3(t,3H), 1.5-1.6(m,2H), 1.65-1.75(m,2H), 1.8-1.9(m,2H), 2.75(q,2 h), 2.8-2.9(m,2H), 3.0-3.1(m,2H), 5.0(s,2H), 6.6(s,1H), 6.9-6.95(m,6H), 7.15-7.55 (complex m,16H), 7.9-8.0(m,1H).

EXAMPLE 44

Using an analogous procedure to that described in Example 1, but starting from 6,7-dihydro-3-methoxycarbonyl-2-methyl-4-[(2'-(2-triphenylmethyl-2H-tetrazol-5-yl)biphenyl-4-yl)methoxy]-5H-cyclopenta[b]pyridine (A), there was obtained in 53% yield 6,7-dihydro-3-methoxycarbonyl-2-methyl-4-[(2'-(1H-tetrazol-5-yl)biphenyl-4-yl)methoxy]-5H-cyclopenta[b]pyridine hydrochloride, m.p. 163°-164° C.; NMR (d$_6$-DMSO): 2.1-2.2(m,2H), 2.5(s,3H), 3.1(t,2H), 3.4(t,2H), 3.8(s,3H), 5.6(s,2H), 7.1(dd,2H), 7.3(d,2H), 7.45-7.55(m,4H); mass spectrum (+ve FAB, DMSO/m-nitrobenzyl alcohol): 442 (M+H)$^+$; microanalysis, found: C,60.5; H,5.2; N,14.2; H$_2$O, 3.8%; C$_{25}$H$_{23}$N$_5$O$_3$.HCl.H$_2$O requires: C,60.5; H,5.3; N,14.1; H$_2$O 3.6%.

The starting material A was obtained using an analogous procedure to that described in Example 1, but starting from 3-methoxycarbonyl-2-methyl-1,5,6,7-tetrahydro-4(1H)-cyclopenta[b]pyridone (obtained as described in *Heterocycles*, 1982, 13, 239), as a foam, in 66% yield; NMR (CDCl$_3$): 2.05-2.15(m,2H), 2.5(s,1H), 2.95-3.1(m,4H), 3.8(s,3H), 5.1(s,2H), 6.85-6.95(m,6H), 7.25-7.55 (complex m,16H), 7.9-7.95(m,1H).

EXAMPLE 45

4-[(2-Ethyl-5,6,7,8-tetrahydroquinolin-4-yloxy)methyl]benzoic acid (A) (400 mg) was added to a solution of o-toluenesulphonamide (222 mg), 4-dimethylaminopyridine (159 mg) and 1-[3-(dimethylamino)propyl]-3-ethylcarbodiimide hydrochloride (250 mg) in dichloromethane (20 ml). The mixture was stirred for 20 hours and then diluted with dichloromethane (20 ml). The solution was washed with water (3×10 ml) and then dried (MgSO$_4$). The solvent was removed by evaporation and the residue was dissolved in a hot mixture of satured sodium bicarbonate solution (20 ml), water (20 ml) and ethanol (5 ml). Insoluble material was removed by filtration and the hot solution was acidified to pH 4 with 1M citric acid solution. The resultant precipitate was collected by filtration to give 4-[(2-ethyl-5,6,7,8-tetrahydroquinolin-4-yloxy)methyl]-N-(2-methylphenyl)-sulphonylbenzamide, m.p. 266°-268° C.; NMR (d$_6$-DMSO): 1.2(t,3H), 1.7-1.8(m,4H), 2.5(s,3H), 2.55-2.65(m,2H), 2.75(q,2H), 2.8-2.9(m,2H), 5.4(s,2H), 7.2-7.4(m,4H), 7.45(d,2H), 7.85(s,1H), 7.95(d,2H); mass spectrum (−ve FAB, DMSO/CH$_3$OH/m-nitrobenzyl alcohol): 463 (M−H)$^-$; microanalysis, found: C,67.2; H,6.2; N,6.0%; C$_{26}$H$_{28}$N$_2$O$_4$S requires: C,67.2; H,6.1; N,6.0%.

The starting material A was obtained as follows:

(i) Using an analogous procedure to that described in Example 1, but starting from 2-ethyl-5,6,7,8-tetrahydro-4(1H)-quinolone and methyl 4-(bromomethyl)benzoate and purifying the product by flash chromatography eluting with methane/dichloromethane (1:49 v/v), there was obtained in 67% yield methyl 4-[(2-ethyl-5,6,7,8-tetrahydroquinolin-4-yloxy)methyl]benzoate (B), m.p. 79°-80° C.; NMR (CDCl$_3$): 1.3(t,3H), 1.75-1.95(m,4H), 2.65-2.8(m,4H), 2.85-2.95(m,4H), 3.9(s,3H), 5.2(s,2H), 6.5(s,1H), 7.5(d,2H), 8.1(d,2H).

(ii) 1M Sodium hydroxide solution (6 ml) was added to a solution of compound B (640 mg) in ethanol (10 ml). The mixture was stirred for 4 hours and then volatile material was removed by evaporation. The residue was dissolved in water (20 ml) and the solution was acidified to pH 4 with 1M citric acid solution. The resultant precipitate was collected by filtration to give 4-[(2-ethyl-5,6,7,8-tetrahydroquinolin-4-yloxy)methyl]-benzoic acid (A) (463 mg), m.p. 246°-249° C.; NMR (d$_6$-DMSO): 1.2(t,3H), 1.65-1.95(m,4H), 2.55-2.75(m,6H), 5.25(s,2H), 6.7(s,1H), 7.55(d,2H), 7.95(d,2H).

EXAMPLE 46

Using an analogous procedure to that described in Example 45, but starting from 4-[(2,6-diethyl-3-methoxycarbonylpyridin-4-yl-oxy)methyl]benzoic acid (A) there was obtained in 27% yield 4-[(2,6-diethyl-3-methoxycarbonylpyridin-4-yloxy)methyl]-N-(2-methylphenyl)sulphonylbenzamide, m.p. 175°-176° C.; NMR (d$_6$-DMSO): 1.15(t,3H), 1.2(t,3H), 2.55-2.75(m,7H), 5.3(s,2H), 7.0(s,1H), 7.35-7.6(m,5H), 7.9(d,2H), 8.05(dd,1H), 12.7(br s, 1H); mass spectrum (+ve FAB, CH$_3$OH/m-nitrobenzyl alcohol): 497 (M+H)$^+$; microanalysis, found: C,62.4; H,5.8; N,5.5%; C$_{26}$H$_{28}$N$_2$O$_6$S requires: C,62.9; H,5.7; N,5.6%.

The starting material A was obtained as follows:

(i) Using an analogous procedure to that described in Example 45, part (i), but starting from methyl 2,6-diethyl-1,4-dihydro-4-oxopyridine carboxylate, there was obtained in 75% yield methyl 4-[(2,6-diethyl-3-3-methoxycarbonylpyridin-4-yloxy)methyl]benzoate (B), m.p. 56°-57° C.; NMR (CDCl$_3$): 1.25(t,3H), 1.3(t,3H), 2.7-2.8(m,4H), 3.9(s,3H), 3.95(s,3H), 5.2(s,2H), 6.6(s,1H), 7.45(d,2H), 8.05(d,2H).

(ii) Using an analogous procedure to that described in Example 45, part (ii), but starting from compound B of part (i) of this example, there was obtained in 90% yield 4-[(2,6-diethyl-3-methoxycarbonylpyridin-4-yloxy)methyl]benzoic acid (A), m.p. 226°-228° C.; NMR (d$_6$-DMSO): 1.15(t,3H), 1.2(t,3H), 2.5-2.75(m,4H), 3.8(s,3H), 5.3(s,2H), 7.5(d,2H), 8.0(d,2H).

EXAMPLES 47-48

Using an analogous procedure to that described in Example 35, but starting from the appropriate compound of formula II wherein Q is methoxycarbonyl, the following compounds of formula I were obtained in yields of 35–60%:

(Example 47): 4'-[(2,6-Diethyl-3-methoxycarbonylpyridin-4-yloxy)methyl]biphenyl-2-carboxylic acid, m.p. 181°–182° C.; NMR (d$_6$-DMSO): 1.4(t,3H), 1.5(t,3H), 2.55–2.65(m,4H), 3.8(s,3H), 5.3(s,2H), 7.0(s,1H), 7.35–7.6 (complex m,7H), 7.8(dd,1H); mass spectrum (+ve FAB, DMSO/m-nitrobenzyl alcohol): 420 (M+H)$^+$; microanalysis, found: C,71.1; H,6.1; N,3.2%; C$_{25}$H$_{25}$NO$_5$ requires: C,71.6; H,6.1; N,3.2%.

(Example 48): 4'-[(2,6-Dimethyl-3-phenylpyridin-4-yloxy)methyl]biphenyl-2-carboxylic acid, m.p. 231°–234° C.; NMR (d$_6$-DMSO, d$_4$-acetic acid): 2.1(s,3H), 2.35(s,3H), 5.1(s,2H), 6.95(s,1H), 7.15–7.45 (complex m,12H), 7.6(dd,1H); mass spectrum (+ve FAB, DMSO/m-nitrobenzyl alcohol): 410 (M+H)$^+$; microanalysis, found: C, 76.6; H,6.1; N,3.2%; C$_{27}$H$_{23}$NO$_3$.0.6CH$_3$OH requires: C,76.8; H,5.9; N,32.2%.

The necessary starting materials of formula II used in Examples 47–48 were obtained in yields of 61–74% using an analogous procedure to that described in Example 35, part (iii), as follows:

(Example 47A): Methyl 4'-[(2,6-diethyl-3-methoxycarbonylpyridin-4-yloxy)methyl]biphenyl-2-carboxylate, m.p. 89°–90° C.; NMR (CDCl$_3$): 1.3(2×t,6H), 2.7–2.8(m,4H), 3.6(s,3H), 3.9(s,3H), 5.2(s,2H), 6.6(s,1H), 7.2–7.55 (complex m,7H), 7.8(dd,1H); starting from 2,6-diethyl-1,4-dihydro-4-oxopyridine-3-carboxylate.

(Example 48A): Methyl 4'-[2,6-dimethyl-3-phenylpyridin-4-yloxy)methyl]biphenyl-2-carboxylate, m.p. 118°–120° C.; NMR (CDCl$_3$): 2.3(s,3H), 2.55(s,3H), 3.6(s,3H), 5.1(s,2H), 6.7(s,1H), 7.15–7.5 (complex m,12H), 7.8(dd,1H); starting from 2,6-dimethyl-3-phenyl-4(1H)-pyridone.

EXAMPLES 49–51

Using an analogous procedure to that described in Example 1, but starting from the appropriate compound of formula III wherein L is triphenylmethyl and recrystallising the products from a mixture of isopropanol and ether, the following compounds of formula I were obtained in yields of 79–87%:

(Example 49): 3-Acetamidomethyl-2,6-dimethyl-4-[(2'-(1H-tetrazol-5-yl)biphenyl-4-yl)methoxy]pyridine hydrochloride, m.p. 208°–210° C. (softens from 150° C.); NMR (d$_6$-DMSO): 1.8(s,3H), 2.65(s,3H), 2.75(s,3H), 4.3(br d, 2H), 5.5(s,2H), 7.15(d,2H), 7.4–7.75 (complex m,7H), 8.2(br t, 1H); mass spectrum (+ve FAB, DMSO/m-nitrobenzyl alcohol): 429 (M+H)$^+$; microanalysis, found: C,60.1; H,6.1; N,15.7%; C$_{24}$H$_{24}$N$_6$O$_2$.HCl requires: C,59.7; H,6.3; N,15.8%.

(Example 50): 3-Benzamidomethyl-2,6-dimethyl-4-[(2'-(1H-tetrazol-5-yl)biphenyl-4-yl)methoxy]pyridine hydrochloride, m.p. 220°–221° C; NMR (d$_6$-DMSO): 2.7(s,3H), 2.8(s,3H), 4.5(d,2H), 5.5(s,2H), 7.05(d,2H), 7.4–7.7 (complex m,10H), 7.8(d,2H); mass spectrum (+ve FAB, DMSO/m-nitrobenzyl alcohol): 491 (M+H)$^+$; microanalysis, found: C,65.9; H,5.4; N,15.1%; C$_{29}$H$_{26}$N$_6$O$_2$.HCl.0.6.C$_3$H$_7$OH requires: C,65.6; H,5.6; H,14.9%.

(Example 51): 2,6-Dimethyl-3-(ethylaminocarbonylamino)methyl-4-[(2'-(1H-tetrazol-5-yl)biphenyl-4-yl)methoxy]pyridine hydrochloride, m.p. 170°–190° C.; NMR (d$_6$-DMSO): 0.95(t,3H), 2.65(s,3H), 2.8(s,3H), 2.9–3.0(m,2H), 4.25(br d, 1H), 5.5(s,2H), 6.15(br t, 1H), 6.25(br t, 1H), 7.15(d,2H), 7.45–7.75 (complex m,7H); mass spectrum (+ve FAB, DMSO/m-nitrobenzyl alcohol): 458 (M+H)$^+$.

The necessary starting materials of formula III (wherein L is triphenylmethyl) used in Examples 49–51 were obtained as follows:

(Example 49A): A solution of acetyl chloride (79 mg) in dichloromethane (1 ml) was added to a solution of 3-aminomethyl-2,6-dimethyl-4-[(2'-(2-triphenylmethyl-2H-tetrazol-5-yl)biphenyl-4-yl)methoxy]pyridine (628 mg) and triethylamine (101 mg) in dichloromethane (15 ml). The solution was left to stand for 1 hour and then water (15 ml) was added. The organic phase was separated, washed with saturated sodium chloride solution (15 ml) and then dried (MgSO$_4$). The solvent was removed by evaporatoion and the residue was purified by flash chromatography, eluting with methanol/dichloromethane (1:19 v/v) to give 3-acetamidomethyl-2,6-dimethyl-4-[(2'-(2-triphenylmethyl-2H-tetrazol-5-yl)biphenyl-4-yl)methoxy]pyridine (594 mg), as a foam; NMR (CDCl$_3$): 1.8(s,3H), 2.5(s,3H), 2.6(s,3H), 4.45(d,2H), 5.0(s,2H), 5.6(br t, 1H), 6.6(s,1H), 6.9–7.0(m,6H), 7.25–7.6 (complex m,16H), 7.95(dd,1H).

(Example 50A): Using an analogous procedure to that described in Example 49A, but substituting an equimolar amount of benzoyl chloride for acetyl chloride, there was obtained in 90% yield 3-benzamidomethyl-2,6-dimethyl-4-[2'-(2-triphenylmethyl-2H-tetrazol-5-yl)biphenyl-4-yl)methoxy]pyridine, as a foam; NMR (CDCl$_3$): 2.5(s,3H), 2.8(s,3H), 4.7(d,2H), 5.05(s,2H), 6.4(br t, 1H), 6.65(s,1H), 6.9–7.0(m,6H), 7.15–7.65 (complex m,21H), 7.95(dd,1H).

(Example 51A): A solution of ethyl isocyanate (71 mg) and 3-aminomethyl-2,6-dimethyl-4-[(2'-(2-triphenylmethyl-2H-tetrazol-5-yl) biphenyl-4-yl)methoxy]pyridine (628 mg) in dichloromethane (15 ml) was left to stand for 2 hours. The solvent was removed by evaporation and the residue was purified by flash chromatography, eluting with methanol/dichloromethane (7:93 v/v), to give 2,6-dimethyl-3-(ethylaminocarbonylamino)methyl-4-[(2'-(2-triphenylmethyl-2H-tetrazol-5-yl)biphenyl-4-yl)methoxy]pyridine (602 mg), as a foam: NMR (CDCl$_3$): 1.0(t,3H), 2.5(s,3H), 2.65(s,3H), 3.0–3.1(m,2H), 4.1(br t, 1H), 4.4(d,2H), 4.5(br d, 1H), 5.0(s,2H), 6.6(s,2H), 6.8–7.0(m,6H), 7.1–7.55 (complex m,16H), 7.9(dd,1H).

EXAMPLE 52

Using an analogous procedure to that described in Example 1, but starting from 2,6-dimethyl-N-propyl-4-[(2'-(2-triphenylmethyl-2H-tetrazol-5-yl)biphenyl-4-yl)methoxy]pyridine-3-carboxamide (A), there was obtained in 73% yield 2,6-dimethyl-N-propyl-4-[(2'-(1H-tetrazol-5-yl)biphenyl-4-yl)methoxy]pyridine-3-carboxamide, m.p. 196°–198° C.; NMR (d$_6$-DMSO): 0.8(t,3H), 1.4–1.5(m,2H), 2.6(s,3H), 2.7(s,3H), 3.1–3.3(m,2H), 5.4(s,2H), 7.15(dd,2H), 7.4(dd,2H), 7.5–7.8 (complex m,5H), 8.65(t,1H); mass spectrum (+ve FAB, DMSO/m-nitrobenzyl alcohol): 443 (M+H)$^+$; microanalysis, found: C,62.8; H,5.9; N,17.0; Cl,6.9; H$_2$O,0.6%; C$_{25}$H$_{25}$N$_6$O$_2$.HCl.0.1H$_2$O requires: C,62.4; H,5.5; N,17.5; Cl,7.4; H$_2$O,0.4%.

The starting material A was obtained as follows:

(i) Propylamine (1.48 g) was added dropwise to a 2M solution of trimethyl aluminium in toluene (12.5 ml) under an atmosphere of argon. When evolution of methane ceased, the solution was transferred by syringe to a stirred suspension of ethyl 1,4-dihydro-2,6-dimethyl-4-oxopyridine-3-carboxylate (1.95 g) in toluene (25 ml). The resulting yellow solution was heated at 100° C. for 2 hours and then cooled to 0° C. Methanol (10 ml) was added dropwise and the mixture was diluted with dichloromethane and stirred for 1 hour. The mixture was filtered through a pad of diatomaceous earth, which was then washed with methanol (100 ml). The combined filtrate and washings were concentrated and the residue was purified by flash chromatography, eluting with methanol/dichloromethane (3:17 v/v), to give 1,4-dihydro-2,6-dimethyl-N-propyl-4-oxopyridine-3-carboxamide (B) (0.73 g), m.p. 62°–65° C.; NMR (CDCl$_3$): 0.95(t,3H), 1.5–1.7(m,2H), 2.3(s,3H), 2.8(s,3H), 3.3–3.4(m,2H), 6.3(s,1H), 10.55(br t, 1H), 11.5(br s, 1H).

(ii) Using an analogous procedure to that described in Example 1, but starting from compound B of part (i) of this example, there was obtained in 71% yield 2,6-dimethyl-N-propyl-4-[(2'-(2-triphenylmethyl-2H-tetrazol-5-yl)-biphenyl-4-yl)methoxy]pyridine-3-carboxamide (A) as a foam; NMR (CDCl$_3$): 0.9(t,3H), 1.4–1.6(m,2H), 2.6(s,3H), 3.35(q,2H), 5.0(s,2H), 6.6(s,1H), 6.9–7.0(m,6H), 7.2–7.55 (complex m,16H), 7.9(dd,1H).

EXAMPLE 53

Using an analogous procedure to that described in Example 1, but starting from 2,6-dimethyl-3-iodo-4-[(2'-(2-triphenylmethyl-2H-tetrazol-5-yl)biphenyl-4-yl)methoxy]pyridine, there was obtained in 42% yield 2,6-dimethyl-3-iodo-4-[(2'-(1H-tetrazol-5-yl)biphenyl-4-yl)methoxy]pyridine, m.p. 237°–245° C. (decomposition); NMR (d$_6$-DMSO): 2.6(s,3H), 2.8(s,3H), 5.5(s,2H), 7.2(d,2H), 7.4–7.85 (complex m,7H); mass spectrum (+ve FAB, DMSO/m-nitrobenzyl alcohol): 484 (M+H)$^+$; microanalysis, found: C,47.1; H,3.6; N,12.7%; C$_{21}$H$_{18}$IN$_5$O HCl.H$_2$O requires: C,46.9; H,3.9; N,13.0%.

The starting material A was obtained using an analogous procedure to that described in Example 1, but starting from 2,6-dimethyl-3-iodo-4(1H)-pyridone (itself obtained as described in Chem. Pharm. Bull., 1986, 34, 2719), as a solid, in 62% yield; m.p. 149°–152° C.; NMR (CDCl$_3$): 2.5(s,3H), 2.8(s,3H), 5.1(s,2H), 6.4(s,1H), 6.9–7.0(m,6H), 7.1–7.6 (complex m,16H), 7.9–8.0(m,1H).

EXAMPLE 54

Using an analogous procedure to that described in Example 1, but starting from 2,6-diethyl-3-iodo-4-[(2'-(2-triphenylmethyl-2H-tetrazol-5-yl)biphenyl-4-yl)methoxy]pyridine (A), there was obtained in 38% yield 2,6-diethyl-3-iodo-4-[(2'-(1H-tetrazol-5-yl)biphenyl-4-yl)methoxy]pyridine, m.p. 201°–205° C. (decomposition); NMR (d$_6$-DMSO): 1.2–1.3(m,6H), 2.9(q,2H), 3.15(q,2H), 5.5(s,2H), 7.2(d,2H), 7.4(s,1H), 7.5(d,2H), 7.55–7.75(m,4H); mass spectrum (+ve FAB, DMSO/m-nitrobenzyl alcohol): 512 (M+H)$^+$; microanalysis, found: C,50.3; H,4.3; N,12.8%; C$_{23}$H$_{23}$IN$_5$O.HCl requires: C,50.4; H,4.2; N,12.8%.

The starting material A was obtained as follows:

(i) 2M Sodium hydroxide (30 ml) was added to a solution of methyl 2,6-diethyl-1,4-dihydro-4-oxopyridine-3-carboxylate in methanol (60 ml) and the solution was heated under reflux for 48 hours. Volatile material was removed by evaporation and the residue was dissolved in water (50 ml). The solution was washed with ethyl acetate and acidified to pH 4 with 1M citric acid solution. The resultant precipitate was collected by filtration to give 2,6-diethyl-1,4-dihydro-4-oxopyridine-3-carboxylic acid (B) (2.1 g), m.p. 238°–240° C. (decomposition); NMR (CDCl$_3$): 1.3(t,6H), 2.7(q,2H), 3.3(q,2H), 6.45(s,1H), 12.1(br s, 1H).

(ii) Compound B (1.0 g) was heated at 250° C. in a sublimation apparatus. The sublimate was collected and purified by flash chromatography, eluting with methanol/dichloromethane (1:9 v/v), to give 2,6-diethyl-4(1H)-pyridone (C) (0.58 g), m.p. 103°–110° C.; NMR (CDCl$_3$): 1.3(t,6H), 2.7(q,4H), 6.2(s,2H), 12.3–13.0(br s, 1H).

(iii) Iodine (720 mg) was added to a solution of compound C (430 mg) and sodium hydroxide (120 mg) in water (15 ml) and the mixture was stirred for 1 hour. The precipitated solid was collected by filtration and purified by flash chromatography, eluting with methanol/dichloromethane (1:19 v/v), to give 2,6-diethyl-3-iodo-4(1H)-pyridone (D) (290 mg), m.p. 225°–227° C.; NMR (d$_6$-DMSO): 1.15(t,6H), 2.5(q,2H), 2.8(q,2H), 5.9(s,1H), 11.4(br s, 1H).

(iv) Using an analogous procedure to that described in Example 1, but starting from compound D, there was obtained in 82% yield 2,6-diethyl-3-iodo-4-[(2'-(2-triphenylmethyl-2H-tetrazol-5-yl)biphenyl-4-yl)methoxy]pyridine (A), m.p. 132°–136° C.; NMR (CDCl$_3$): 1.3(t,6H), 2.8(q,2H), 3.1(q,2H), 5.1(s,2H), 6.5(s,1H), 6.9–7.0(m,6H), 7.1–7.6 (complex m,16H), 7.9–8.0(m,1H).

EXAMPLE 55

Using an analogous procedure to that described in Example 1, but starting from 3-(4-cyanophenyl)-2,6-dimethyl-4-[(2'-(2-triphenylmethyl-2H-tetrazol-5-yl)biphenyl-4-yl)methoxy]pyridine (A), there was obtained in 78% yield 3-(4-cyanophenyl)-2,6-dimethyl-4-[(2'-(1H-tetrazol-5-yl)biphenyl-4-yl)methoxy]pyridine hydrochloride, m.p. 142°–146° C.; NMR (d$_6$-DMSO): 2.15(s,3H), 2.45(s,3H), 5.1(s,2H), 7.0–7.1(m,3H), 7.1(d,2H), 7.5–7.7 (complex m,6H), 7.9(d,2H); mass spectrum (−ve FAB, DMSO/m-nitrobenzyl alcohol): 457 (M−H)$^−$; microanalysis, found: C,66.1; H,4.5; N,16.3%; C$_{28}$H$_{22}$N$_6$O.HCl.0.75H$_2$O requires: C,66.1; H,4.8; N,16.5%.

The starting material A was obtained as follows:

(i) 2,6-Dimethyl-3-iodo-4(1H)-pyridone (6.5 g) was added to a stirred suspension of sodium hydride (oil free; 1.04 g) in DMF (35 ml). When evolution of hydrogen ceased, benzyl chloride (3.3 g) was added. The mixture was heated at 50° C. for 3 hours and then left to stand for 20 hours. The mixture was added to water (150 ml) and the resultant precipitate collected by filtration to give 2,6-dimethyl-3-iodo-4-(phenylmethoxy)-pyridine (B) (5.7 g), m.p. 68°–70° C.; NMR (CDCl$_3$): 2.45(s,3H), 2.75(s,3H), 5.2(s,2H), 6.45(s,1H), 7.35–7.45(m,5H).

(ii) A 1.7M solution of t-butyllithium in pentane (35 ml) was added to a solution of 4-bromobenzonitrile (4.55 g) in THF (100 ml) at −78° C. under an atmosphere of argon. The solution was kept at −78° C. for 30 minutes and then trimethyl borate (2.91 g) was added. The solution was left to stand for 20 hours and then added to ice-cold 2M hydrochloric acid (100 ml). The mixture was extracted with ethyl acetate (3×100 ml) and the extracts were dried (MgSO$_4$). Volatile material was removed by evaporation and the residue was triturated with ethyl acetate/hexane (1:1 v/v) to give (4-cyanophenyl)boronic acid (C) (2.5 g), m.p. >250° C.; NMR (CDCl$_3$): 7.8(d,2H), 8.3(d,2H); microanalysis, found: C, 57.2; H,4.0; N,9.2%; C₇H₆BNO₂ requires: C,67.2; H,4.1; N,9.5%.

(iii) A solution of compound C (188 mg) in methanol (1 ml) was added to a mixture of compound B (170 mg), tetrakis(triphenylphosphine)palladium (30 mg), 2M sodium hydrogen carbonate solution (2 ml) and toluene (10 ml). The mixture was heated under reflux for 12 hours and then allowed to cool. Hydrogen peroxide solution (30 wt. % solution in water; 0.1 ml) was added and the mixture was stirred for 30 minutes. The aqueous phase was separated and extracted with ethyl acetate (2×25 ml). The combined organic solutions were dried (MgSO₄) and volatile material was removed by evaporation. The residue was purified by flash chromatography, eluting with ethyl acetate/hexane (4:1 v/v) to give 3-(4-cyanophenyl)-2,6-dimethyl-4-(phenylmethoxy)-pyridine (D), as a gum; NMR (CDCl₃): 2.3(s,3H), 2.6(s,3H), 5.1(s,2H), 6.7(s,1H), 7.1-7.2(m,2H), 7.25-7.35(m,5H), 7.7(d,2H).

(iv) A mixture of compound D (240 mg), ammonium formate (120 mg) and 10% palladium on charcoal catalyst (40 mg) in methanol (5 ml) was stirred for 2 hours. The catalyst was removed by filtration and the filtrate was concentrated. The residue was partitioned between dichloromethane (10 ml) and water (10 ml). The aqueous phase was separated and further extracted with dichloromethane (3×10 ml). The combined extracts were dried and the solvent was removed by evaporation. The residue was triturated with ether to give 3-(4-cyanophenyl)-2,6-dimethyl-4-(1H)-pyridone (E) (65 mg), as a non-crystalline solid; NMR (CDCl₃): 2.1(s,3H), 2.25(s,3H), 6.2(s,1H), 7.4(d,2H), 7.7(d,2H), 11.2(br s, 1H).

(v) Using an analogous procedure to that described in Example 1, but starting from compound E, there was obtained in 68% yield 3-(4-cyanophenyl)-2,6-dimethyl-4-[(2'-(2-triphenylmethyl-2H-tetrazol-5-yl)biphenyl-4-yl)methoxy]pyridine (A), as a foam; NMR (CDCl₃): 2.3(s,3H), 2.5(s,3H), 4.95(s,2H), 6.6(s,1H), 6.8-7.0(m,8H), 7.1(d,2H), 7.15-7.5(m,14H), 7.7(d,2H), 7.85-7.95(m,1H); ¹³C NMR (CDCl₃): 69.1 (benzylic CH₂).

EXAMPLES 56-58

Using an analogous procedure to that described in Example 1, but starting from an appropriate compound of formula III wherein L is triphenylmethyl, the following compounds of formula I were obtained in yields of 51-86%:

(Example 56): 2,6-Dimethyl-3-(4-methoxyphenyl)-4-[(2'-(1H-tetrazol-5-yl)biphenyl-4-yl)methoxy]pyridine hydrochloride, m.p. 131°-135° C.; NMR (d₆-DMSO): 2.2(s,3H), 2.45(s,3H), 3.8(s,3H), 5.1(s,2H), 6.9-7.1(m,5H), 7.15-7.25(m,4H), 7.5-7.7(m,4H); mass spectrum (−ve FAB, CH₃OH/m-nitrobenzyl alcohol): 462 (M−H)⁻; microanalysis, found: C,67.6; H,5.6; N,13.8%; C₂₈H₂₅N₅O₂ requires: C,67.3; H,5.2; N,14.0%.

(Example 57): 2,6-Dimethyl-3-(4-methylphenyl)-4-[(2'-(1H-tetrazol-5-yl)biphenyl-4-yl)methoxy]pyridine hydrochloride, m.p. 134°-137° C.; NMR (d₆-DMSO): 2.4(2 x s; 6H), 2.7(s,3H), 5.35(s,2H), 7.1(d,2H), 7.15-7.35(m,7H), 7.6-7.75(m,4H); mass spectrum (+ve FAB, CH₃OH/m-nitrobenzyl alcohol): 448 (M+H)⁺.

(Example 58): 2,6-Dimethyl-4-[(2'-(1H-tetrazol-5-yl)biphenyl-4-yl)methoxy]-3-(4-trifluoromethylphenyl)-pyridine, m.p. 172°-173° C.; NMR (d₆-DMSO): 2.2(s,3H), 2.45(s,3H), 5.15(s,2H), 7.0-7.1(m,3H), 7.2(d,2H), 7.5-7.7(m,6H), 7.8(d,2H); mass spectrum (+ve FAB, methanol/m-nitrobenzyl alcohol): 502 (M+H)⁺; microanalysis, found: C,65.8; H, 4.1; N,13.7%; C₂₈H₂₂F₃N₅O.0.5H₂O requires: C,65.8; H,4.5; N,13.9%.

The necessary starting materials of formula III used in Examples 56-58, corresponding to starting material A in Example 1, were obtained in yields of 67-80% using an analogous procedure to that described in Example 1 as follows:

(Example 56A): 2,6-Dimethyl-3-(4-methoxyphenyl)-4-[(2'-(2-triphenylmethyl-2H-tetrazol-5-yl)biphenyl-4-yl)methoxy]pyridine, as a foam; NMR (CDCl₃): 2.5(s,3H), 2.7(s,3H), 4.0(s,3H), 5.15(s,2H), 6.8(s,1H), 7.0-7.2(m,9H), 7.25(d,2H), 7.3-7.5(m,12H), 7.55-7.6(m,1H), 7.65-7.7(m,2H), 8.1-8.15(m,1H), (Example 57A): 2,6-Dimethyl-3-(4-methylphenyl)-4-[(2'-(2-triphenylmethyl-2H-tetrazol-5-yl)biphenyl-4-yl)methoxy]pyridine, as a foam; NMR (CDCl₃): 2.3(s,3H), 2.4(s,3H), 2.6(s,3H), 4.95(s,2H), 6.6(s,1H), 6.8-7.0(m,8H), 7.05(d,2H), 7.1-7.3(m,14H), 7.4-7.5(m,2H), 7.9-8.0(m,1H).

(Example 58A): 2,6-Dimethyl-3-(4-trifluoromethylphenyl)-4-[(2'-(2-triphenylmethyl-2H-tetrazol-5-yl)biphenyl-4-yl)methoxy]pyridine, as a foam; NMR (CDCl₃): 2.3(s,3H), 2.5(s,3H), 4.95(s,2H), 6.65(s,1H), 6.8-7.0(m,8H), 7.05(d,2H), 7.1-7.3(m,9H), 7.35-7.45(m,5H), 7.7(d,2H), 7.9-8.0(m,1H).

The necessary substituted phenylboronic acid starting materials used in Examples 56 and 58, corresponding to starting material C in Example 55, were obtained in yields of 50 to 72% using an analogous procedure to that described in Example 55, part (ii) as follows:

(Example 56C): (4-Methoxyphenyl)boronic acid, m.p. 177° C.; NMR (d₆-DMSO): 3.75(s,3H), 6.7(d,2H), 7.2s (d,2H).

(Example 58C): (4-Trifluoromethylphenyl)boronic acid, m.p. 242°-245° C.; NMR (d₆-DMSO): 5.4-5.6(br,2H), 7.6(d,2H), 8.0(d,2H).

The necessary starting materials used in Examples 56-58, corresponding to starting material D in Example 55, were obtained in yields of 40-84% using an analogous procedure to that described in Example 55, part (iii) as follows:

(Example 56D): 2,6-Dimethyl-3-(4-methoxyphenyl)-4-(phenylmethoxy)pyridine, as a waxy solid: NMR (CDCl₃): 2.3(s,3H), 2.5(s,3H), 3.85(s,3H), 5.1(s,2H), 6.5(s,1H), 6.95(d,2H), 7.1-7.4(m,7H).

(Example 57D): 2,6-Dimethyl-3-(4-methyphenyl)-4-(phenylmethoxy)pyridine, as an oil: NMR (CDCl₃): 2.3(s,3H), 2.4(s,3H), 2.55(s,3H), 5.1(s,2H), 6.5(s,1H), 7.1(d,2H), 7.2-7.4(m,7H).

(Example 58D): 2,6-Dimethyl-4-phenylmethoxy-3-(4-trifluoromethylphenyl)pyridine, as an oil; NMR (CDCl₃): 2.3(s,3H), 2.6(s,3H), 5.1(s,2H), 6.7(s,1H), 7.1-7.2(m,2H), 7.25-7.4(m,5H), 7.7(d,2H).

The necessary starting materials of formula IV used in Examples 56-58, corresponding to starting material E in Example 55, were obtained in yields of 65-97% using an analogous procedure to that described in Example 55, part (iv) as follows:

(Example 56E): 2,6-Dimethyl-3-(4-methoxyphenyl)-4(1H)-pyridone, as a non-crystalline solid, which was used without purification or characterisation.

(Example 57E): 2,6-Dimethyl-3-(4-methylphenyl)-4(1H)-pyridone, as a non-crystalline solid; NMR (d₆-DMSO): 2.0(s,3H), 2.2(s,3H), 2.3(s,3H), 5.9(5,1H), 7.0(d,2H), 7.35(d,2H), 11.0(br s, 1H).

(Example 58E): 2,6-Dimethyl-3-(4-trifluoromethylphenyl)-4(1H)-pyridone, as a non-crystalline solid; NMR (d$_6$-DMSO): 2.05(s,3H), 2.2(s,3H), 6.0(s,1H), 7.5(d,2H), 7.6(d,2H), 11.2(br s, 1H).

EXAMPLE 59

Using an analogous procedure to that described in Example 1, but starting from 2,6-dimethyl-3-(phenylmethyl)-4-[(2'-(2-triphenylmethyl-2H-tetrazol-5-yl)biphenyl-4-yl)methoxy]pyridine (A), there was obtained in 50% yield 2,6-dimethyl-3-(phenylmethyl)-4-[(2'-(1H-tetrazol-5-yl)biphenyl-4-yl)methoxy]pyridine hydrochloride, m.p. 211°–214° C. (decomposition); NMR (d$_6$-DMSO): 2.65(s,3H), 2.7(s,3H), 4.0(s,2H), 5.4(s,2H), 7.05–7.3(m,9H), 7.5–7.75(m,4H); mass spectrum (+ve FAB, DMSO/m-nitrobenzyl alcohol): 448 (M+H)$^+$; microanalysis, found: C,68.8; H,5.5; N,14.4%; C$_{28}$H$_{25}$N$_5$O.HCl.0.25H$_2$O requires: C,68.9; H,5.4; N,14.3%.

The starting material A was obtained as follows:

(i) A mixture of activated zinc (290 mg) and benzyl bromide (760 mg) in THF (15 ml) was stirred for 1 hour. 2,6-Dimethyl-3-iodo-4-(phenylmethoxy)pyridine (500 mg) was added followed by tetrakis(triphenylphosphine)palladium (50 mg). The mixture was heated under reflux for 2 hours and then volatile material was removed by evaporation. Ethylenediaminetetracetic acid (2 g) in water (20 ml) was added and the mixture was extracted with ethyl acetate (3×20 ml). The extracts were washed with saturated sodium carbonate solution (20 ml), water (20 ml), saturated sodium chloride solution (20 ml) and then dried (MgSO$_4$). The solvent was removed by evaporation and the residue was purified by flash chromatography, eluting with ethyl acetate/hexane (1:1 v/v), to give 2,6-dimethyl-3-phenylmethyl-4-(phenylmethoxy)pyridine (B) (197 mg), as an oil; NMR (CDCl$_3$): 2.5(2x s,6H), 4.05(s,2H), 5.1(s,2H), 6.6(s,1H), 7.05–7.4 (complex m,10H).

(ii) A solution of compound B (375 mg) in methanol (5 ml) was catalytically hydrogenated over 10% palladium on carbon. When uptake of hydrogen ceased, the catalyst was removed by filtration through diatomaceous earth. The filtrate was concentrated by evaporation and the residue was purified by flash chromatography, eluting with ethyl acetate/hexane (1:9 v/v), to give 2,6-dimethyl-3-phenylmethyl-4-(1H)-pyridone (C) (191 mg), m.p. 212°–215° C.; NMR (CDCl$_3$): 2.2(2x s,6H), 3.9(s,2H), 6.1(s,2H), 7.0–7.2(m,5H), 12.35(br s, 1H).

(iii) Using an analogous procedure to that described in Example 1, but starting from compound C, there was obtained in 97% yield 2,6-dimethyl-3-phenylmethyl-4-[(2-(2'-triphenylmethyl-2H-tetrazol-5-yl)biphenyl-4-yl)methoxy]pyridine, as a foam; NMR (CDCl$_3$): 2.5(s,6H), 4.05(s,2H), 5.0(s,2H), 6.6(s,1H), 6.85–7.55-(complex m,27H), 7.9–8.0(m,1H).

EXAMPLE 60

Using an analogous procedure to that described in Example 36, but starting from 2-ethyl-4-[(2-methoxy-2'-(2-tributylstannyl-2H-tetrazol-5-yl)biphenyl-4-yl)methoxy-5,6,7,8-tetrahydroquinoline [prepared as a solution in xylene using a similar procedure to that described in Example 36 but starting from 4-[(2'-cyano-2-methoxybiphenyl-4-yl)methoxy]-2-ethyl-5,6,7,8-tetrahydroquinoline (A)] there was obtained in 35% yield 2-ethyl-4-[(2-methoxy-2'-(1H-tetrazol-5-yl)biphenyl-4-yl)methoxy]-5,6,7,8-tetrahydroquinoline hydrochloride, m.p. 213°–214° C.; NMR (d$_6$-DMSO): 1.3(t,3H), 1.65–1.9(m,4H), 2.55–2.7(m,2H), 2.9–3.05(m,4H), 3.3(s,3H), 5.45(s,2H), 7.0(s,1H), 7.1(dd,1H), 7.25(d,1H), 7.45(d,2H), 7.5–7.75(m,3H); mass spectrum (+ve FAB, DMSO/m-nitrobenzyl alcohol): 442 (M+H)$^+$; microanalysis, found: C,62.8; H,6.0; N,14.2%; C$_{26}$H$_{27}$N$_5$O$_2$.HCL.H$_2$O requires: C,62.9; H,6.0; N,14.1%.

Compound A was obtained as follows:

(i) Using an analogous procedure to that described in Example 38, part (i), but starting from 2-methoxy-4-methylphenol, there was obtained in 91% yield (2-methoxy-4-methylphenyl)trifluoromethanesulphonate (B), as an oil; NMR (CDCl$_3$): 2.35(s,3H), 3.9(s,3H), 6.75(d,1H), 6.8(s,1H), 7.1(d,1H).

(ii) Using an analogous procedure to that described in Example 41, part (ii), but starting from compound B of part (i) of this example, there was obtained in 97% yield (2'methoxy-4'-methyl)biphenyl-2-carbonitrile (C), as an oil; NMR (CDCl$_3$): 2.35(s,3H), 3.9(s,3H), 6.7–7.8(complex m,7H).

(iii) Using an analogous procedure to that described in Example 35, part (ii), but starting from compound C, there was obtained in 53% yield (4'-bromomethyl-2'-methoxy)biphenyl-2-carbonitrile (D), as an oil; NMR (CDCl$_3$): 3.65(s,3H), 4.5(s,2H), 7.0–7.8(complex m,7H).

(iv) Using an analogous procedure to that described in Example 1, but starting from compound D and 2-ethyl-5,6,7,8-tetrahydro-4(1H)-quinolone, there was obtained in 60% yield 4-[(2'-cyano-2-methoxybiphenyl-4-yl)methoxy]-2-ethyl-5,6,7,8-tetrahydroquinoline (A), as an oil; NMR (CDCl$_3$): 1.3(t,3H), 1.75–1.95(m,4H), 2.65–2.85(m,4H), 2.9(br t,2H), 3.85(s,3H), 5.15(s,2H), 6.6(s,1H), 7.1(d,2H), 7.3(d,1H), 7.45(d,2H), 7.65(d,1H), 7.75(dd,1H).

EXAMPLE 61

Using an analogous procedure to that described in Example 36, but starting from 4-[(2-acetyl-2'-(2-tributylstannyl-2H-tetrazol-5-yl)biphenyl-4-yl)methoxy]-2-ethyl-5,6,7,8-tetrahydroquinoline [prepared as a solution in xylene using a similar procedure to that described in Example 36 but starting from 4-[(2-acetyl-2'-cyanobiphenyl-4-yl)methoxy]-2-ethyl-5,6,7,8-tetrahydroquinoline (A)], there was obtained in 30% yield 4-[(2-acetyl-2'-(1H-tetrazol-5-yl)biphenyl-4-yl)methoxy]-2-ethyl-5,6,7,8-tetrahydroquinoline hydrochloride, m.p. 158°–161° C.; NMR (d$_6$-DMSO at 120° C.): 1.3(t,3H), 1.75–1.9(m,4H), 2.1(s,3H), 2.65–2.75(m,2H), 2.9–3.1(m,4H), 5.55(s,2H), 7.2–7.9 (complex m,8H); mass spectrum (+ve FAB, DMSOm-nitrobenzyl alcohol): 454 (M+H)$^+$; microanalysis, found: C,63.6; H,6.1; N,13.8%; C$_{27}$H$_{27}$N$_5$O$_2$.HCl.H$_2$O requires: C,63.8; H,5.9; N,13.8%.

Compound A was obtained as follows:

(i) Using an analogous procedure to that described in Example 60, part (i), but starting from 2-acetyl-4-methylphenol, there was obtained in 88% yield (2-acetyl-4-methylphenyl)trifluoromethanesulphonate (B), as an oil; NMR (CDCl$_3$): 2.4(s,3H), 2.6(s,3H), 7.2(d,1H), 7.35(dd,1H), 7.6(d,1H).

(ii) Using an analogous procedure to that described in Example 60, part (ii), but starting from compound B of part (i) of this example, there was obtained in 51% yield (2'-acetyl-4'-methyl)biphenyl-2-carbonitrile (C), as a non-crystalline solid; NMR (CDCl$_3$): 2.4(s,3H), 2.5(s,3H), 7.2(d,1H), 7.3–7.5(m,3H), 7.55–7.75(m,3H).

(iii) Using an analogous procedure to that described in Example 60, part (iii), but starting from compound C of part (ii) of this example, there was obtained in 80% yield (2'-acetyl-4'-bromomethyl)biphenyl-2-carbonitrile (D), as an oil; NMR (CDCl$_3$): 2.45(s,3H), 4.55(s,2H), 6.7–8.0(m,2H).

(iv) Using an analogous procedure to that described in Example 60, part (iv), but starting from compound D of part (iii) of this example, there was obtained in 30% yield 4-[(2-acetyl-2'-cyanobiphenyl-4-yl)methoxy]-2-ethyl-5,6,7,8-tetrahydroquinoline (A), as an oil; NMR (CDCl$_3$): 1.3(t,3H), 1.7–1.95(m,4H), 2.4(s,3H), 2.65–2.8(m,2H), 2.75(q,2H), 2.85–2.95(m,2H), 5.2(s,2H), 6.6(s,1H), 7.35–7.55(m,3H), 7.6–7.8(m,3H), 7.85(d,1H).

EXAMPLE 62

Hydrogen chloride was bubbled for 15 minutes through a solution of 2-ethyl-5,6,7,8-tetrahydro-4-[(2'-(2-tributylstannyl-2H-tetrazol-5-yl)biphenyl-4-yl)methoxy]quinoline in xylene [prepared by refluxing a mixture of 4-[(2'-cyanobiphenyl-4-yl)methoxy]-2-ethyl-5,6,7,8-tetrahydroquinoline (A) (1.1 g) and tributyl tin azide (3.0 g) in xylene (3 ml) for 60 hours under an atmosphere of argon]. Volatile material was then removed by evaporation and the residue was recrystallised from methanol/ethyl acetate to give 2-ethyl-5,6,7,8-tetrahydro-4-[(2'-(1H-tetrazol-5-yl)biphenyl-4-yl)methoxy]quinoline hydrochloride (0.77 g), as an off-white solid; NMR and thin layer chromatography (carried out on Merck Art 5715 Kieselgel 60 F$_{254}$ using methanol/ethyl acetate (1:4 v/v) as eluant) were identical to those obtained with the product of Example 5.

The starting material A was obtained using procedure A or B as follows:

PROCEDURE A (i) 2M Sodium carbonate solution (200 ml) was added to a stirred mixture of 4-methylphenylboronic acid (30 g), 2-bromobenzonitrile (36.4 g), palladium (II) chloride (0.4 g), methanol (200 ml) and toluene (200 ml) at 5° C. The temperature rose to approximately 20° C. and a solid precipitated. The reaction mixture was then heated at reflux for 2 hours. The reaction mixture was allowed to cool and water (100 ml) was added, followed by diatomaceous earth (5 g). The mixture was stirred for 15 minutes, then filtered through diatomaceous earth. The organic phase of the filtrate was separated and washed with 2M sodium carbonate solution and then water. The organic phase was then filtered and the filtrate evaporated. The resultant solid was recrystallised from petroleum ether (b.p. 110°–120° C.) to give 4'-methylbiphenyl-2-carbonitrile (33 g) which was used without further purification.

(ii) A mixture of 4'-methylbiphenyl-2-carbonitrile (3.86 g), N-bromosuccinimide (3.92 g) and azo(-bisisobutyronitrile) (0.15 g) in chlorobenzene (75 ml) were heated at 70° C. for 3 hours. Further N-bromosuccinimide (0.3 ) and azo(bisisobutyronitrile) (0.05 g) were added and the mixture was heated for another 15 minutes. Heating was stopped and the mixture stirred for 16 hours at ambient temperature. Water (50 ml) was added and the mixture stirred for 30 minutes and filtered. The organic phase was separated, washed with water (50 ml) and dried (MgSO$_4$). The solvent was removed by evaporation and the resultant solid recrystallised from cyclohexane to give 4'-bromomethylbiphenyl-2-carbonitrile (3.9 g) (A) as a solid; NMR (CDCl$_3$): 4.55(s,2H), 7.4–7.85(m, 8H).

(iii) Sodium hydride (0.25 g of a 60% suspension in mineral oil) was added to a solution of 2-ethyl-5,6,7,8-tetrahydro-4(1H)-quinolone (0.9 g) and 4'-bromomethylbiphenyl-2-carbonitrile (1.5 g) in DMF (15 ml). The solution was stirred under an atmosphere of argon for 18 hours. Water (200 ml) was added and the resulting precipitate collected by filtration and recrystallised from ethyl acetate/hexane to give 2-ethyl-5,6,7,8-tetrahydro-4-[(2'-cyanobiphenyl-4-yl)methoxy]quinoline (A) (1.44 g) as a white solid m.p. 147°–148° C.; NMR (CDCl$_3$): 1.29(t,3H), 1.7–1.95(m,4H), 5.17(s,2H), 6.57(s,1H), 7.4–7.7 (complex m,7H), 7.78(d,1H); mass spectrum (+ve CI) 369 (M+H)$^+$.

PROCEDURE B

Tetrakis(triphenylphosphine)palladium (40 mg) was added to a suspension of 4-[(2-ethyl-5,6,7,8-tetrahydroquinolin-4-yl)oxymethyl]phenylboronic acid (obtained as described in Example 36, part (i)) (200 mg) and 2-bromobenzonitrile (106 mg) in toluene (2 ml) ethanol (0.5 ml) and 2M aqueous sodium carbonate (0.58 ml). The mixture was degassed and placed under an atmosphere of argon, then heated under reflux for 12 hours. The resulting solution was cooled to ambient temperature, and dichloromethane (30 ml) and water (10 ml) were added. The organic layer was separated, dried (MgSO$_4$) and the solvent removed by evaporation. The residue was purified by flash chromatography, eluting with ethyl acetate/hexane (3:1 v/v), and the product triturated with ether/hexane to give 2-ethyl-5,6,7,8-tetrahydro-4-[(2'-cyanobiphenyl-4-yl)methoxy]quinoline (A) (106 mg); NMR and m.p. similar to that obtained for the product of procedure A.

EXAMPLE 63

Sodium hydride (50% dispersion in mineral oil; 0.091 g) was washed with hexane, dried with a stream of nitrogen and covered with N-methylpyrrolidone (NMP) (5 ml). The mixture was cooled to below 10° C. and propanethiol (0.145 g; 1.9 mmol) was added slowly with stirring. After 15 minutes, a solution of 2-ethyl-4-[(2'-(1-(4-nitrophenyl)-1H-tetrazol-5-yl)biphenyl-4-yl)methoxy-5,6,7,8-tetrahydroquinoline (A) (0.5 g) in NMP (10 ml) was added slowly maintaining the temperature of the reaction mixture below 10° C. The mixture was then stirred for 2 hours. Concentrated hydrochloric acid was added until the reaction mixture was pH 2. Water (25 ml) was then added and the suspended white solid collected by filtration. The crude product was recrystallised from ethanol to give 2-ethyl-5,6,7,8-tetrahydro-4-[(2'-(1H-tetrazol-5-yl)-biphenyl-4-yl)methoxy]quinoline hydrochloride as a solid, in 54% yield; m.p. 235°–237° C.; NMR and tlc similar to those obtained for the products of Examples 5 and 62.

[Note: The reaction was also carried out using sodium methoxide (2 equivalents) or sodium ethoxide (2 equivalents) in NMP at ambient temperature, in place of sodium hydride and propanethiol, and the product was isolated in 80–90% yield having similar m.p. and NMR to that above.]

The starting material A was obtained as follows:

(i) Thionyl chloride (120.5 g) was added to a stirred mixture of 2-bromobenzoic acid (194 g) in toluene (500 ml) and N,N-dimethylformamide (DMF) (5 ml) and the mixture heated at 80° C. for 4 hours. The solution was cooled to 20° C. and added slowly to a solution of 4-nitroaniline (133.1 g) in toluene (500 ml) and NMP (120 ml), maintaining the temperature of the reaction mixture between 20°–25° C. The reaction mixture was then stirred for 24 hours when a solid precipitated. Water (360 ml) was added with rigorous stirring and the suspended solid collected by filtration, and washed successively with water, toluene and acetonitrile to give 2-bromo-N-(4-nitrophenyl)benzamide (B) as a solid, in 87% yield; m.p. 200°–202° C.; (NMR (d$_6$-DMSO): 7.4–7.8(m,7H), 8.0(d,2H), 8.3(d,2H), 11.5(brs, 1H); which was used without further purification.

(ii) Triethylamine (1.04 g; 10.38 mmol) was added to a mixture of amide B (3 g) in acetonitrile (12 ml) and DMF (0.189 g) and the mixture was stirred for 90 minutes. Thionyl chloride (1.44 g) was then added slowly keeping the reaction temperature below 25° C. The mixture was stirred for 5 hours at ambient temperature and then cooled to 10° C. Triethylamine (2.83 g) was then added, followed by sodium azide (1.33 g) and tetrabutylammonium bromide (0.42 g). The mixture was stirred for 2 hours at 10° C. and then allowed to warm to ambient temperature and stirred for 24 hours. The mixture was poured into excess water and the precipitated solid collected by filtration. The solid was purified by trituration with a hot mixture of ethyl acetate (26 ml) and triethylamine (0.1 ml) to give 5-(2-bromophenyl-1-(4-nitrophenyl-1H-tetrazole (C) (2.36 g; 73% yield) as an off-white solid, m.p. 169°–170°; NMR (d$_6$-acetone; 270 MHz): 7.61–7.86(m,6H), 8.41(d,2H); microanalysis, found: C,44.8; H,2.1; N,20.0; Br,23.6%; $C_{13}H_8BrN_5O_2$ requires: C,45.1; H,2.3; N,20.2; Br,23.1%.

(iii) Using an analogous procedure to that described in Procedure B of Example 62, but using compound C (202 mg) in place of 2-bromobenzonitrile and proportionate quantities of the other necessary reagents, there was obtained after flash chromatography eluting with ethyl acetate/hexane (3:1 v/v) and trituration with ether/hexane, 2-ethyl-4-[(2'-(1-(4'-nitrophenyl)-1H-tetrazol-5-yl)biphenyl-4-yl)methoxy]-5,6,7,8-tetrahydroquinoline (A) (134 mg) as an off white solid, m.p. 208°–210° C.; NMR (CDCl$_3$): 1.31(t,3H), 1.8–2.0(m,4H), 2.70(m,2H), 2.78(q,2H), 2.92(m,2H), 5.03(s,2H), 6.54(s,1H), 6.59(d,2H), 7.67(m,2H), 7.85–7.95(m,3H); mass spectrum (+ve FAB DMSO, CH$_3$OH, NBA) 533 (M+H)$^+$; microanalysis, found: C,69.5; H,5.4; N,15.5; $C_{31}H_{28}N_6O_3$ requires: C,69.9; H,5.3; N,15.8%.

Alternatively step (iii) of Procedure B can be replaced by the following procedure:

(a) A mixture of 4-methylphenyl boronic acid (9.7 g) sodium carbonate (16.7 g), water (100 ml), methanol (50 ml) and toluene (50 ml) was heated to 60° C. to give a clear solution. Compound C (20.0 g) was then added, followed by tetrakis(triphenylphosphine)palladium (0.3 g) and the mixture was heated at reflux for 3 hours. Toluene (30 ml) was added and the warm mixture was filtered through diatomaceous earth. The organic phase was separated and the aqueous phase extracted with toluene (40 ml). The combined organic phases were evaporated to give a solid which was recrystallised from toluene/petroleum ether (100°–120° C.) (1:1 v/v) to give 5-(4'-methylbiphenyl-2-yl)-1-(4-nitrophenyl)-1H-tetrazole (D) (18.7 g; 90% yield), m.p. 164°–166° C; NMR (CDCl$_3$): 2.3(3H,s), 6.45(2H,d), 6.85(4H,m,), 7.38(1H,d), 7.65(2H,m), 7.85(1H,d), 8.0(2H,d).

(b) A mixture of compound D (8.0 g; 21 mmol), N-bromosuccinimide (4.53 g) and azo(bisisobutyronitrile) (73 mg) in methyl chloroform (50 ml) was heated at reflux for 4 hours. The mixture was cooled to ambient temperature, washed with water (3×50 ml), and the suspended solid collected by filtration to give 5-(4'-bromethybiphenyl-2-yl)-1-(4-nitrophenyl)-1H-tetrazol (E) (7.3 g), m.p. 192°–195° C.; NMR (CDCl$_3$): 4.4(2H,s), 6.52(2H,d), 6.85(2H,d), 7.07(2H,d), 7.4(1H,d), 7.7(2H,m), 7.9(1H,d).

(c) A mixture of 2-ethyl-5,6,7,8-tetrahydro-4(1H)-quinolone (1.95 g), and potassium carbonate (2.28 g) in NMP (75 ml) was heated at 60° C. for 20 minutes with stirring. Compound E (5.2 g) was added and the reaction mixture was heated at 80° C. for 90 minutes. The mixture was allowed to cool to ambient temperature and water (150 ml) was added. The resultant precipitate was collected by filtration, dried at 60° C., then recrystallised from toluene to give 2-ethyl-4-[(2'-(1-(4-nitrophenyl)-1H-tetrazol-5-yl)biphenyl-4-yl)methoxy]-5,6,7,8-tetrahydroquinoline, as a solid in 60% yield; m.p. 205°–207° C.; NMR (CDCl3):1.30(3H,t), 1.90(4H,m), 2.60–3.00(6H,m), 5.04(2H,m), 6.52(2H,d), 6.60(1H,s), 6.80(2H,d), 7.11(2H,d), 7.40(1H,d), 7.67(2H,d), 7.92(3H,m).

EXAMPLE 64

(Note: all parts by weight)

The compounds of the invention, for example the compounds of formula I described in Examples 2, 5, 6, 9, 10, 11, 12, 13, 14 and 41 and the non-toxic salts thereof, may be administered for therapeutic or prophylactic use to warm-blooded animals such as man in the form of conventional pharmaceutical compositions, typical examples of which include the following:

| | |
|---|---|
| a) Capsule (for oral administration) | |
| Active ingredient * | 20 |
| Lactose powder | 578.5 |
| Magnesium stearate | 1.5 |
| b) Tablet (for oral administration) | |
| Active ingredient * | 50 |
| Microcrystalline cellulose | 400 |
| Starch (pregelatinised) | 47.5 |
| Magnesium stearate | 2.5 |
| c) Injectable Solution (for intravenous administration) | |
| Active ingredient * | 0.05–1.0 |
| Propylene glycol | 5.0 |
| Polyethylene glycol (300) | 3.0–5.0 |
| Purified water | to 100% |
| d) Injectable Suspension (for intramuscular administration) | |
| Active ingredient * | 0.05–1.0 |
| Methylcellulose | 0.5 |
| Tween 80 | 0.05 |
| Benzyl alcohol | 0.9 |
| Benzalkonium chloride | 0.1 |
| Purified water | to 100% |

Note:
the active ingredient * may typically be an Example described hereinbefore and will conveniently be present as a pharmaceutically acceptable acid-addition salt, such as the hydrochloride salt. Tablets and capsules formulations may be coated in conventional manner in order to modify or sustain dissolution of the active ingredient. Thus, for example, they may be coated with a conventional enterically digestible coating.

Chemical Formulae
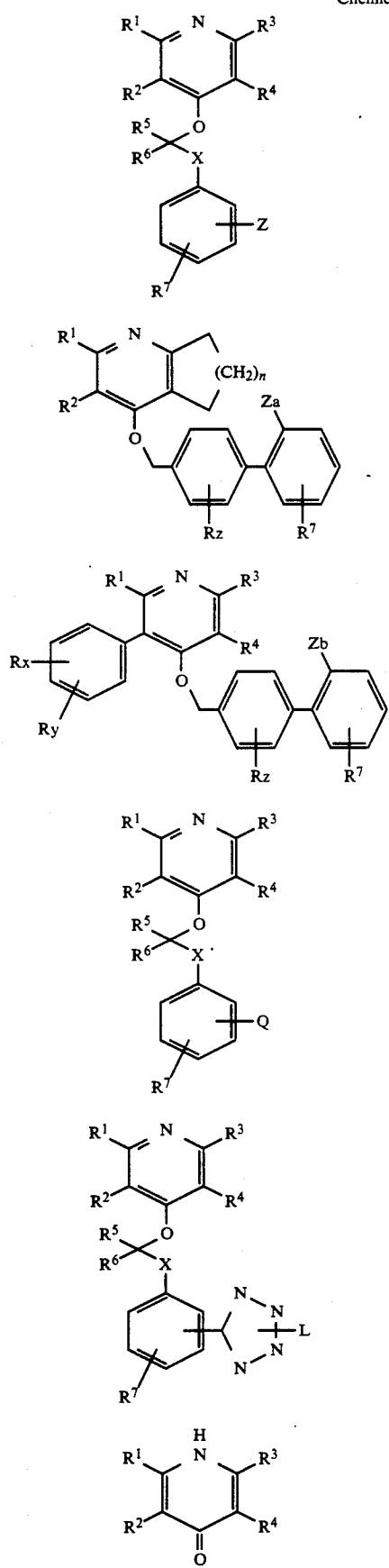
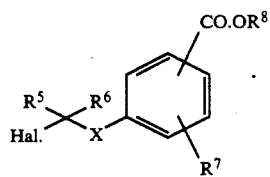
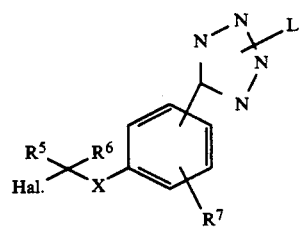
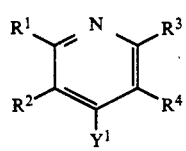
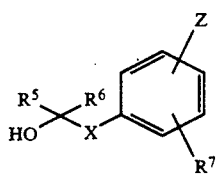
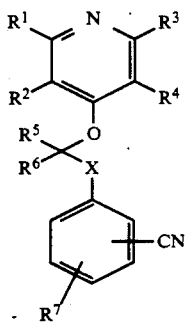
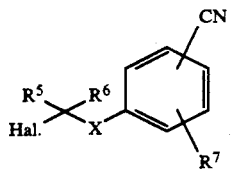
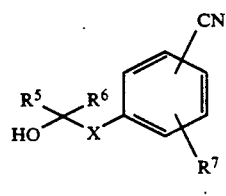

-continued
Chemical Formulae XII
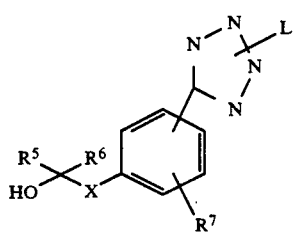
Scheme 2
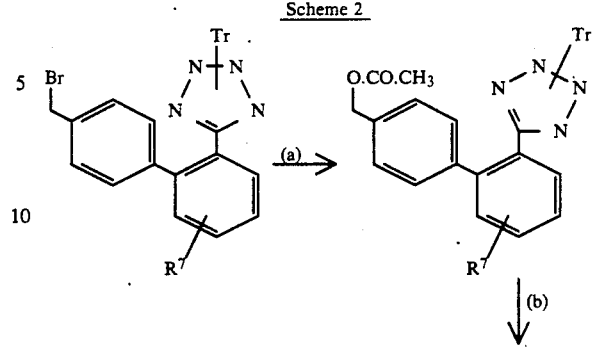
Scheme 1
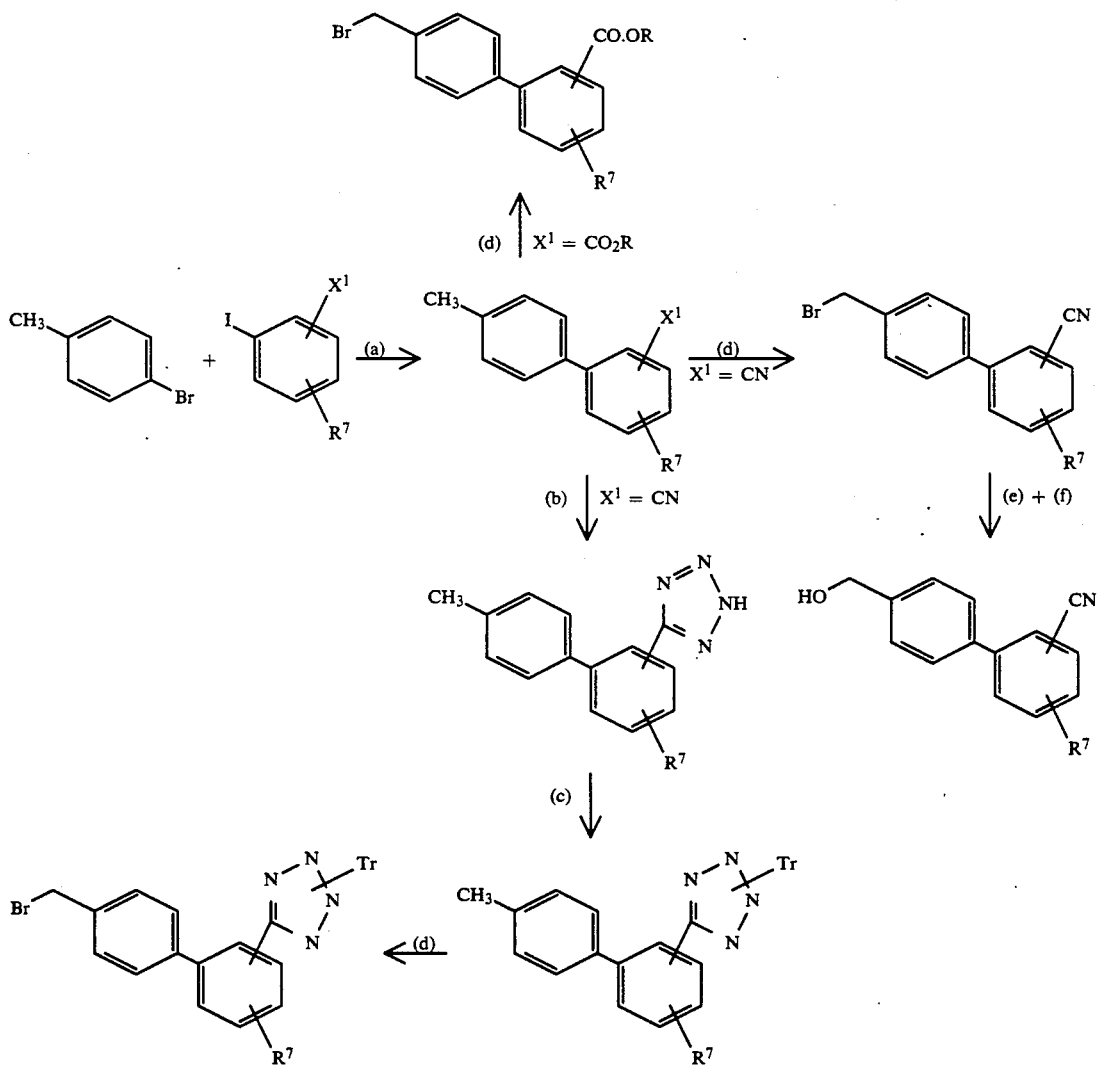
Note: R = lower alkyl, benzyl, phenyl; Tr = triphenylmethyl (trityl)
Reagents:
a) BuLi/THF; ZnCl$_2$/Et$_2$O; Pd(Ph$_3$P)$_4$
b) Bu$_3$Sn.N$_3$/toluene; HCl/toluene
c) Tr.Cl/Et$_3$N/CH$_2$Cl$_2$
d) N-bromosuccinimide/azoisobutyronitrile/CCl$_4$
e) Potassium acetate, hexaoxacyclooctadecane, DME, reflux
f) Lithium borohydride, THF, 0–25° C.

-continued
Scheme 2
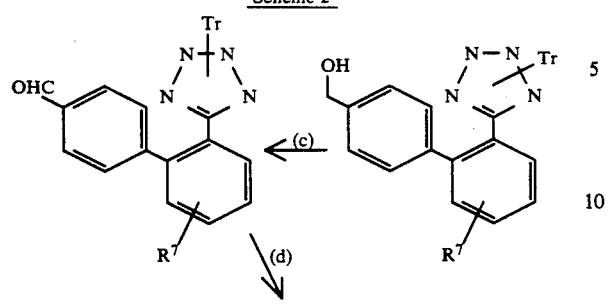
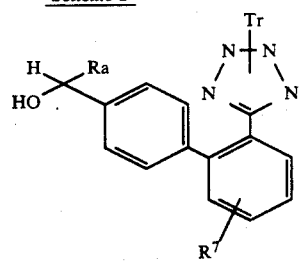
Note: Tr = triphenylmethyl (trityl); Ra = (1-4C)alkyl
Reagents:
(a) Potassium acetate, hexaoxacyclooctadecane, DME, reflux
(b) Lithium borohydride, THF, 0-25° C.
(c) Pyridine-SO₃ complex, Et₃N, DMSO, ambient temperature
(d) Ra.M, Et₂O/THF, −50° C. to ambient temperature
Scheme 3
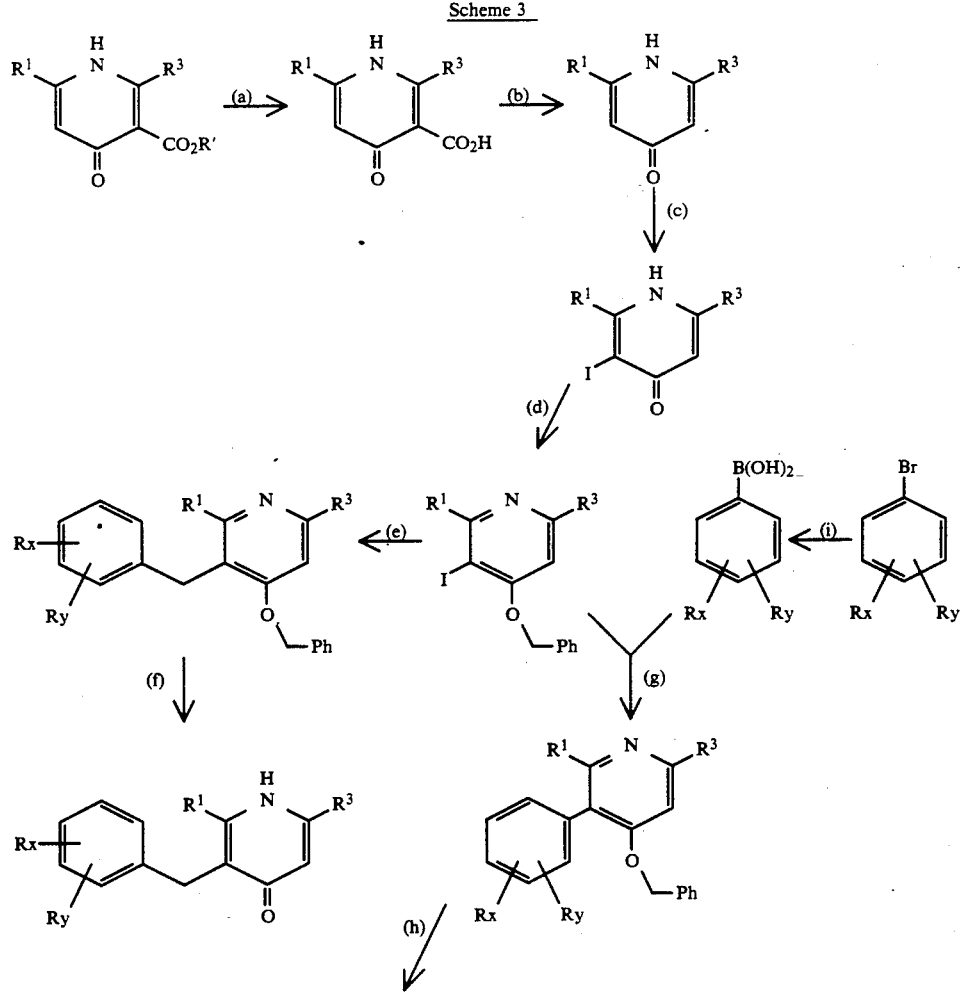

Scheme 3

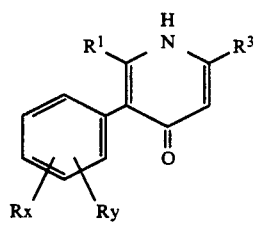

Note: $R^1 = R^3 =$ methyl or ethyl; Rx and Ry are optional substituents; Ph = phenyl; R' = lower alkyl Reagents:
a) NaOH, methanol, water, reflux
b) Sublimation at 250° C.
c) Iodine, NaOH, water
d) $C_6H_5CH_2Cl$, NaH, DMF, 50° C.
e) Product from (d) added to (Rx)(Ry)PhCH₂ZnBr in THF (from activated zinc, (Rx)(Ry)PhCH₂Br in THF), then $(Ph_3P)_4Pd$
f) hydrogenation over palladium on carbon, methanol
g) $(Ph_3P)_4Pd$, methanol, aq. NaHCO₃, toluene, reflux
h) ammonium formate, 10% palladium on carbon, methanol
i) tert-ButylLi/pentane; trimethyl borate/THF/−78° C.; aq. HCl

Scheme 4

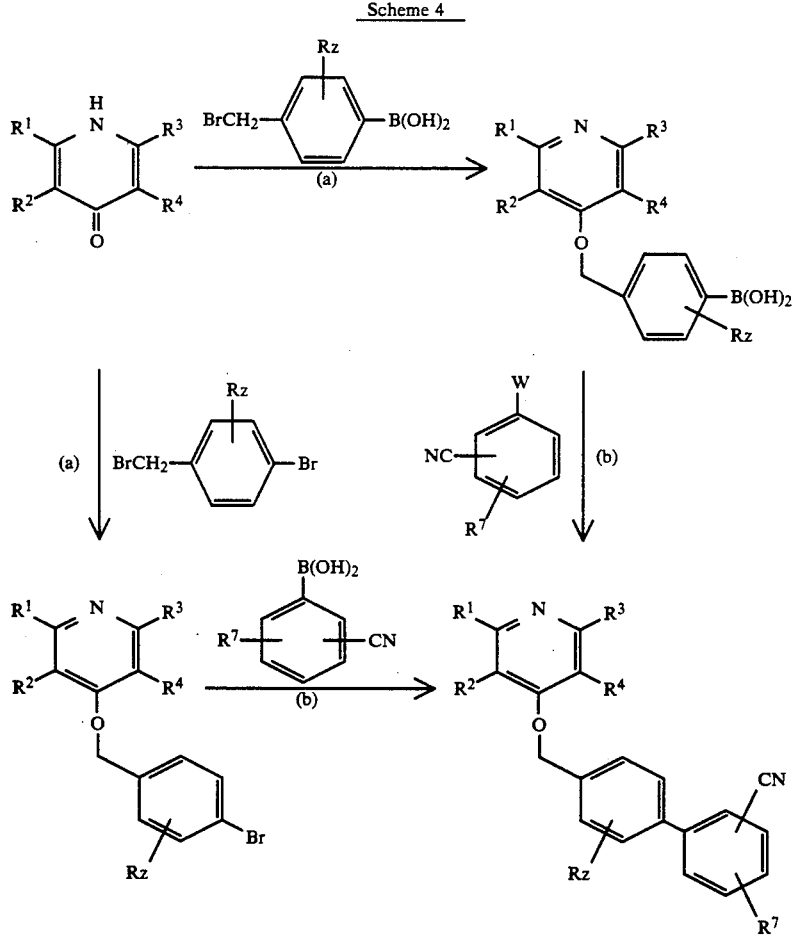

Note: W = Br or CF₃SO₂O—; Rz is an optional substituent

Reagents:
a) NaH, DMF, ambient temperature
b) $(Ph_3P)_4Pd$, toluene, ethanol, Na₂CO₃ or Et₃N, 90–120° C.

Scheme 5

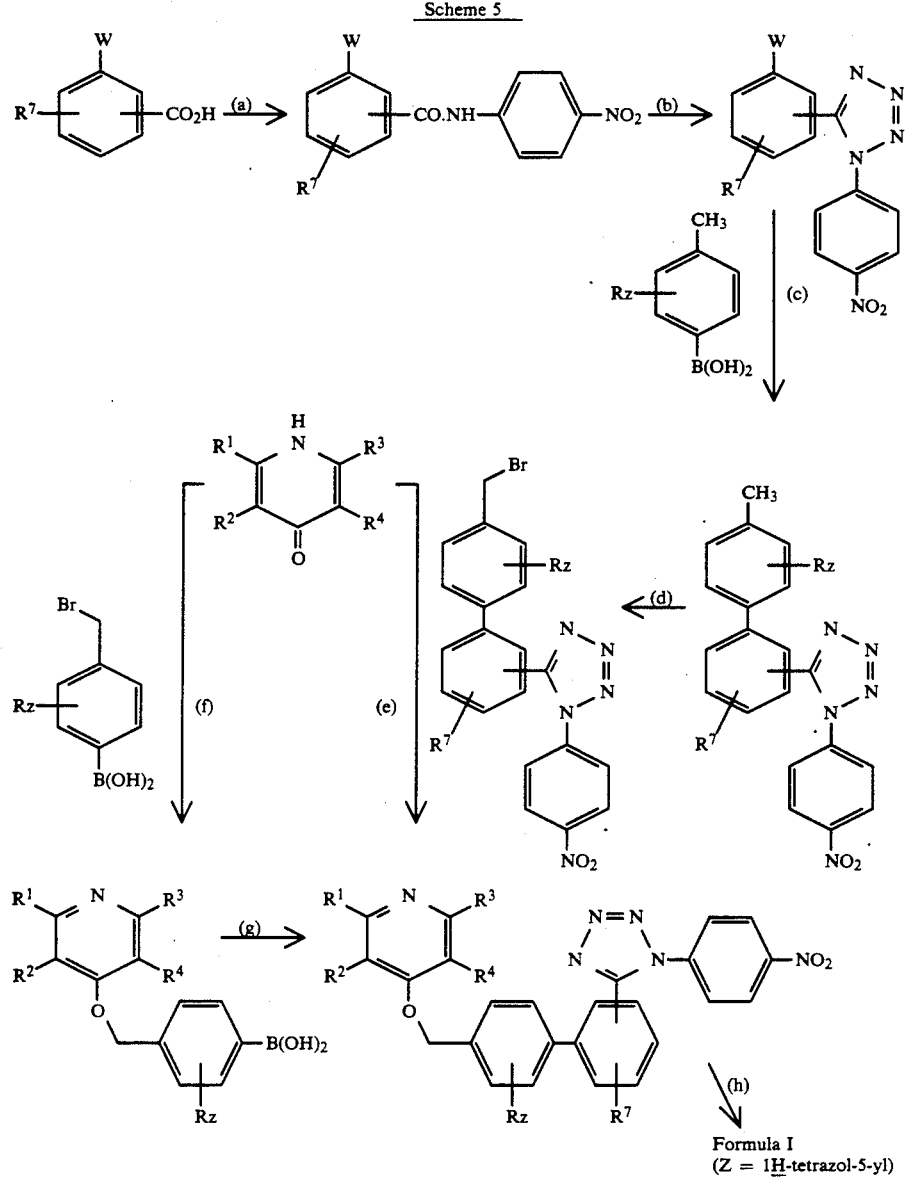

Note: W = Br or CF$_3$SO$_2$O; Rz is an optional substituent

Reagents:

(a) SOCl$_2$, DMF, toluene, 80° C.; then add to p-nitroaniline, toluene, NMP, ambient temperature (b) (i) Et$_3$N, CH$_3$CN, DMF; (ii) SOCl$_2$, 10° C.; and (iii) Et$_3$N, NaN$_3$, tetrabutylammonium bromide, 10° C. to ambient (c) add product of (b) and (Ph$_3$P)$_4$Pd to pre-formed mixture of the boronic acid, Na$_2$CO$_3$, H$_2$O, MeOH or EtOH, toluene, 60° C.; then reflux (d) NBS, azo(bisisobutyronitrile), CH$_3$CCl$_3$ (e) potassium carbonate, NMP, heat (f) NaH, DMF (g) analogous to (c)

(h) base (e.g. PrSNa, MeONa, EtONa), NMP, 10° C. to ambient

What we claim is:
1. A pyridine derivative of the formula I

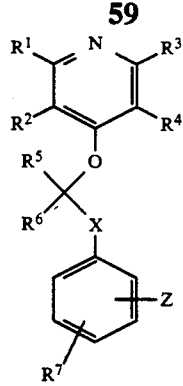

wherein $R^1$ is hydrogen, (1–8C)alkyl, (3–8C)cycloalkyl, phenyl or substituted (1–4C)alkyl, the latter containing one or more fluoro substituents or bearing a (3–8C)cycloalkyl, (1–4C)alkoxy or phenyl substituent; $R^2$ is hydrogen, (1–8C)alkyl, (3–8C)cycloalkyl, (3–8C)cycloalkyl-(1–4C)alkyl, carboxy, (1–4C)alkoxycarbonyl, (3–6C)alkenyloxycarbonyl, cyano, nitro, phenyl or phenyl(1–4C)alkyl; $R^3$ is selected from halogeno, (1–4C)alkoxy, amino, alkylamino and dialkylamino of up to 6 carbon atoms, and any of the values defined for $R^1$; $R^4$ is selected from hydrogen, (1–4C)alkyl optionally bearing an amino, (1–4C)alkanoylamino, phenylcarbonylamino, hydroxy or (1–4C)alkoxy substituent, carboxy, (1–4C)alkoxycarbonyl, (3–6)alkenyloxycarbonyl, cyano, nitro, carbamoyl, (1–4C)alkanoyl, N-alkylcarbamoyl and di-(N-alkyl)carbamoyl of up to 7 carbon atoms, halogeno, amino, alkylamino and dialkylamino of up to 6 carbon atoms, 3-(1–4C)alkylureido and (1–4C)alkanoylamino; or $R^4$ is a group of the formula -$A^1.A^2.B$ wherein $A^1$ is carbonyloxy, $A^2$ is (1–6C)alkylene and B is selected from hydroxy, (1–4C)alkoxy, phenyloxy, phenyl(1–4C)alkoxy, pyridyl(1–4C)alkoxy, 4-morpholino(1–4C)alkoxy, phenylamino, amino alkylamino and dialkylamino of up to 6 carbon atoms, (1–4C)alkanoylamino, (1–4C)alkylsulphonylamino, phenylsulphonylamino, sulphamoylamino (—NH.SO$_2$.NH$_2$), carboxamidomethylamino (—NH.CH$_2$.CO.NH$_2$), (1–4C)alkanoyloxy, phenylcarbonyloxy, aminocarbonyloxy (—O.CO.NH$_2$), (1–4C)alkylaminocarbonyloxy, carboxy, (1–4C)alkoxycarbonyl, carbamoyl, N-alkylcarbamoyl and di-(N-alkyl)carbamoyl of up to 7 carbon atoms, (1–4C)alkanoyl, 4-morpholino, 1-imidazolyl and succinimido group; or B is a group of the formula -$A^3.B^1$ wherein $A^3$ is oxy, oxycarbonyl or imino and $B^1$ is a 5 or 6-membered saturated or unsaturated heterocyclic ring containing 1 or 2 nitrogen atoms and linked to $A^3$ by a ring carbon atom; or $A^3$ is oxycarbonyl and $B^1$ is a 4-morpholino group or a 5 or 6-membered saturated heterocylic ring containing 1 or 2 nitrogen atoms, optionally bearing a (1–4C)alkyl group and linked to $A^3$ by a ring nitrogen atom; and wherein in $B^1$ the remainder of the ring atoms are carbon; $R^5$ is hydrogen; $R^6$ is hydrogen or (1–4C)alkyl; $R^7$ is selected from hydrogen, (1–4C)alkyl, (1–4C)alkoxy, halogeno, trifluoromethyl, cyano and nitro; X is phenylene optionally bearing a substituent selected from (1–4C)alkyl, (1–4C)alkoxy, halogeno, (1–4C)alkanoyl, trifluoromethyl, cyano and nitro; Z is 1H-tetrazol-5-yl, —CO.NH.(1H-tetrazol-5-yl) or a group of the formula —CO.OR$^8$ or —CO.NH.SO$_2$.R$^9$ in which $R^8$ is hydrogen or a non-toxic, biodegradable residue of a physiologically acceptable alcohol or phenol, and $R^9$ is (1–6C)alkyl, (3–8C)cycloalkyl or phenyl; and wherein any of said phenyl moieties may be unsubstituted or bear one or two substituents independently selected from (1–4C)alkyl, (1–4C)alkoxy, halogeno, cyano and trifluoromethyl; or an N-oxide thereof; or a non-toxic salt thereof.

2. A compound as claimed in claim 1 wherein $R^1$ is hydrogen, methyl, ethyl, propyl, isopropyl, butyl, isobutyl, sec-butyl, pentyl, hexyl, cyclopropyl, cyclopentyl, cyclohexyl, phenyl, fluoromethyl, trifluoromethyl, 2,2,2-trifluoroethyl, pentafluoroethyl, cyclopropylmethyl, cyclopentylmethyl, cyclohexylmethyl, 2-methoxyethyl, 2-ethoxyethyl, benzyl, 1-phenylethyl or 2-phenylethyl; $R^2$ is hydrogen, methyl, ethyl, propyl, isopropyl, butyl, isobutyl, sec-butyl, pentyl, hexyl, cyclopropyl, cyclopentyl, cyclohexyl, cyclopropylmethyl, cyclopentylmethyl, cyclohexylmethyl, carboxy, methoxycarbonyl, ethoxycarbonyl, propoxycarbonyl, allyloxycarbonyl, 2-methyl-2-propenyloxycarbonyl, 3-methyl-3-butenyloxycarbonyl, cyano, nitro, phenyl, benzyl, 1-phenylethyl or 2-phenylethyl; $R^3$ is selected from hydrogen, methyl, ethyl, propyl, isopropyl, butyl, isobutyl, sec-butyl, pentyl, hexyl, cyclopropyl, cyclopentyl, cyclohexyl, phenyl, fluoromethyl, trifluoromethyl, 2,2,2-trifluoroethyl, pentafluoroethyl, cyclopropylmethyl, cyclopentylmethyl, cyclohexylmethyl, 2-methoxyethyl, 2-ethoxyethyl, benzyl, 1-phenylethyl, 2-phenylethyl, fluoro, chloro, bromo, iodo, methoxy, ethoxy, amino, methylamino, ethylamino, butylamino, dimethylamino, diethylamino and dipropylamino; $R^4$ is selected from hydrogen, methyl, ethyl, aminomethyl, 2-aminoethyl, acetylaminomethyl, acetylaminoethyl, propionylaminomethyl, propionylaminoethyl, phenylcarbonylaminomethyl, phenylcarbonylaminoethyl, hydroxymethyl, 1-hydroxyethyl, 2-hydroxyethyl, methoxymethyl, 2-methoxyethyl, 2-ethoxyethyl, carboxy, methoxycarbonyl, ethoxycarbonyl, propoxycarbonyl, allyloxycarbonyl, 2-methyl-2-propenyloxycarbonyl, 3-methyl-3-butenyloxycarbonyl, cyano, nitro, carbamoyl, formyl, acetyl, butyryl, N-methylcarbamoyl, N-ethylcarbamoyl, N,N-dimethylcarbamoyl, N,N-diethylcarbamoyl, fluoro, chloro, bromo, iodo, amino, methylamino, ethylamino, butylamino, dimethylamino, diethylamino, dipropylamino, 3-methylureido, 3-ethylureido, 3-propylureido, formamido, acetamido and propanamido; or $R^4$ is a group of the formula -$A^1.A^2.B$ wherein $A^1$ is carbonyloxy, $A^2$ is methylene, ethylene, trimethylene or tetramethylene, in any of which one methylene may bear 1 or 2 methyl substituents, and B is selected from hydroxy, methoxy, ethoxy, isopropoxy, phenyloxy, benzyloxy, phenethyloxy, 2-pyridylmethoxy, 3-pyridylmethoxy, 4-pyridylmethoxy, 3-pyridylethoxy, 4-morpholinomethoxy, 4-morpholinoethoxy, phenylamino, amino, methylamino, ethylamino, butylamino, dimethylamino, diethylamino, dipropylamino, formamido, acetamido, propionylamino, methylsulphonylamino, ethylsulphonylamino, phenylsulphonylamino, sulphamoylamino, carboxamidomethylamino, acetyloxy, propionyloxy, phenylcarbonyloxy, aminocarbonyloxy, methylaminocarbonyloxy, ethylaminocarbonyloxy, carboxy, methoxycarbonyl, ethoxycarbonyl, propoxycarbonyl, carbamoyl, N-methylcarbamoyl, N-ethylcarbamoyl, N,N-dimethylcarbamoyl, N,N-diethylcarbamoyl, formyl, acetyl, propionyl, 4-morpholino, 1-imidazolyl and succinimido; or B is a group of the formula -$A^3.B^1$ wherein $A^3$ is oxy, oxycarbonyl or imino and $B^1$ is a pyrrolyl, imidazolyl, pyrazolyl, pyridyl, pyrazinyl, pyrimidinyl, pyridazinyl, pyrrolidinyl, imidazolidinyl, pyrazolinyl, piperidinyl or piperazinyl moiety linked to $A^3$ by a ring carbon atom; or $A^3$ is oxycarbonyl and $B^1$ is a 4-morpholino group or a pyrrolidinyl, imidazolidinyl, pyrazolinyl, piperidinyl or piperazinyl moiety, optionally bearing a methyl or ethyl group and linked to $A^3$ by a ring nitrogen atom; $R^6$ is hydrogen, methyl or ethyl; $R^7$ is selected from hydrogen, methyl, ethyl, methoxy, ethoxy, fluoro, chloro, bromo, iodo, trifluoromethyl, cyano and nitro; X is phenylene optionally bearing a substituent selected from methyl, ethyl, methoxy, ethoxy, fluoro, chloro, bromo, iodo, formyl, acetyl, propionyl, trifluoromethyl, cyano and nitro; $R^8$ is hydrogen or a residue derived from a (1-6C)alkanol, or phenol or glycerol; and $R^9$ is methyl, ethyl, propyl, isopropyl, butyl, pentyl, cyclobutyl, cyclopentyl, cyclohexyl or phenyl; and wherein any of said phenyl moieties may be unsubstituted or bear one or two substituents selected from methyl, ethyl, methoxy, ethoxy, fluoro, chloro, bromo, cyano and trifluoromethyl.

3. A compound as claimed in claim 1 wherein $R^2$ is hydrogen, (1-8C)alkyl, (3-8C)cycloalkyl, (3-8C)cycloalkyl-(1-4C)alkyl, carboxy, (1-4C)alkoxycarbonyl, cyano, nitro, phenyl or phenyl(1-4C)alkyl; $R^4$ is selected from hydrogen, (1-4C)alkyl optionally bearing an amino, hydroxy or (1-4C)alkoxy substituent, carboxy, (1-4C)alkoxycarbonyl, cyano, nitro, carbamoyl, (1-4C)alkanoyl, N-alkylcarbamoyl and di-(N-alkyl)carbamoyl of up to 7 carbon atoms, halogeno, amino, alkylamino and dialkylamino of up to 6 carbon atoms and (1-4C)alkanoylamino; and X is phenylene optionally bearing a substituent selected from (1-4C)alkyl, (1-4C)alkoxy, halogeno, trifluoromethyl, cyano and nitro.

4. A compound as claimed in claim 1 wherein $R^4$ is selected from hydrogen, (1-4C)alkyl optionally bearing an amino, hydroxy or (1-4C)alkoxy substituent, carboxy, (1-4C)alkoxycarbonyl, (3-6C)alkenyloxycarbonyl, cyano, nitro, carbamoyl, (1-4C)alkanoyl, N-alkylcarbamoyl and di-(N-alkyl)carbamoyl of up to 7 carbon atoms, halogeno, amino, alkylamino and dialkylamino of up to 6 carbon atoms and (1-4C)alkanoylamino; or $R^4$ is a group of the formula -$A^1.A^2.B$ wherein $A^1$ is carbonyloxy, $A^2$ is (1-6C)alkylene and B is selected from hydroxy, (1-4C)alkoxy, phenyloxy, phenyl(1-4C)alkoxy, pyridyl(1-4C)alkoxy, phenylamino, amino, alkylamino and dialkylamino of up to 6 carbon atoms, (1-4C)alkanoylamino, (1-4C)alkylsulphonylamino, phenylsulphonylamino, sulphamoylamino (—NH.SO$_2$.NH$_2$), carboxamidomethylamino (—NH.CH$_2$.CO.NH$_2$), (1-4C)alkanoyloxy, phenylcarbonyloxy, aminocarbonyloxy (—O.CO.NH$_2$), (1-4C)alkylaminocarbonyloxy, carboxy, (1-4C)alkoxycarbony, carbamoyl, N-alkylcarbamoyl and di-(N-alkyl)carbamoyl of up to 7 carbon atoms, (1-4C)alkanoyl, 1-imidazolyl and succinimido group; or B is a group of the formula -$A^3.B^1$ wherein $A^3$ is oxy, oxycarbonyl or imino and $B^1$ is a 5 or 6-membered saturated or unsaturated heterocyclic ring containing 1 or 2 nitrogen atoms and linked to $A^3$ by a ring carbon atom; or $A^3$ is oxycarbonyl and $B^1$ is a 5 or 6-membered saturated heterocyclic ring containing 1 or 2 nitrogen atoms, optionally bearing a (1-4C)alkyl group and linked to $A^3$ by a ring nitrogen atom; and wherein $B^1$ the remainder of the ring atoms are carbon; and X is phenylene optionally bearing a substituent selected from (1-4C)alkyl, (1-4C)alkoxy, halogeno, trifluoromethyl, cyano and nitro.

5. A compound of the formula I as claimed in claim 1 wherein $R^4$ is (1-4C)alkoxycarbonyl or (3-6C)alkenyloxycarbonyl, $R^6$ is hydrogen and Z is carboxy or 1H-tetrazol-5-yl and is attached at the ortho position relative to X.

6. A compound of the formula Ib

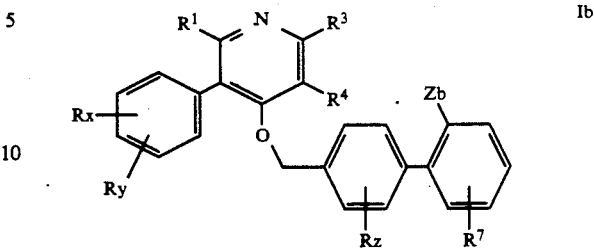

wherein Rz is hydrogen or a substituent selected from (1-4C)alkyl, (1-4C)alkoxy, halogeno, (1-4C)alkanoyl, trifluoromethyl, cyano and nitro group; Rx and Ry are independently selected from hydrogen, (1-4C)alkyl, (1-4C)alkoxy, halogeno, cyano and trifluoromethyl; Zb is 1H-tetrazol-5-yl or carboxy; and $R^1$, $R^3$, $R^4$ and $R^7$ have any of the values defined in any of claims 1 to 4; or a non-toxic salt thereof.

7. A compound of the formula I selected from:
methyl 2,6-dimethyl-4-[(2'-(1H-tetrazol-5-yl)biphenyl-4-yl)methoxy]pyridine-3-carboxylate;
methyl 2-ethyl-6-methyl-4-[(2'-(1H-tetrazol-5-yl)biphenyl-4-yl)methoxy]pyridine-3-carboxylate;
methyl 6-ethyl-2-methyl-4-[(2'-(1H-tetrazol-5-yl)biphenyl-4-yl)methoxy]pyridine-3-carboxylate;
methyl 2,6-diethyl-4-[(2'-(1H-tetrazol-5-yl)biphenyl-4-yl)methoxy]pyridine-3-carboxylate;
2,6-dimethyl-3-phenyl-4-[(2'-(1H-tetrazol-5-yl)biphenyl-4-yl)methoxy]pyridine; and
allyl 2,6-dimethyl-4-[(2'-(1H-tetrazol-5-yl)biphenyl-4-yl)methoxy]pyridine-3-carboxylate; and the non-toxic salts thereof.

8. A salt as claimed in claim 1 which is selected from salts with acids forming physiologically acceptable anions and, for those compounds of formula I which are acidic, alkali metal, alkaline earth metal, aluminium and ammonium salts, and salts with organic bases affording physiologically acceptable cations.

9. A method for antagonising one or more of the actions of angiotensin II in a warm-blooded animal requiring such treatment which comprises administering to said animal an antagonistically effective amount of a compound of formula I, or a non-toxic salt thereof, as defined in claim 1.

10. A pharmaceutical composition which comprises a compound of the formula I, or a non-toxic salt thereof, as claimed in claim 1, together with a pharmaceutically acceptable diluent or carrier.

11. A compound of the formula III

III wherein $R^1$, $R^2$, $R^3$, $R^4$, $R^5$, $R^6$, $R^7$ and X have any of the meanings defined in claim 1, and L is a protecting group.

* * * * *